US012670997B1

(12) United States Patent (10) Patent No.: US 12,670,997 B1
Toensing et al. (45) Date of Patent: *Jun. 30, 2026

(54) COMPUTER-IMPLEMENTED SYSTEMS AND METHODS FOR MULTI-LEVEL DATA GROUPING AND GENERATION OF A HIERARCHICAL DATA DISPLAY FROM UNIFORM CLAIMS DATA

(71) Applicant: Optum, Inc., Minnetonka, MN (US)

(72) Inventors: Peter N. Toensing, Richfield, MN (US); Bob Martin, Chandler, AZ (US)

(73) Assignee: Optum, Inc., Minnetonka, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/240,823

(22) Filed: Jun. 17, 2025

Related U.S. Application Data

(63) Continuation of application No. 18/607,945, filed on Mar. 18, 2024, now Pat. No. 12,367,984, which is a continuation of application No. 16/881,672, filed on May 22, 2020, now Pat. No. 11,967,431.

(51) Int. Cl.
| | |
|---|---|
| *G16H 50/30* | (2018.01) |
| *G16H 10/65* | (2018.01) |
| *G16H 20/10* | (2018.01) |
| *G16H 50/70* | (2018.01) |
| *G16H 70/40* | (2018.01) |

(52) U.S. Cl.
CPC ............. *G16H 50/30* (2018.01); *G16H 10/65* (2018.01); *G16H 20/10* (2018.01); *G16H 50/70* (2018.01); *G16H 70/40* (2018.01)

(58) Field of Classification Search
CPC ........ G16H 50/30; G16H 10/65; G16H 20/10; G16H 50/70; G16H 70/40
See application file for complete search history.

(56) References Cited

U.S. PATENT DOCUMENTS

| | | | |
|---|---|---|---|
| 5,835,897 | A | 11/1998 | Dang |
| 6,370,511 | B1 | 4/2002 | Dang |
| 7,127,407 | B1 | 10/2006 | Averill et al. |
| 7,203,677 | B1 | 4/2007 | Dettinger et al. |
| 7,389,245 | B1 | 6/2008 | Ashford et al. |

(Continued)

OTHER PUBLICATIONS

Optuminsight, Symmetry Episode Treatment Groups: Measuring health care with meaningful episodes of care, 2020, Eden Prairie, MN (Year: 2020).*

(Continued)

*Primary Examiner* — Kambiz Abdi
*Assistant Examiner* — Tran N Nguyen
(74) *Attorney, Agent, or Firm* — Alston & Bird LLP

(57) ABSTRACT

Hierarchical data objects are generated via a computer-based system for applying a series of rules to establish episode-specific data objects reflecting a plurality of discrete claim records before further dissecting the generated episode-specific data objects prior to finalization of those episode-specific data objects to identify claim records within the episode-specific data objects that are eligible for generation of one or more sub-episodes within the episode-specific data objects. The identified sub-episodes are reflected within the episode-specific data object to designate complete episodes of care that additionally reflect interactions with the corresponding parent episode.

20 Claims, 22 Drawing Sheets

(56) References Cited

U.S. PATENT DOCUMENTS

| | | | |
|---|---|---|---|
| 7,620,560 | B2 | 11/2009 | Dang |
| 7,711,577 | B2 | 5/2010 | Dust et al. |
| 7,725,333 | B2 | 5/2010 | Dang |
| 7,739,126 | B1 | 6/2010 | Cave et al. |
| 7,774,216 | B2 | 8/2010 | Dang |
| 7,774,252 | B2 | 8/2010 | Seare et al. |
| 7,818,181 | B2 | 10/2010 | Green |
| 7,979,290 | B2 | 7/2011 | Dang |
| 8,121,869 | B2 | 2/2012 | Dang |
| 8,296,165 | B2 | 10/2012 | Dang |
| 8,301,464 | B1 | 10/2012 | Cave et al. |
| 8,700,433 | B2 | 4/2014 | Dang |
| 9,946,839 | B1 | 4/2018 | Wilson et al. |
| 12,367,984 | B1 * | 7/2025 | Toensing ............... G16H 20/10 |
| 2002/0173989 | A1 | 11/2002 | Dang |
| 2004/0128163 | A1 | 7/2004 | Goodman et al. |
| 2012/0215563 | A1 | 8/2012 | Lassen et al. |
| 2013/0006672 | A1 * | 1/2013 | Dang ..................... G06Q 30/02 |
| | | | 705/2 |
| 2017/0286604 | A1 * | 10/2017 | Kido ..................... G16H 15/00 |
| 2018/0052956 | A1 | 2/2018 | Sevenster et al. |
| 2018/0174688 | A1 * | 6/2018 | Pecora ................ G06F 16/9535 |
| 2019/0051404 | A1 | 2/2019 | Cave |
| 2020/0111546 | A1 | 4/2020 | Syeda-Mahmood et al. |

OTHER PUBLICATIONS

OptumInsight, Symmetry Pharmacy Risk Groups: A pharmacy-based approach to cost risk assessment, 2021, Eden Prairie, MN (Year: 2021).*

Miller, Improving Resource Use Measurement Under MACRA: Creating Better Methods of Accountability for Healthcare Spending in Value-Based Purchasing and Alternative Payment Models, 2016, Center for Healthcare Quality and Payment Reform, www.CHQPR.org (Year: 2016).*

Advisory Action (PTOL-303) Mailed on Feb. 6, 2023 for U.S. Appl. No. 16/881,672, 8 page(s).

Advisory Action (PTOL-303) Mailed on Nov. 27, 2023 for U.S. Appl. No. 16/881,672, 7 page(s).

Centers for Medicare & Medicaid Services, 2022 Episode-Based Cost Measures Field Testing Wave 4 Measure Development Process, 2022, cms.gov (Year: 2022).

Claus, Clinical care management and workflow by episodes, 1997, Proc AMIA Annu Fall Symp, 91-95. (Year: 1997).

Ferris, Tim, et al., Ingenix request for reconsideration of cost of care measures, Feb. 7, 2012, National Quality Forum, 417, https://www.qualityforum.org/Projects/e-g/Efficiency/Meeting_Materials_02-28-2012.aspx, Jun. 25, 2020.

Final Rejection Mailed on Oct. 5, 2022 for U.S. Appl. No. 16/881,672, 33 page(s).

Final Rejection Mailed on Sep. 13, 2023 for U.S. Appl. No. 16/881,672, 33 page(s).

MaCurdy, Recommendations Regarding Implementation of MACRA Section 101(f) Requirements to Improve Resource Use Measurement, Including Comments on "CMS Episode Groups" Document, 2016, https://web.archive.org/web/20160401025413/https://chqpr.org/downloads/CHQPRComments_on_Resource_Use_Measurement.pdf (Year: 2016).

Non-Final Rejection Mailed on Jun. 2, 2022 for U.S. Appl. No. 16/881,672, 46 page(s).

Non-Final Rejection Mailed on Mar. 30, 2023 for U.S. Appl. No. 16/881,672, 33 page(s).

Notice of Allowance and Fees Due (PTOL-85) Mailed on Jan. 4, 2024 for U.S. Appl. No. 16/881,672, 15 page(s).

Notice of Allowance and Fees Due (PTOL-85) Mailed on Mar. 18, 2025 for U.S. Appl. No. 18/607,945, 12 page(s).

OpenEHR Clinical, Problem, Issue, Diagnosis and Concern, 2016, https://openehr.atlassian.net/wiki/spaces/healthmod/pages/2949176/Problem+Issue+Diagnosis+and+Concern (Year: 2016).

OptumInsight, symmetry episode treatment groups, 2017, Eden Prairie, MN (Year: 2017).

Peterson, A practical guide to episode groupers for cost-of-illness analysis in health services research, 2019, SAGE Open Med, 7: 2050312119840200 (Year: 2019).

* cited by examiner

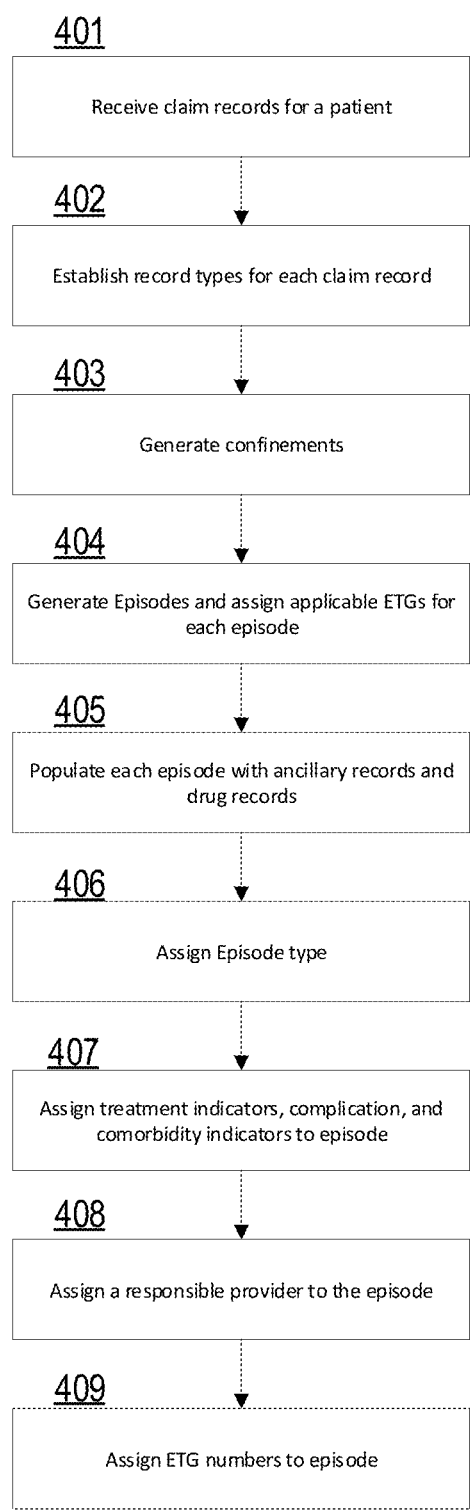

<u>401</u>

Receive claim records for a patient

<u>402</u>

Establish record types for each claim record

<u>403</u>

Generate confinements

<u>404</u>

Generate Episodes and assign applicable ETGs for each episode

<u>405</u>

Populate each episode with ancillary records and drug records

<u>406</u>

Assign Episode type

<u>407</u>

Assign treatment indicators, complication, and comorbidity indicators to episode <u>408</u>

Assign a responsible provider to the episode

<u>409</u>

Assign ETG numbers to episode

FIG. 4

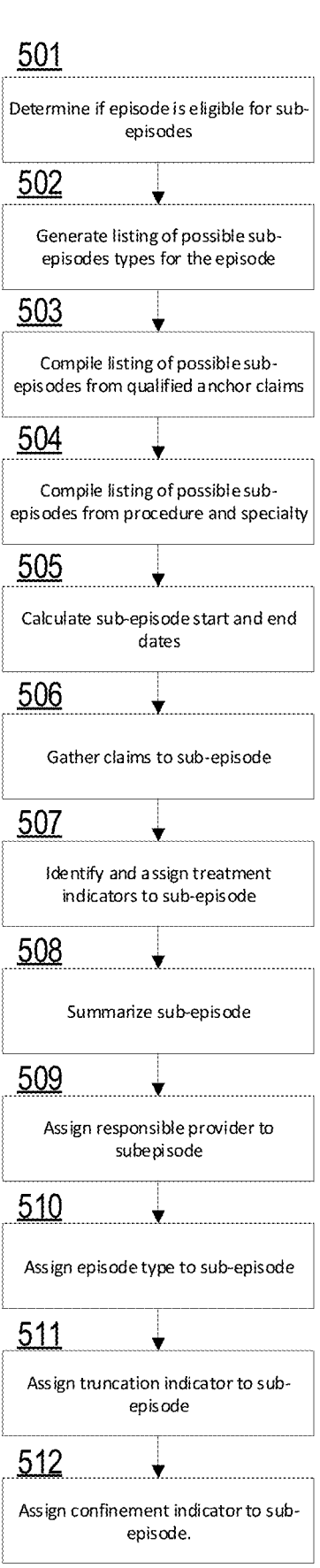

501

Determine if episode is eligible for sub-episodes

502

Generate listing of possible sub-episodes types for the episode

503

Compile listing of possible sub-episodes from qualified anchor claims

504

Compile listing of possible sub-episodes from procedure and specialty

505

Calculate sub-episode start and end dates

506

Gather claims to sub-episode

507

Identify and assign treatment indicators to sub-episode

508

Summarize sub-episode

509

Assign responsible provider to subepisode

510

Assign episode type to sub-episode

511

Assign truncation indicator to sub-episode

512

Assign confinement indicator to sub-episode.

FIG. 5

COMPUTER-IMPLEMENTED SYSTEMS AND METHODS FOR MULTI-LEVEL DATA GROUPING AND GENERATION OF A HIERARCHICAL DATA DISPLAY FROM UNIFORM CLAIMS DATA

CROSS-REFERENCE TO RELATED APPLICATIONS

This patent application is a continuation of U.S. application Ser. No. 18/607,945, filed Mar. 18, 2024, which is a continuation of U.S. application Ser. No. 16/881,672, filed May 22, 2020 and now issued as U.S. Pat. No. 11,967,431, the contents of both of which are incorporated herein by reference in their entirety

BACKGROUND

The complex and interdependent nature of certain periodically-generated data sets, such as medical data generated over a lengthy time period during treatment of a particular condition for a patient (whether acute or chronic), generally cannot be automatically reflected within data displays without substantial computational data manipulation. However, existing data grouping systems for generating usable data displays reflecting various medical treatments are incapable of providing a complete view of multi-faceted treatments that may be ongoing with a particular patient. Accordingly, a need exists for improved data grouping systems and methods for providing increased usability of a resulting data analysis display.

BRIEF SUMMARY

Various embodiments are directed to systems and methods for intaking claims data relating to medical products and/or services provided to a patient over time, for generating one or more episodes of care encompassing one or more discrete claims, and executing one or more rule-engines to identify potential sub-episodes that may be attributed to a generated episode so as to provide a multi-layer view of medical care provided to a patient. The rule-engines are configured for identifying individual claims data records or sets of claims data records satisfying parent-episode eligibility criteria (indicating that a particular episode is eligible for hosting sub-episodes), for identifying individual claims data records of sets of claims data records satisfying sub-episode eligibility criteria (indicating eligibility for classification as a sub-episode), and for establishing a parent-sub-episode hierarchy upon determining satisfaction of one or more applicable relational criteria (e.g., time-based criteria). Upon generating a hierarchical set of episodes encompassing parent- and sub-episodes, various systems and methods are configured for generating reports indicative of the relational episodes and/or for enabling data access by various external systems for additional data processing.

Certain embodiments are directed to a computer-based system for generating hierarchical episode-based data object each representing a hierarchical arrangement of a plurality of discrete claim records, the system comprising: one or more memory storage areas comprising a claims data storage area storing a plurality of individual claim records; one or more processors collectively configured to: generate a plurality of parent episode data objects each relating to an episode-specific subset of individual claim records selected from the plurality of individual claim records, wherein each of the plurality of parent episode data objects defines an episode date range identifying an episode start date and an episode end date and wherein each of the plurality of parent episode data objects identifies a parent episode anchor record of the episode specific subset of individual claim records establishing characteristics of the episode; sequentially identify, from the plurality of parent episode data objects, a subset of the plurality of parent episode data objects eligible for supporting one or more sub-episodes; retrieve one or more sub-episode eligibility criteria reference tables from the one or more memory storage areas; for a first parent episode data object of the subset of the plurality of parent episode data objects indicated as eligible for supporting one or more sub-episodes, sequentially generate, within a temporary memory storage area of the one or more memory storage areas, a sub-episode eligibility listing based at least in part on the parent episode anchor record establishing characteristics of the episode; query each of the claim records related to the first parent episode data object to identify one or more sub-episode anchor records satisfying the sub-episode eligibility criteria; identify sub-episode ancillary records associated with the one or more sub-episode anchor records; update the first parent episode data file to provide a hierarchical data structure including one or more sub-episode identifiers corresponding with one or more sub-episodes each occurring within the episode date range; and store, within the one or more memory storage areas, the updated first parent episode data file for access by additional analysis engines.

In certain embodiments, a parent episode anchor record associated with the first parent episode comprises data identifying a plurality of diagnosis codes associated with the first parent anchor record, and wherein the one or more sub-episode eligibility criteria reference tables establish a listing of diagnosis codes eligible for supporting one or more sub-episodes, and generating a sub-episode eligibility listing comprises identifying those diagnosis codes existing in both the first parent anchor record and the sub-episode eligibility criteria. Moreover, in various embodiments, the parent episode anchor record, having one or more diagnosis codes meeting sub-episode eligibility criteria, further identifies a procedure code associated with the first parent anchor record, and wherein the one or more sub-episode eligibility criteria reference tables establish a listing of procedure codes eligible for supporting one or more sub-episodes, and generating a sub-episode eligibility listing comprises identifying one or more procedure codes existing in both the first parent anchor record and the sub-episode eligibility criteria. In certain embodiments, the first parent episode data object identifies a responsible provider for the episode, and wherein the one or more sub-episode eligibility criteria reference tables establish a listing of provider specialties eligible for supporting one or more sub-episodes, and wherein the one or more processors are further configured to: reference one or more provider specialty tables to determine a provider specialty associated with the responsible provider; and determine whether the provider specialty of the responsible provider supports one or more sub-episodes.

In various embodiments, identifying one or more ancillary records comprises: identifying one or more ancillary records within the episode-specific subset of individual claim records to be associated with the sub-episode anchor record; identifying one or more ancillary records not identified within the episode-specific subset of individual claim records to be associated with the sub-episode anchor record; determining a sub-episode date range established based at least in part on the one or more ancillary records associated with the sub-episode; and truncate the sub-episode date range based on the episode date range such that the sub-episode occurs during the date range of the first parent episode data object. Moreover, in certain embodiments, identifying one or more sub-episode anchor records comprises identifying a first sub-episode anchor record and a second sub-episode anchor record; and wherein the one or more processors are further configured to: establish a sub-episode priority based at least in part on priority scores associated with each of the first sub-episode anchor record and the second sub-episode anchor record; establish a first sub-episode date range associated with the first sub-episode anchor record and a second sub-episode date range associated with the second sub-episode anchor record; and truncate one of the first-sub episode date range or the second sub-episode date range based at least in part on the sub-episode priority such that the first sub-episode does not overlap the second sub-episode. In various embodiments, the processors are additionally configured to identify, based at least in part on claim records associated with the one or more sub-episodes, at least one provider associated with the one or more claim records; and wherein the one or more processors are further configured to attribute, based at least in part on associations between each provider and the claim records, each of the one or more sub-episodes to a responsible provider of the at least one provider.

Certain embodiments are directed to a computer-implemented method for generating hierarchical episode-based data objects, the computer-implemented method comprising: storing, in one or more memory storage areas, a plurality of individual claim records; generating, via one or more processors, a plurality of parent episode data objects each relating to an episode-specific subset of individual claim records selected from the plurality of individual claim records, wherein each of the plurality of parent episode data objects defines an episode date range identifying an episode start date and an episode end date and wherein each of the plurality of parent episode data objects identifies a parent episode anchor record of the episode specific subset of individual claim records establishing characteristics of the episode; sequentially identifying, via the one or more processors and from the plurality of parent episode data objects, a subset of the plurality of parent episode data objects eligible for supporting one or more sub-episodes; retrieving, via the one or more processors, one or more sub-episode eligibility criteria reference tables from the one or more memory storage areas; for a first parent episode data object of the subset of the plurality of parent episode data objects indicated as eligible for supporting one or more sub-episodes, sequentially generating, via the one or more processors, within a temporary memory storage area of the one or more memory storage areas, a sub-episode eligibility listing based at least in part on the parent episode anchor record establishing characteristics of the episode; querying, via the one or more processors, each of the claim records related to the first parent episode data object to identify one or more sub-episode anchor records satisfying the sub-episode eligibility criteria; identifying, via the one or more processors, sub-episode ancillary records associated with the one or more sub-episode anchor records; updating, via the one or more processors, the first parent episode data file to provide a hierarchical data structure including one or more sub-episode identifiers corresponding with one or more sub-episodes each occurring within the episode date range; and storing, via the one or more processors and within the one or more memory storage areas, the updated first parent episode data file for access by additional analysis engines.

In various embodiments, a parent episode anchor record associated with the first parent episode comprises data identifying a plurality of diagnosis codes associated with the first parent anchor record, and wherein the one or more sub-episode eligibility criteria reference tables establish a listing of diagnosis codes eligible for supporting one or more sub-episodes, and generating a sub-episode eligibility listing comprises identifying those diagnosis codes existing in both the first parent anchor record and the sub-episode eligibility criteria. In certain embodiments, the method further comprises identifying, based at least in part on claim records associated with the one or more sub-episodes, at least one provider associated with the one or more claim records; and wherein the one or more processors are further configured to attribute, based at least in part on associations between each provider and the claim records, each of the one or more sub-episodes to a responsible provider of the at least one provider.

In various embodiments, the first parent episode data object identifies a responsible provider for the episode, and wherein the one or more sub-episode eligibility criteria reference tables establish a listing of provider specialties eligible for supporting one or more sub-episodes, and wherein the method further comprises: referencing one or more provider specialty tables to determine a provider specialty associated with the responsible provider; and determining whether the provider specialty of the responsible provider supports one or more sub-episodes.

In various embodiments, identifying one or more ancillary records comprises: identifying one or more ancillary records within the episode-specific subset of individual claim records to be associated with the sub-episode anchor record; identifying one or more ancillary records not identified within the episode-specific subset of individual claim records to be associated with the sub-episode anchor record; determining a sub-episode date range established based at least in part on the one or more ancillary records associated with the sub-episode; and truncate the sub-episode date range based on the episode date range such that the sub-episode occurs during the date range of the first parent episode data object.

In various embodiments, identifying one or more sub-episode anchor records comprises identifying a first sub-episode anchor record and a second sub-episode anchor record; and wherein the method further comprises: establishing a sub-episode priority based at least in part on priority scores associated with each of the first sub-episode anchor record and the second sub-episode anchor record; establishing a first sub-episode date range associated with the first sub-episode anchor record and a second sub-episode date range associated with the second sub-episode anchor record; and truncating one of the first-sub episode date range or the second sub-episode date range based at least in part on the sub-episode priority such that the first sub-episode does not overlap the second sub-episode.

In certain embodiments, generating a parent episode data object of the plurality of parent episode data objects comprises storing the parent episode data object within temporary storage. In various embodiments, the method further comprises establishing an ETG code for the parent episode and each of the one or more sub-episodes, wherein at least one of the one or more sub-episodes has an ETG code different from an ETG code associated with the parent episode.

Certain embodiments are directed to a computer program product for generating hierarchical episode-based data objects, the computer program product comprising at least one non-transitory computer-readable storage medium having computer-readable program code portions stored therein, the computer-readable program code portions configured to: store, in one or more memory storage areas, a plurality of individual claim records; generate, via one or more processors, a plurality of parent episode data objects each relating to an episode-specific subset of individual claim records selected from the plurality of individual claim records, wherein each of the plurality of parent episode data objects defines an episode date range identifying an episode start date and an episode end date and wherein each of the plurality of parent episode data objects identifies a parent episode anchor record of the episode specific subset of individual claim records establishing characteristics of the episode; sequentially identify, via the one or more processors and from the plurality of parent episode data objects, a subset of the plurality of parent episode data objects eligible for supporting one or more sub-episodes; retrieve, via the one or more processors, one or more sub-episode eligibility criteria reference tables from the one or more memory storage areas; for a first parent episode data object of the subset of the plurality of parent episode data objects indicated as eligible for supporting one or more sub-episodes, sequentially generate, via the one or more processors, within a temporary memory storage area of the one or more memory storage areas, a sub-episode eligibility listing based at least in part on the parent episode anchor record establishing characteristics of the episode; query, via the one or more processors, each of the claim records related to the first parent episode data object to identify one or more sub-episode anchor records satisfying the sub-episode eligibility criteria; identify, via the one or more processors, sub-episode ancillary records associated with the one or more sub-episode anchor records; update, via the one or more processors, the first parent episode data file to provide a hierarchical data structure including one or more sub-episode identifiers corresponding with one or more sub-episodes each occurring within the episode date range; and store, via the one or more processors and within the one or more memory storage areas, the updated first parent episode data file for access by additional analysis engines.

In various embodiments, a parent episode anchor record associated with the first parent episode comprises data identifying a plurality of diagnosis codes associated with the first parent anchor record, and wherein the one or more sub-episode eligibility criteria reference tables establish a listing of diagnosis codes eligible for supporting one or more sub-episodes, and generating a sub-episode eligibility listing comprises identifying those diagnosis codes existing in both the first parent anchor record and the sub-episode eligibility criteria. In certain embodiments, the computer program product further comprises one or more executable portions configured to identify, based at least in part on claim records associated with the one or more sub-episodes, at least one provider associated with the one or more claim records; and wherein the one or more processors are further configured to attribute, based at least in part on associations between each provider and the claim records, each of the one or more sub-episodes to a responsible provider of the at least one provider. In various embodiments, the first parent episode data object identifies a responsible provider for the episode, and wherein the one or more sub-episode eligibility criteria reference tables establish a listing of provider specialties eligible for supporting one or more sub-episodes, and further comprising executable portions configured to: reference one or more provider specialty tables to determine a provider specialty associated with the responsible provider; and determine whether the provider specialty of the responsible provider supports one or more sub-episodes.

In certain embodiments, identifying one or more ancillary records comprises: identifying one or more ancillary records within the episode-specific subset of individual claim records to be associated with the sub-episode anchor record; identifying one or more ancillary records not identified within the episode-specific subset of individual claim records to be associated with the sub-episode anchor record; determining a sub-episode date range established based at least in part on the one or more ancillary records associated with the sub-episode; and truncate the sub-episode date range based on the episode date range such that the sub-episode occurs during the date range of the first parent episode data object.

BRIEF DESCRIPTION OF THE SEVERAL VIEWS OF THE DRAWINGS

Reference will now be made to the accompanying drawings, which are not necessarily drawn to scale, and wherein:

FIG. 4 is a flowchart illustrating various steps associated with generation of episodes of care for a particular patient in accordance with certain embodiments;

FIG. 5 is a flowchart illustrating various steps associated with generation of a sub-episode of care for a particular patient in accordance with certain embodiments.

DETAILED DESCRIPTION

Figure 1:
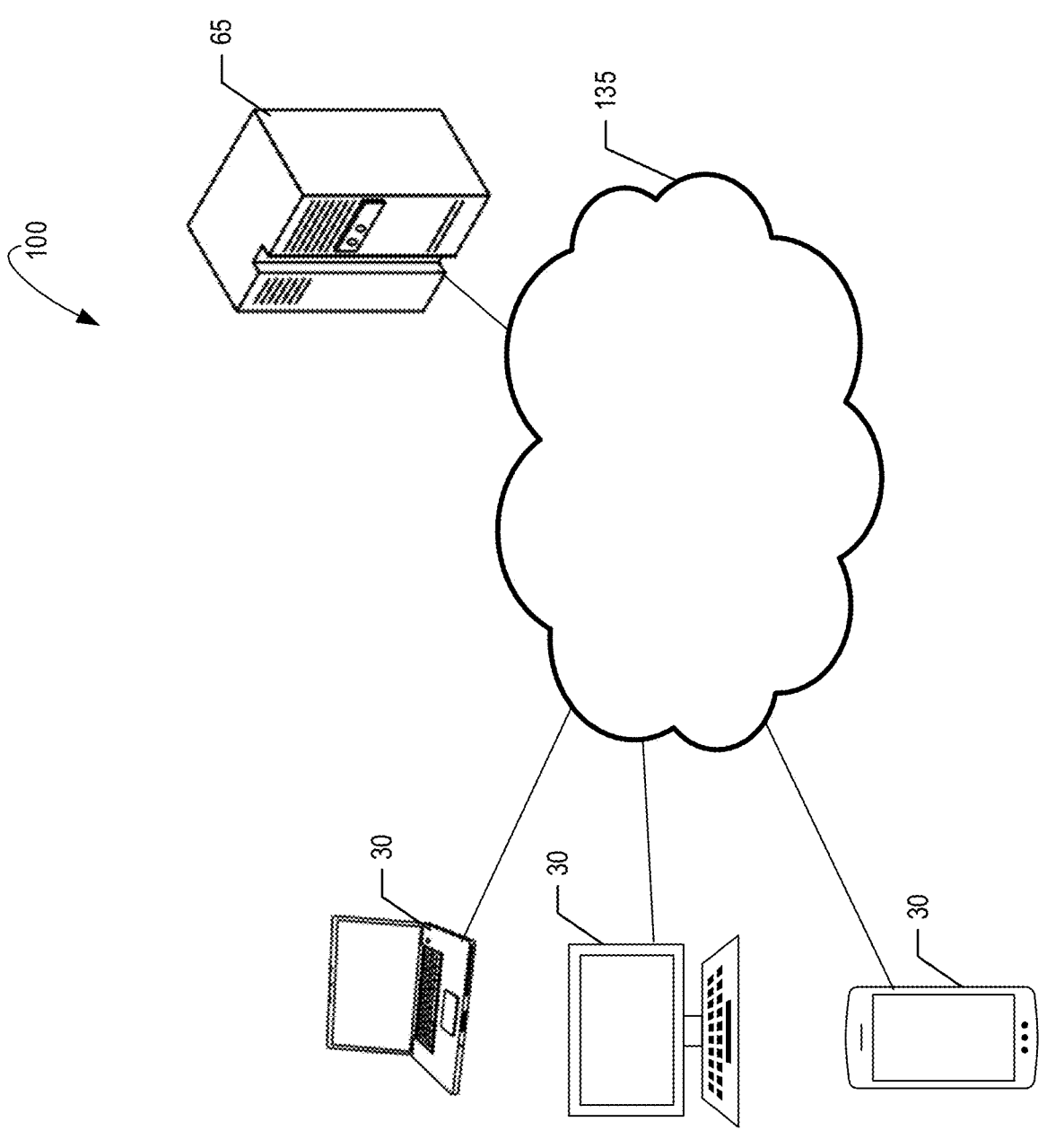
FIG. 1 is a diagram of a system that can be used in conjunction with various embodiments of the present invention.

The present disclosure more fully describes various embodiments with reference to the accompanying drawings. It should be understood that some, but not all embodiments are shown and described herein. Indeed, the embodiments may take many different forms, and accordingly this disclosure should not be construed as limited to the embodiments set forth herein. Rather, these embodiments are provided so that this disclosure will satisfy applicable legal requirements. Like numbers refer to like elements throughout.

I. DEFINITIONS

"Episodes" represent episodes of care for a patient comprising collected claim record data organized into coherent and related groupings of claim records each relating to treatment of a particular condition (e.g., chronic conditions or acute conditions) for a patient. The data to be included within individual episodes, including the selection of specific claim records for inclusion within an episode may be determined at least in part on Episode Treatment Groups (ETGs) as defined herein.

ETGs are used to define the basic analytical unit in the computer-implemented method of certain embodiments.

ETGs are episode based and reflect a clinically homogenous and statistically stable group of similar illness etiology and therapeutic treatment. ETGs as discussed herein may encompass in-patient related treatments, out-patient related treatments, or other medical treatments. ETG grouper method uses service or segment-level claim data as input data and assigns each service to the appropriate episode.

Using ETGs as the basic episodic definer enables various embodiments to track concurrently and recurrently occurring illnesses and correctly identify and assign events (e.g., medical services provided, medical products provided, such as pharmaceuticals, equipment, and/or the like) to the appropriate episode. Additionally, ETGs account for changes in a patient's condition during a course of treatment by shifting from the initially defined ETG to one which includes the changed condition once the changed condition is identified.

ETGs gather in-patient, out-patient, ambulatory, ancillary, and/or other claims into treatment episodes, regardless of treatment duration, then use clinical algorithms to identify concurrent and/or recurrent episodes. ETG grouper systems and methods continue to collect information until an absence of treatment is detected for a predetermined period of time commensurate with the episode. For example, a bronchitis episode will have a sixty-day window, while an asthma episode may have a one-year window. Subsequent records of the same nature within the window reset the window for an additional period of time until the patient is asymptomatic for the pre-determined time period.

ETGs can identify a change in the patient's condition and shift the patient's episode from the initially defined ETG to the ETG which includes the change in condition. ETGs identify all providers treating a single illness episode, allowing the user to uncover specific treatment patterns. After adjusting for case-mix, ETGs measure and compare the financial and clinical performance of individual providers or entire networks.

Episodes may be indicated as "parent episodes," reflecting that the episode is a hierarchical episode including one or more sub-episodes therein. Those "sub-episodes" as discussed herein are complete individual episodes that are nested within a parent episode. Episodes that are neither parent episodes nor sub-episodes-those that are not nested within other episodes nor include one or more episodes nested therein, are referred to herein as "flat episodes." However, it should be understood that general references to "episodes" or "ETGs" are provided as generic references that apply to any episode type.

"Diagnosis codes" refer to unique codes utilized to consistently identify particular diagnoses of a patient. These diagnosis codes may be standardized and utilized across a medical industry, such as ICD-9 or ICD-10 codes published by the Word Health Organization (WHO) that may be utilized by healthcare professionals to quickly identify diagnoses of medical conditions established by other healthcare professionals. Thus, healthcare providers, payers, and/or others in the medical industry need not utilize self-established descriptors of particular patient diagnoses that may or may not be readily understood by others. Similarly, "procedure codes" and "pharmacy codes" refer to standardized identifiers assigned to particular procedures and medications, respectively, that may translate across languages and between healthcare professionals to consistently identify procedures and/or medications performed for/taken by certain patients. These diagnosis codes, procedure codes, pharmacy codes, and/or other standardized code systems that may be utilized for characterizing particular aspects of a condition and/or treatment of a patient may be utilized as reference codes for retrieving additional data and/or for retrieving relevant data tables for generating appropriate episode and/or sub-episode types, for providing relevant characteristics to episodes or sub-episodes, and/or the like.

As used herein, "Management records" are defined as claims which represent a service by a provider engaging in the direct evaluation, management or treatment of a patient. Examples of management records include office visits and therapeutic services. Management records serve as anchor records because they represent focal points in the patient treatment as well as for related ancillary services.

"Ancillary records" are claims which represent services which are incidental to the direct evaluation, management and treatment of the patient. Examples of ancillary records include X-ray and laboratory tests.

"Surgery records" are specific surgical claims. Surgery records also serve as anchor records.

"Facility records" are claims indicating admission to a facility such as an acute care hospital. Examples of facility records include inpatient room and board charges.

"Drug records" relate to pharmaceutical prescription claims.

"Other records" are those medical claim records which are not management, surgery, ancillary, facility or drug records.

Invalid records are flagged and logged to an error output file for the user. Valid records are then processed by an ETG Assignor Sub-routine and, based upon diagnosis code, is either matched to existing open episodes for the patient or serve to create new episodes.

Management, surgery, and facility records serve as "anchor records." An "anchor record" is a record which originates a diagnosis or a definitive treatment for a given medical condition. Management and surgery records serve as base reference records for facility, ancillary and drug claim records relating to the diagnosis or treatment which is the subject of the management or surgery record. Only management and surgery records can serve to start a given episode.

A "cluster" is a grouping of one, and only one, anchor record (management, surgery or facility), and possibly ancillary and/or drug records. A cluster represents a group of services in which the focal point, and therefore the responsible medical personnel, is the anchor record. An episode is made up of one or more clusters.

"Orphan" records as discussed herein may encompass ancillary records that does not match an active ETG.

A phantom record is an anchor record, management or surgery, with more than one diagnosis, which is assigned to one episode and its corresponding ETG based on one diagnosis, but can start a new episode(s) or update the most recent date of another active episode(s) based on other diagnoses on the record.

Comorbidities, complications or a defining surgery could require an update of the patient's condition to an ETG requiring a more aggressive treatment profile. ETG tracks changes in the patient's clinical condition and shifts the patient's episode from the initially defined ETG to an ETG which includes the change in clinical condition.

II. COMPUTER PROGRAM PRODUCTS, METHODS, AND COMPUTING ENTITIES

Embodiments of the present invention may be implemented in various ways, including as computer program products that comprise articles of manufacture. Such computer program products may include one or more software components including, for example, software objects, methods, data structures, and/or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magneto resistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of a data structure, apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

III. EXEMPLARY SYSTEM ARCHITECTURE

FIG. 1 provides an illustration of a system 100 that can be used in conjunction with various embodiments of the present invention. As shown in FIG. 1, the system 100 may comprise one or more data management computing entities 65, one or more user computing entities 30 (e.g., which may encompass handheld computing devices, laptop computing devices, desktop computing devices, and/or one or more Internet of Things (IoT) devices, such as wearable devices, medical devices (e.g., Continuous positive airway pressure (CPAP) machines), and/or the like, one or more networks 135, and/or the like. Each of the components of the system may be in electronic communication with, for example, one another over the same or different wireless or wired networks 135 including, for example, a wired or wireless Personal Area Network (PAN), Local Area Network (LAN), Metropolitan Area Network (MAN), Wide Area Network (WAN), and/or the like. Additionally, while FIG. 1 illustrate certain system entities as separate, standalone entities, the various embodiments are not limited to this particular architecture.

a. Exemplary Data Management Computing Entity

Figure 2A:
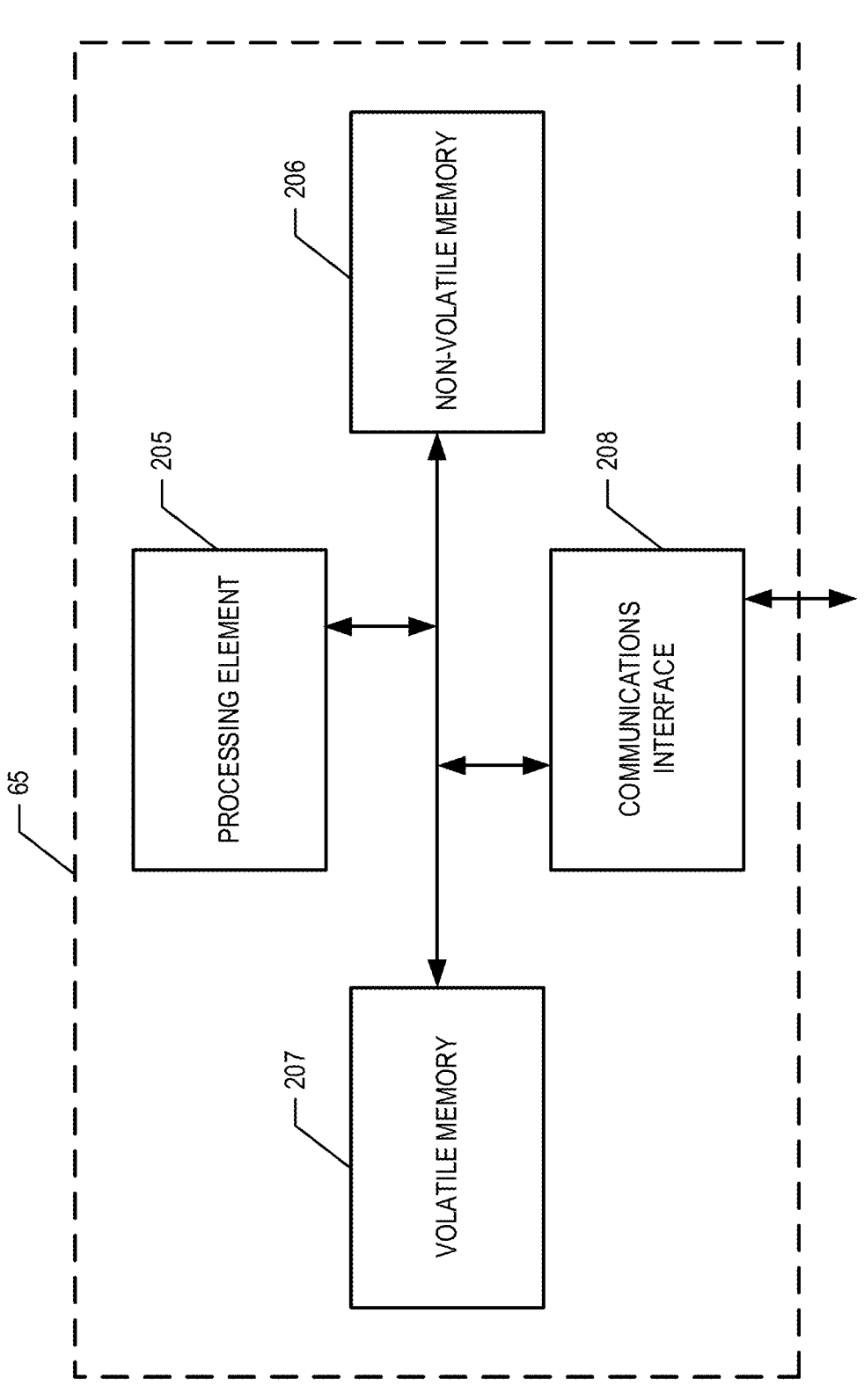
FIG. 2A is a schematic of a data management computing entity in accordance with certain embodiments of the present invention.

FIG. 2A provides a schematic of a data management computing entity 65 according to one embodiment of the present invention. In general, the terms computing entity, entity, device, system, and/or similar words used herein interchangeably may refer to, for example, one or more computers, computing entities, desktop computers, mobile phones, tablets, phablets, notebooks, laptops, distributed systems, items/devices, terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the data management computing entity 65 may also include one or more network and/or communications interfaces 208 for communicating with various computing entities, such as by communicating data, content, information, and/or similar terms used herein interchangeably that can be transmitted, received, operated on, processed, displayed, stored, and/or the like. For instance, the data management computing entity 65 may communicate with other computing entities, one or more user computing entities 30, and/or the like.

As shown in FIG. 2A, in one embodiment, the data management computing entity 65 may include or be in communication with one or more processing elements 205 (also referred to as processors, processing circuitry, and/or similar terms used herein interchangeably) that communicate with other elements within the data management computing entity 65 via a bus, for example, or network connection. As will be understood, the processing element 205 may be embodied in a number of different ways. For example, the processing element 205 may be embodied as one or more complex programmable logic devices (CPLDs), microprocessors, multi-core processors, coprocessing entities, application-specific instruction-set processors (ASIPs), and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the data management computing entity 65 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or memory media 206 as described above, such as hard disks, ROM, PROM, EPROM, EEPROM, flash memory, MMCs, SD memory cards, Memory Sticks, CBRAM, PRAM, FeRAM, RRAM, SONOS, racetrack memory, and/or the like. As will be recognized, the non-volatile storage or memory media may store databases, metadata repositories database instances, database management system entities, data, applications, programs, program modules, scripts, source code, object code, byte code, compiled code, interpreted code, machine code, executable instructions, and/or the like. The term database, database instance, database management system entity, and/or similar terms used herein interchangeably and in a general sense to refer to a structured or unstructured collection of information/data that is stored in a computer-readable storage medium.

Memory media 206 (e.g., metadata repository) may also be embodied as a data storage device or devices, as a separate database server or servers, or as a combination of data storage devices and separate database servers. Further, in some embodiments, memory media 206 may be embodied as a distributed repository such that some of the stored information/data is stored centrally in a location within the system and other information/data is stored in one or more remote locations. Alternatively, in some embodiments, the distributed repository may be distributed over a plurality of remote storage locations only. An example of the embodiments contemplated herein would include a cloud data storage system maintained by a third-party provider and where some or all of the information/data required for the operation of the system may be stored. As a person of ordinary skill in the art would recognize, the information/data required for the operation of the system may also be partially stored in the cloud data storage system and partially stored in a locally maintained data storage system.

Figure 2B:
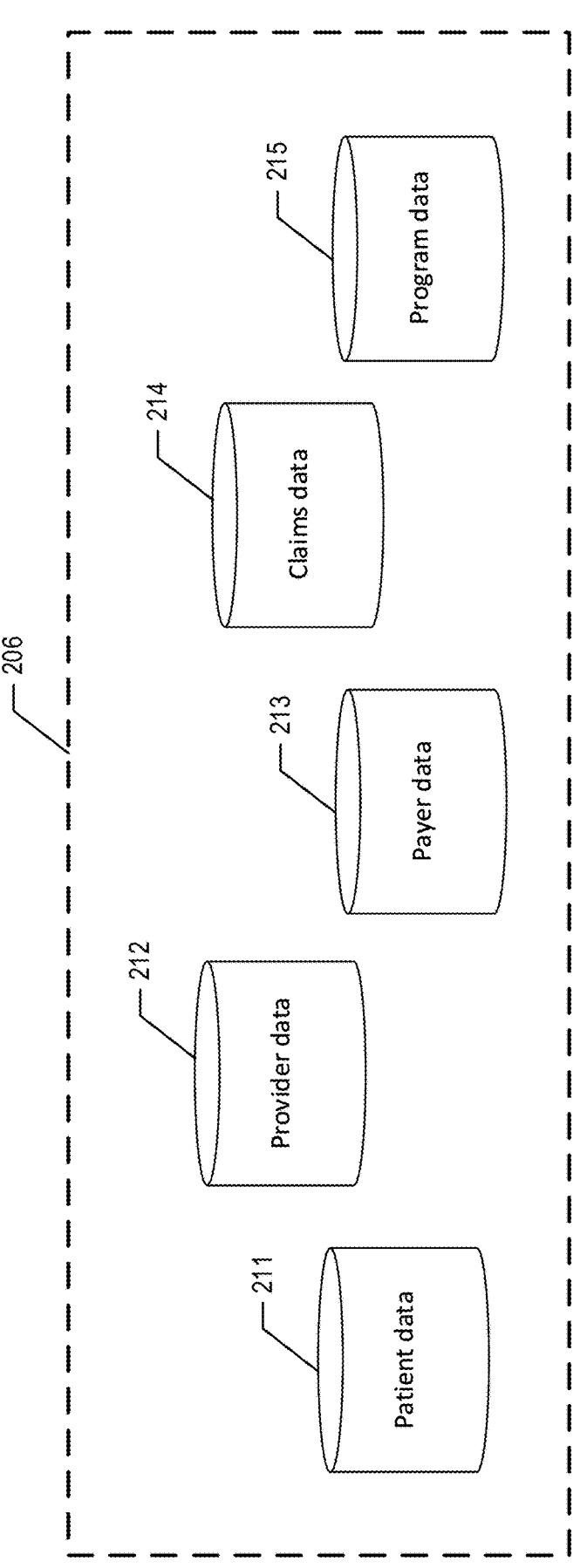
FIG. 2B is a schematic representation of a memory media storing a plurality of data assets.

Memory media 206 (e.g., metadata repository) may include information/data accessed and stored by the system to facilitate the operations of the system. More specifically, memory media 206 may encompass one or more data stores configured to store information/data usable in certain embodiments. For example, as shown in FIG. 2B, the memory media 206 may be embodied as one or more data storage areas (e.g., within a single centralized location or distributed among a plurality of disparate storage locations), and may comprise a plurality of data storage repositories, such as patient data storage area 211 (e.g., configured for storing patient data, such as patient profiles as discussed herein), a provider data storage area 212 (e.g., storing provider data, such as provider profiles as discussed herein), a payer data storage area (e.g., storing payer data, such as payer profiles as discussed herein), a claims data storage area (e.g., storing claims data as discussed herein), program data storage area 215 (e.g., storing data regarding various program requirements/criteria for eligibility and/or compliance of particular programs). Data stored within such data repositories may be utilized during operation of various embodiments as discussed herein.

In one embodiment, the data management computing entity 65 may further include or be in communication with volatile media (also referred to as volatile storage, memory, memory storage, memory circuitry and/or similar terms used herein interchangeably). In one embodiment, the volatile storage or memory may also include one or more volatile storage or memory media 207 as described above, such as RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. As will be recognized, the volatile storage or memory media may be used to store at least portions of the databases, database instances, database management system entities, data, applications, programs, program modules, scripts, source code, object code, byte code, compiled code, interpreted code, machine code, executable instructions, and/or the like being executed by, for example, the processing element 205. Thus, the databases, database instances, database management system entities, data, applications, programs, program modules, scripts, source code, object code, byte code, compiled code, interpreted code, machine code, executable instructions, and/or the like may be used to control certain aspects of the operation of the data management computing entity 65 with the assistance of the processing element 205 and operating system.

As indicated, in one embodiment, the data management computing entity 65 may also include one or more network and/or communications interfaces 208 for communicating with various computing entities, such as by communicating data, content, information, and/or similar terms used herein interchangeably that can be transmitted, received, operated on, processed, displayed, stored, and/or the like. For instance, the data management computing entity 65 may communicate with computing entities or communication interfaces of other computing entities, user computing entities 30, and/or the like. In this regard, the data management computing entity 65 may access various data assets.

As indicated, in one embodiment, the data management computing entity 65 may also include one or more network and/or communications interfaces 208 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the data management computing entity 65 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol. The data management computing entity 65 may use such protocols and standards to communicate using Border Gateway Protocol (BGP), Dynamic Host Configuration Protocol (DHCP), Domain Name System (DNS), File Transfer Protocol (FTP), Hypertext Transfer Protocol (HTTP), HTTP over TLS/SSL/Secure, Internet Message Access Protocol (IMAP), Network Time Protocol (NTP), Simple Mail Transfer Protocol (SMTP), Telnet, Transport Layer Security (TLS), Secure Sockets Layer (SSL), Internet Protocol (IP), Transmission Control Protocol (TCP), User Datagram Protocol (UDP), Datagram Congestion Control Protocol (DCCP), Stream Control Transmission Protocol (SCTP), Hypertext Markup Language (HTML), and/or the like.

As will be appreciated, one or more of the data management computing entity's components may be located remotely from other data management computing entity 65 components, such as in a distributed system. Furthermore, one or more of the components may be aggregated and additional components performing functions described herein may be included in the data management computing entity 65. Thus, the data management computing entity 65 can be adapted to accommodate a variety of needs and circumstances.

b. Exemplary User Computing Entity

Figure 3:
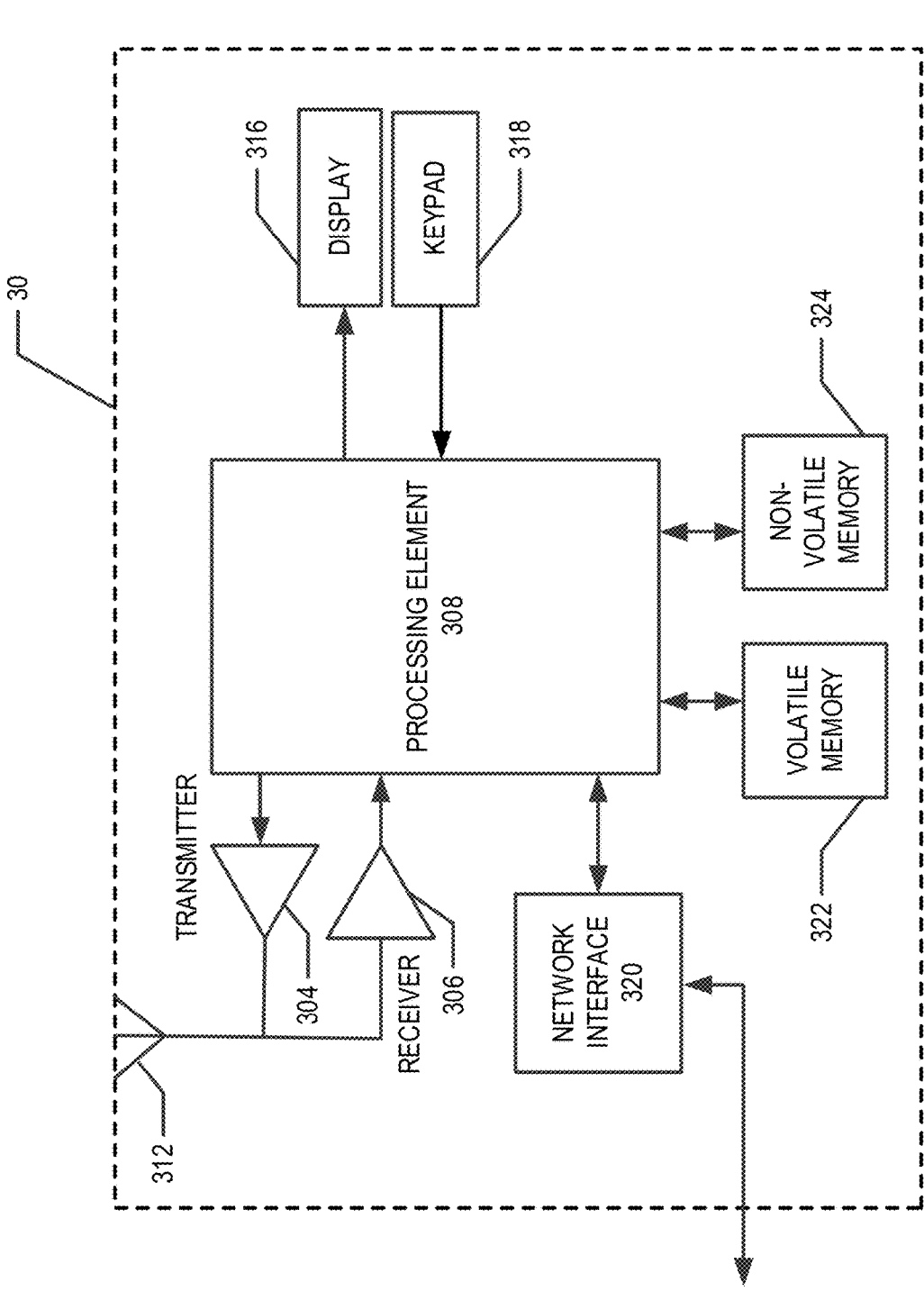
FIG. 3 is a schematic of a user computing entity in accordance with certain embodiments of the present invention.

FIG. 3 provides an illustrative schematic representative of user computing entity 30 that can be used in conjunction with embodiments of the present invention. As will be recognized, the user computing entity 30 may be operated by an agent and include components and features similar to those described in conjunction with the data management computing entity 65. Further, as shown in FIG. 3, the user computing entity 30 may include additional components and features. For example, the user computing entity 30 can include an antenna 312, a transmitter 304 (e.g., radio), a receiver 306 (e.g., radio), and a processing element 308 that provides signals to and receives signals from the transmitter 304 and receiver 306, respectively. The signals provided to and received from the transmitter 304 and the receiver 306, respectively, may include signaling information/data in accordance with an air interface standard of applicable wireless systems to communicate with various entities, such as a data management computing entity 65, another user computing entity 30, and/or the like. In this regard, the user computing entity 30 may be capable of operating with one or more air interface standards, communication protocols, modulation types, and access types. More particularly, the user computing entity 30 may operate in accordance with any of a number of wireless communication standards and protocols. In a particular embodiment, the user computing entity 30 may operate in accordance with multiple wireless communication standards and protocols, such as GPRS, UMTS, CDMA2000, 1×RTT, WCDMA, TD-SCDMA, LTE, E-UTRAN, EVDO, HSPA, HSDPA, Wi-Fi, WiMAX, UWB, IR protocols, Bluetooth protocols, USB protocols, and/or any other wireless protocol.

Via these communication standards and protocols, the user computing entity 30 can communicate with various other entities using concepts such as Unstructured Supplementary Service data (USSD), Short Message Service (SMS), Multimedia Messaging Service (MMS), Dual-Tone Multi-Frequency Signaling (DTMF), and/or Subscriber Identity Module Dialer (SIM dialer). The user computing entity 30 can also download changes, add-ons, and updates, for instance, to its firmware, software (e.g., including executable instructions, applications, program modules), and operating system.

According to one embodiment, the user computing entity 30 may include location determining aspects, devices, modules, functionalities, and/or similar words used herein interchangeably. For example, the user computing entity 30 may include outdoor positioning aspects, such as a location module adapted to acquire, for example, latitude, longitude, altitude, geocode, course, direction, heading, speed, UTC, date, and/or various other information/data. In one embodiment, the location module can acquire data, sometimes known as ephemeris data, by identifying the number of satellites in view and the relative positions of those satellites. The satellites may be a variety of different satellites, including LEO satellite systems, DOD satellite systems, the European Union Galileo positioning systems, the Chinese Compass navigation systems, Indian Regional Navigational satellite systems, and/or the like. Alternatively, the location information/data/data may be determined by triangulating the position in connection with a variety of other systems, including cellular towers, Wi-Fi access points, and/or the like. Similarly, the user computing entity 30 may include indoor positioning aspects, such as a location module adapted to acquire, for example, latitude, longitude, altitude, geocode, course, direction, heading, speed, time, date, and/or various other information/data. Some of the indoor aspects may use various position or location technologies including RFID tags, indoor beacons or transmitters, Wi-Fi access points, cellular towers, nearby computing devices (e.g., smartphones, laptops) and/or the like. For instance, such technologies may include iBeacons, Gimbal proximity beacons, BLE transmitters, Near Field Communication (NFC) transmitters, and/or the like. These indoor positioning aspects can be used in a variety of settings to determine the location of someone or something to within inches or centimeters.

The user computing entity 30 may also comprise a user interface comprising one or more user input/output interfaces (e.g., a display 316 and/or speaker/speaker driver coupled to a processing element 308 and a touch screen, keyboard, mouse, and/or microphone coupled to a processing element 308). For example, the user output interface may be configured to provide an application, browser, user interface, dashboard, webpage, and/or similar words used herein interchangeably executing on and/or accessible via the user computing entity 30 to cause display or audible presentation of information/data and for user interaction therewith via one or more user input interfaces. The user output interface may be updated dynamically from communication with the data management computing entity 65. The user input interface can comprise any of a number of devices allowing the user computing entity 30 to receive information/data, such as a keypad 318 (hard or soft), a touch display, voice/speech or motion interfaces, scanners, readers, or other input device. In embodiments including a keypad 318, the keypad 318 can include (or cause display of) the conventional numeric (0-9) and related keys (#, *), and other keys used for operating the user computing entity 30 and may include a full set of alphabetic keys or set of keys that may be activated to provide a full set of alphanumeric keys. In addition to providing input, the user input interface can be used, for example, to activate or deactivate certain functions, such as screen savers and/or sleep modes. Through such inputs the user computing entity 30 can collect information/data, user interaction/input, and/or the like.

The user computing entity 30 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, RRAM, SONOS, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. The volatile and non-volatile storage or memory can store databases, database instances, database management system entities, data, applications, programs, program modules, scripts, source code, object code, byte code, compiled code, interpreted code, machine code, executable instructions, and/or the like to implement the functions of the user computing entity 30.

c. Exemplary Networks

In one embodiment, the networks 135 may include, but are not limited to, any one or a combination of different types of suitable communications networks such as, for example, cable networks, public networks (e.g., the Internet), private networks (e.g., frame-relay networks), wireless networks, cellular networks, telephone networks (e.g., a public switched telephone network), or any other suitable private and/or public networks. Further, the networks 135 may have any suitable communication range associated therewith and may include, for example, global networks (e.g., the Internet), MANs, WANs, LANs, or PANs. In addition, the networks 135 may include any type of medium over which network traffic may be carried including, but not limited to, coaxial cable, twisted-pair wire, optical fiber, a hybrid fiber coaxial (HFC) medium, microwave terrestrial transceivers, radio frequency communication mediums, satellite communication mediums, or any combination thereof, as well as a variety of network devices and computing platforms provided by network providers or other entities.

IV. EXEMPLARY SYSTEM OPERATION

Details regarding various embodiments are described with respect to FIGS. 4-21 herein. As discussed herein, certain embodiments are configured to generate multi-level hierarchical episode-related data objects to reflect interrelated episodes of care (within a parent-episode-sub-episode relationship) so as to provide a complete view of various conditions and treatments provided to patients with appropriate indications of the inclusion of various episode-specific groupings so as to enable appropriate processing of claim records associated with sub-episodes, while maintaining associations between sub-episodes and parent episodes that may be indicative of additional complexities usable by downstream systems.

a. Overview

Embodiments as discussed herein are configured for generating hierarchical data objects reflecting various levels of treatment and/or interrelated conditions having corresponding treatments based on individually generated claim records reflecting discrete interactions between a patient and a provider, such as discrete office-visits, discrete interactions with providers during in-patient visits, discrete prescription pick-ups from a pharmacy, and/or the like. Through the usage of a network of reference data tables that may be utilized to update data stored within individual claim records, to generate unique data objects reflecting generated episodes and/or sub-episodes, to associate individual claim records with specific data objects relating to episodes and/or sub-episodes, and/or the like. In certain embodiments, systems and methods as discussed herein are configured for generating one or more temporary reference tables stored within a memory storage area for generated episode-specific data objects so as to enable generation of various sub-episodes relating to the episode data object to establish a hierarchical data object relating to the episode.

1. Technical Problem

Due to the discrete nature of claim records that are generated to reflect specific interactions between patients and providers, identifying associations between various claim records has been limited to single-level associations between claim records to group those claim records into episodes of care. However, these single-level associations often failed to provide a complete view of care provided to a patient, which may influence the operation of various down-stream systems, such as payment approval systems that utilize specific data indicative of conditions and treatments provided to patients for automated operation of approval mechanisms for initiating payment to various providers for treatment of specific conditions.

For certain circumstances, additional granularity beyond single-level episode of care grouping strategies may be necessary to provide a complete view of multiple conditions that may be impacting a particular patient, so as to provide relevant data regarding the inter-relationships between the multiple conditions that may be relevant for a patient. However, due at least in part to the volume of data relating to patients and/or episodes of care, existing computational systems and methods have been incapable of automatically generating multi-level, hierarchical data objects relating to particular episodes of care including sub-episodes of care may be separately viewable and/or may be separately retrievable.

2. Technical Solution

As discussed herein, various embodiments implement rules established with respect to generation of sub-episodes of care and which are implemented via a plurality of reference data tables that may be utilized together with executable processes of a grouper system (embodied as a data management computing entity or a module thereof) to generate temporary data tables encompassing episode-specific data usable for establishing sub-episodes for inclusion within those episodes. The episode-specific temporary data tables may establish various data reflected within claim records associated with the episode that is eligible for initiation of a sub-episode. The grouper systems and methods may be additionally configured to generate additional data to be associated with the episode so as to establish the hierarchical structure of the episode.

b. Core Grouping

FIG. 4 provides a general overview of processes involved in generating a core grouping of episodes. As reflected in Block 401, the data management computing entity 65 receives patient specific data records. Various embodiments are configured to process claims records corresponding to a single patient at a particular time, however other embodiments may be configured for intaking and processing data relating to a plurality of patients simultaneously. Claims data records are provided to the data management computing entity 65 from various sources, such as from individual provider-specific computing systems, from payer-specific computing systems, and/or the like. Each claim record comprises various data types that may be utilized to assign the claim record to an appropriate patient, and/or that may be utilized by the data management computing entity 65 to establish relationships between a plurality of claims data records for further processing and/or establishment of ETGs. Claims data records may each be embodied as individual data files comprising various individual data elements such as those reflected in Table 1, below. As illustrated, each data element may be reflected within a corresponding data field of the claim record. It should be understood that each claim may not comprise data populating all fields within a claim data record. For example, certain procedure-related claims data records may not encompass data within drug-related or lab-related data fields.

TABLE 1

| Field Name | Field Description |
| --- | --- |
| Family ID | Identifies familial relationships between patients (e.g., parents, siblings, etc.) by utilizing a unique family ID assigned to all members of a single family |
| Patient ID | Identifies individual patients, each patient has a corresponding unique patient ID that is not shared with other patients. |
| Amount Paid | The amount paid for this claim. |
| Amount Charged | The amount charged for this claim (e.g., by a provider) |
| Procedure Code | The procedure performed for this claim. For example, a CPT-4, HCPC, or NUBC revenue code. |
| Procedure Code Modifier | The procedure code modifier for this claim (if relevant) |
| Revenue Code | The NUBC revenue code. |
| ICD Code Type | A code that indicates the taxonomy utilized for providing diagnosis codes (e.g., ICD-9 or ICD-10) and/or the taxonomy utilized for providing procedure codes |
| First Diagnosis Code | Diagnosis codes (assigned utilizing the taxonomy identified above). The first code is required for |
| Second Diagnosis Code | ETG. These codes may include a decimal separator. |
| Third Diagnosis Code | |
| Fourth Diagnosis Code | |
| Fifth Diagnosis Code | |
| Sixth Diagnosis Code | |
| Seventh Diagnosis Code | |
| Eighth Diagnosis Code | |
| Ninth Diagnosis Code | |
| Tenth Diagnosis Code | |
| First Date of Service | The first and last date of service covered by this claim. |
| Last Date of Service | |

TABLE 1-continued

| Field Name | Field Description |
| --- | --- |
| Paid Date | The date this claim was paid. |
| Type of Service | The type of service performed for this claim. If the procedure code is blank, then this field is used to determine the record type. |
| Provider ID | A unique identifier assigned to the provider that performed the service. |
| Ordering Provider ID | A unique identifier assigned to the provider that ordered the service. |
| Provider Type | The type of provider who performed the service. User-defined input that is critical for assigning record types appropriately. This data may be provided as a uniform code assigned based at least in part on provider characteristics (e.g., provider accreditation) |
| NDC | National Drug Code. ETG maps this value to the Symmetry DCC (Drug Classification Code). |
| Day Supply | The number of days supply given for a drug. |
| Quantity Count | The quantity count dispensed for a drug. |
| LOINC | The Logical Observation Identifiers Names and Codes for a lab result. |
| Lab Test Result | The value of the lab result. |
| Place of Service | The place where the service was performed. |
| Unique Record ID | Unique identifier for each record. |
| Claim Number | Unique identifier for each claim. Claims can be broken out into multiple records. |
| Bill Type | A unique identifier of a particular claim data record. |
| Frequency Indicator | This data may be used to help build confinements. |
| Patient Status | A patient status indicator. This data may be used to help build confinements. |
| Facility Type | A facility type data value. This data may be used to help build confinements. |
| Bed Type | A bed type for a facility stay. This data may be used to help build confinements. |
| First ICD Procedure Code Second ICD Procedure Code Third ICD Procedure Code Fourth ICD Procedure Code Fifth ICD Procedure Code Sixth ICD Procedure Code Seventh ICD Procedure Code Eighth ICD Procedure Code Ninth ICD Procedure Code Tenth ICD Procedure Code | Standardized procedure codes. These may not be utilized by various embodiments, although other grouper configurations may utilize procedure codes for analysis. |

In certain embodiments, additional data retrieved from other data records may be used for various grouping-related processes. For example, data retrieved from member files may be utilized to indicate a patient's membership status with a payer-managed payment system, as well as additional biographical data regarding the patient. A member data file may comprise a plurality of data fields, such as those indicated in Table 2, below.

TABLE 2

| Field Name | Field Description |
| --- | --- |
| Family ID | Identifies familial relationships between patients (e.g., parents, siblings, etc.) by utilizing a unique family ID assigned to all members of a single family |
| Patient ID | Identifies individual patients, each patient has a corresponding unique patient ID that is not shared with other patients. |
| Gender | Patient gender. |

TABLE 2-continued

| Field Name | Field Description |
| --- | --- |
| Date of Birth | Used to compute age. |
| Member Beginning Eligibility Date | Indicates a date at which the patient became eligible for payment coverage. May be used to further limit the claims processed for a member. Also, used to determine if the member has the minimum required eligibility. |
| Member Ending Eligibility Date | Indicates a date at which the patient became ineligible for payment coverage. May be used to further limit the claims processed for a member. Also, used to determine if the member has the minimum required eligibility. |
| Line of Business | Describes whether this member is covered under a Commercial, Medicaid or Medicare plan and is used in severity weight selection. |

As another example of data that may be utilized for various processes of a data management computing entity 65 according to certain embodiments, a member term file may be utilized to provide further data indicative of payer-related coverage of a particular patient, in addition to data fields such as those suggested in Table 2, above, a member term file may comprise data fields indicative of specific medical and/or pharmaceutical coverage applicable to a particular patient. Accordingly, a patient may have a single related member file, but may comprise any number (e.g., zero or more) member term files, if relevant, indicative of changes in coverage of the patient over time. For example, a particular patient may be indicated as covered under a first medical coverage type for a first time period, and thus a first member term file may be provided indicative of the coverage during the first time period. The same patient's coverage reflected within the first member term file may have ended, and the patient may have been subject to a different medical coverage type during a second time period, as reflected within a second member term file.

These (and/or other) data files may be utilized for generating various episodes through processes as discussed herein. Various processes for episode generation may be utilized based upon assigned record types, which may dictate processes for generation of confinements and/or other anchor records that serve as building blocks of individual episodes. As discussed herein, each anchor record is utilized to establish a corresponding cluster, and episodes are built from one or more clinically related clusters.

Certain data management computing entity 65 configurations are provided for generating and/or grouping episodes in two phases. The first phase is a 365-day moving window of time that initially processes all of the anchor records. In certain embodiments, the data management computing entity 65 is configured to perform various record assignment processes based at least in part on diagnosis code classifications of various records. The data management computing entity 65 according to certain embodiments is configured to classify diagnosis codes identified within individual claim records into one of a plurality of classes based at least in part on rules-based classification engine mapping individual diagnosis codes to specific diagnosis classifications. These diagnosis classifications may encompass (1) specific codes, (2) non-specific codes, (3) sign & symptom codes, and (4) ignore codes. In various embodiments, the data management computing entity 65 may analyze specific and/or non-specific codes (e.g., to establish characteristics of an overall record) before evaluating sign & symptom and ignore codes, since these types of diagnosis codes are more definitive to ETG categories. Claims with sign & symptom codes are processed after this, when it is more likely that a more specific episode has already been created. By processing the sign & symptom diagnosis codes after the specific and non-specific diagnosis codes it minimizes opening vague, generic episodes.

In certain embodiments, additional criteria may be utilized for determining whether a particular diagnosis code is eligible for use in generating claim-record specific characteristics of an overall claim. For example, a procedure and/or revenue code within a claim record may be subject to criteria indicating that the procedure and/or revenue code must be eligible for the same ETG as one of the diagnosis codes stored within a particular claim record. The data management computing entity 65 may thus implement classification rules such that the ETG with the best match between the diagnosis codes and the procedure code (and/or revenue code) wins the associated cluster.

Moreover, based at least in part on the diagnosis code classifications of a particular claim record, the data management computing entity 65 may be configured to establish additional characteristics of the claim record and/or episodes generated based at least in part on the claim record. For example, if an episode is initialized based on a non-specific diagnosis code the episode may be characterized as a "virtual" episode. Virtual episodes may be utilized as placeholder episodes while waiting for a more specific episode with which it can merge. If another claim with a specific diagnosis is identified and is eligible to group to the virtual episode, it will become a real episode. Virtual episodes can merge into an existing open episode until the end of each grouping window. Once the software gets to the end of the yearlong moving window, any remaining virtual episodes will create non-specific episodes.

Sign & symptom diagnosis codes may be processed in reverse chronological order. Sign & symptom codes may be assigned a 60-day clean period before an episode. When the one-year moving window moves on to the next year, it does so with a minus 60-day window. When the system moves to the next year, it is looking at any ungrouped sign & symptom records to see if they are eligible to join an episode started in the next year of grouping. The 60 days left unprocessed at the end of a year assures that the next year's specific codes are grouped first and there are more eligible episodes to choose from when grouping sign & symptom records. Following this phase, the software moves to the next year moving window to group additional claims.

When the moving window moves to the next year (e.g., 365 days) of claim records, the data management computing entity 65 identifies and analyzes claim records that have not yet been grouped. It repeats the above process until all anchor claim records are grouped. After processing all anchor records for the member, the software merges together any non-specific episodes, merges any single cluster episodes, and assigns error ETGs to any inconsistent episodes.

After identifying and/or analyzing anchor records, the data management computing entity 65 processes the non-anchor claim records. First, it groups the ancillary records. The data management computing entity 65 first attempts to group the ancillary records to a confinement as detailed herein. In order to group to a confinement, ancillary record must be identified as being within the confinement's start and end dates and have a matching provider ID. If there is a valid match, the data management computing entity 65 looks to see if there is a valid match between the diagnosis code and procedure/revenue code with the confinement ETG. If there is a match, the ancillary claim is grouped to the confinement episode. If no match, the data management computing entity 65 assesses the specific and non-specific diagnosis codes and determines whether there is an episode to match the claim to. If nothing is found, the data management computing entity 65 will try to match on a sign & symptom diagnosis code.

Despite all efforts to assign every claim record to an ETG-based episode, there will be instances in which grouping of an ancillary record is not possible. These ungroupable ancillary records are known as "Orphan" records.

Lastly, pharmaceutical records are grouped. The data management computing entity 65 matches the claim record's Drug Classification Code (DCC) to an ETG. The data management computing entity 65 may be configured to implement a set of criteria to match the pharmaceutical record to an episode if there is more than one episode that the record can join.

During grouping, the data management computing entity 65 may be configured to merge and/or shift one or more episodes (e.g., as new claim records are generated). Therefore, the data management computing entity 65 does not generate intermediate outputs, and the data management computing entity 65 may thus only generate an output after all claims records have been processed. The data management computing entity 65 is configured to store (e.g., within a cache) an internal collection until all grouping is complete, and a finalization process computes the necessary post processing and calculations for the output files.

1. Record Types

With reference again to FIG. 4, the data management computing entity 65 first assigns a record type to each claim record when building an episode, as reflected at Block 402. The record type assigned to a claim is determined based on various criteria relating to specific data entries within a claim record, such as provider type, procedure code, procedure code modifiers, revenue codes (if applicable), service types (if applicable), NDC (if applicable), and/or the like.

Certain standardized data entries that may be utilized to populate data fields of a claim record are mapped to specific record types. Because certain claim records may encompass data entries having conflicting record type mappings (e.g., a provider type may map to a first record type and a procedure code may map to a second record type), the data management computing entity 65 is configured to implement a hierarchical assignment strategy (e.g., based on weights corresponding with standardized data entries) to identify a winning record type assignment. For example, a data field entry having a highest weight may be identified, and a record type assignment for the claim record may be assigned based on the record type mapped to the data field entry having the highest weight within the data record.

In certain embodiments, record types may be selected from a plurality of defined record types, such as facility, management, surgery, ancillary, and pharmaceutical records. It should be understood that these record types are purely examples, and the titles and number of these record types should not be taken as limiting. As discussed above, facility records are identified as claim records submitted by a treatment facility for room and board charges. Surgery records are claim records submitted by a provider for surgical or related procedures. Management records are claim records submitted by a provider relating to the evaluation of a patient's condition. Ancillary records are claim records submitted by a provider for laboratory, radiological, or similar services. Pharmaceutical records are claim records for prescription drug claims. Accordingly, because claim record types may be determined based at least in part on provider types, each provider is mapped to a particular provider type, such as "clinician" (providers who make diagnosis and recommend treatment. These providers may be individual physicians, physician's assistants, nurse practitioners, physical therapists, medical-related hospitals, physician offices, and/or the like); "facility" (tertiary providers such as short-term hospitals and psychiatric or chemical dependency facilities); "other/non-clinician" (all other healthcare providers); and/or the like.

Accordingly, the data management computing entity 65 may utilize data within the provider type field of a claim record to help identify anchor records and/or confinements (e.g., based on a determined mapping between the data within the provider type data field and a particular record type). As just one non-limiting example, the data management computing entity 65 may be configured to generate confinements for only certain provider types (e.g., "facility").

Moreover, in certain embodiments, the data management computing entity 65 is additionally configured to utilize a standardized listing of service types (e.g., which may be input directly into the type of service data, or which may be individually mapped through a look-up table from provider-specific service types to standardized service types. These service types may be assigned a lower weight for assigning record types than other data, such as procedure/revenue codes. Moreover, the data management computing entity 65 may be configured to map specific combinations of data, such as specific combinations of a standardized provider type and a standardized provider type to particular record types. Standardized service types may be selected from: (1) "Room and Board" (denoting a record is an inpatient record. Room and Board, together with a provider type of "Facility" indicates that a record is associated with a confinement), (2) "Med/Surg" (a medical or surgical service of some type. When combined with a provider type of "clinician" or "facility," this record may be indicated as an anchor record), (3) "Ancillary" (this type of service may be specified for all services not covered by "Room and Board" or "Med/Surg." This type of record is not eligible to open an episode).

In certain embodiments, the data management computing entity 65 is configured to utilize both procedure/revenue codes and service types in addition to clinician type data to determine an appropriate record type. The data management computing entity 65 may utilize a look-up table having entries for all available combinations of data record entries, with record types mapped to each available combination. However, as noted above, the data management computing entity 65 may additionally or alternatively store data utilized for implementing a hierarchical record type assignment weighting procedure, for example, if certain claim data record fields are empty. For claim records that do not contain service types or procedure/revenue codes (e.g., pharmacy codes), other claim data entries, such as a NDC code, may be utilized to assign a record type. Other data entries, such as procedure modifiers (e.g., which may comprise or may map to codes selected from a standardized listing of procedure modifiers) may change a record type in certain embodiments, and accordingly the data management computing entity 65 may be configured to determine whether a claim record includes data within any of these other data fields, and may determine whether a look-up table is stored for the combination of data within the particular claim record to establish a record type. It should be understood that other methodologies may be utilized in certain embodiments to establish claim data record types. The resulting output may be a separate data record that is associated with a particular claim record and that is indicative of the record type of the claim record. In other embodiments, the claim record may be modified by the data management computing entity 65, for example by adding an additional data field indicative of the claim record type that may be utilized for further processing.

2. Confinements

Block 403 indicates that the data management computing entity 65 may be configured to generate confinements for specific episodes. When building a confinement, the data management computing entity 65 utilizes the list of record types that are assigned as facility records. The data management computing entity 65 may be configured such that each facility record is automatically assigned a separate confinement. In other embodiments, the data management computing entity 65 may be configured such that facility records may be utilized to initialize a new confinement, or to join an existing confinement (e.g., based on various rule-based criteria for analyzing the contents of claims records and/or existing confinements). By default, the first facility record per patient starts a new confinement.

The data management computing entity 65 proceeds through the facility claim records and compares an existing confinement (if applicable) to the next claim record and checks to see if the next claim record is eligible to join the existing confinement. If not eligible, data management computing entity 65 ends/closes the existing confinement and initiates a new confinement corresponding to the record. By ending an existing/open confinement, data corresponding with the open confinement is updated to reflect an ending date/time of the confinement. Initializing a new confinement may comprise generating new data corresponding with the new confinement, including association of one or more claims records with the confinement (e.g., by generating a confinement identifier and updating the claim record to include the confinement identifier).

Criteria utilized by the data management computing entity 65 to enable a facility record to join an existing confinement may encompass criteria requiring that the claim record have the same Provider ID and the same Bed Type as the existing confinement, and the claim record must have a First Date of Service satisfying timing requirements relative to dates associated with the existing confinement for joining the existing confinement, such as a satisfying a maximum number of days between dates of service of multiple claim records.

Once the confinement has been built, such as by generating a confinement file or establishing a confinement identifier that may be stored in one or more claim records, additional information is collected from the claim records that will be used to calculate the output fields, and to group the confinement to an episode.

3. ETG Initialization

After the data management computing entity 65 has built confinements, it begins to group episodes as indicated at Block 404 of FIG. 4. Episodes are comprised of one or more clusters of clinically homogenous records. In certain embodiments, only certain record types are eligible to anchor a record to become an episode. For example, only claim records having one of the following record types may be utilized to establish an ETG as an anchor record: (1) management records; (2) surgery records; or (3) confinements (made up of facility records).

For management records and surgery records, all of the diagnosis codes (up to 10) that are on the claim are used to make grouping decisions. The order of the codes in the record is the least important tiebreaker. For grouping confinements, only the first diagnosis code is used to make the grouping decision.

Accordingly, the data management computing entity 65 identifies management records, surgery records, and confinements as anchor records. Each anchor record forms a cluster (with associated ancillary records, if relevant). Each cluster comprises one anchor record and zero, one, or more ancillary and pharmaceutical records. The exception is for confinements where all facility records utilized to establish a confinement are assigned to the same cluster. Further, each episode consists of one or more clusters.

In certain embodiments, claim records may be grouped to an episode based on certain data entries within the claim record, such as the diagnosis, revenue, and/or procedure codes of the claim record. The data management computing entity 65 may reference a lookup table mapping individual diagnosis codes, revenue codes, procedure codes, and/or the like to ETGs, thereby establishing valid groupings to specific episodes. Those valid groups each consist of only those claim record types (e.g., claim records having specified diagnosis codes, revenue codes, procedure codes, drug codes, and/or the like) indicated as eligible for joining a common episode indicated as relevant to a particular ETG. As each episode is ultimately assigned an ETG, the claim records to be assigned to an episode must be eligible for association with the ETG of the episode. If the eligibility of a particular claim record matches the ETG assigned to an existing episode, the record is assigned to it. Otherwise a new episode is started. As mentioned above, an operating instance of the data management computing entity 65 executes for a single patient at a time and processes the anchor records with a 365-day moving window. This is done so that the data management computing entity 65 processes the more specific codes first, leaving the sign & symptom codes until later, when it is more likely that there is a more specific episode for these claims to join.

The data management computing entity 65 may be configured to heavily weight diagnosis codes to identify discrete episodes. The diagnosis code(s) of a claim record identifies the condition(s) being treated, which broadly translates to one of a standardized listing of ETGs. Each diagnosis code may be identified with a given diagnosis class. There are four diagnosis classes as discussed herein: specific, non-specific, sign & symptom, and ignore. The data management computing entity 65 processes the specific codes first when grouping. Also, the non-specific codes are treated as if they are specific when the software is performing the initial grouping. The sign & symptom diagnosis codes are held for grouping until the end of the year-long moving window to let all of the more specific (and non-specific) diagnosis codes group first.

In certain embodiments, the data management computing entity 65 assigns diagnosis code to an eligibility set. The diagnosis eligibility set is then matched and ranked with one or more ETGs through a diagnosis eligibility set eligibility table. The rank values are as follows: low, medium, high, severity, and primary. Low, medium, and high are the strength of the match association. Severity ranks indicate that the diagnosis eligibility set is valid for that ETG, and that it can shift the ETG. The data management computing entity 65 may be configured to assign a rank of "severity" when a diagnosis eligibility set will shift an ETG value. A primary rank describes conditions that define a disease and are the main codes that impact grouping decisions.

In building episodes, the procedure or revenue code helps to identify the ETGs to which a particular claim record can be assigned. When a procedure code and a revenue code are both present on a claim, the data management computing entity 65 uses the code which has the highest record type hierarchy 'rank' to drive record grouping. If there is a tie in rank between the procedure code and the revenue code the procedure code takes precedence over the revenue code and is utilized to determine record grouping.

A given procedure may be valid for several ETGs, though not equally so. A stored eligibility table utilized by the data management computing entity 65 therefore ranks the valid ETGs for each procedure to give a better sense of how closely related the service is to each ETG. The ranking is Very Low, Low, Medium, and High, with High being the strongest rank.

Because of the varying coding practices in use by different providers and the many ways of preparing records for the data management computing entity 65, the diagnosis codes on a claim record may be valid but unrelated. For example, an anchor record may have one diagnosis for a fracture and another for asthma. These are separate conditions for which the member is being treated. A claim record can only be assigned to one episode, but there are clearly two episodes that are active. Future claims may be submitted for either or both conditions. An anchor record is assigned to an episode according to the best combination of procedure/revenue and diagnosis code—the combination it can be most sure of.

Once the anchor record has been assigned to an episode, the other diagnosis codes on the record are examined. If a diagnosis code would more appropriately belong to a different episode, the software starts a "phantom" cluster in that episode. If the cluster is not appropriate for any existing episode, a new episode is started with the phantom cluster. Claim records that follow this anchor record will now have additional episodes available to them, so the data management computing entity 65 is capable of assigning them more accurately than it would without using phantoms. This allows the diagnostic information to be utilized fully to identify and track all of the conditions for which the patient is being treated, yet still assign records to one and only one episode.

Causing a claim record to join/merge with an existing episode, or to cause the claim record to generate a new claim record, the data management computing entity 65 utilizes logic indicative of direct and valid ETG lists for specific episodes. The direct ETG list encompasses a listing of all ETGs that have been identified as active for the episode. The valid ETG list encompasses a listing of the potential ETGs that might be active within the episode (potential to look for while grouping).

The data management computing entity 65 uses the plurality of diagnosis codes on a claim record as well as the procedure and/or revenue codes. The data management computing entity 65 looks up the eligibility for the codes on the respective eligibility tables and prepares a direct and valid list of all the matches. The ETG that the diagnosis code is primary for is added to the episode's direct list.

When an ETG is added to the direct list, the software checks the CPT-4, HCPCS, and ICD-9 procedure code on facility records (ICD-10 codes to be added at a later date), and diagnosis codes of the responsible claim record (or the diagnosis only, if this is a phantom). If any of the codes can shift an ETG to the new direct ETG, then that ETG is added to the valid list. For example, if a direct ETG has 2 ETGs that can shift to it, but the claim record adding the direct ETG can shift only one of those two (based on diagnosis/procedure code eligibility), then the software will add only the shiftable ETG to the valid list.

To be eligible to join an existing episode, the diagnosis eligibility set associated with a record's diagnosis code must be eligible (in any way) for an ETG on the episode's direct list or primary to an ETG on the episode's valid list. When a claim record joins an episode, it "promotes" ETGs from the valid list to the direct list if the diagnosis eligibility set is primary to any ETG on the valid list.

Once it is established that a record can join an episode based on the diagnosis and procedure codes, the data management computing entity 65 then looks at the date range of the episode to see if it is eligible. An important aspect of building episodes is the ability to differentiate between multiple instances of the same condition. ETGs accomplish this by identifying discrete dynamic clean periods. A clean period is defined as the absence of treatment for a specified period of time. Each ETG has its own unique clean period. Further, the clean period is dynamic in that each new anchor record resets the clean period back to zero. In this way, as long as a condition is consistently treated such that each successive anchor record is less than or equal to the clean period for the ETG, the episode can last forever. The clean period only needs to overlap-it does not need to be totally within the record's dates.

The mechanism for merging episodes together may operate based on the ETGs. For a single claim record, the data management computing entity 65 makes a determination of episode merging based on data within the claim record alone. But for an episode to merge, the data management computing entity 65 analyzes the valid and direct list of ETGs and verifies that if a first episode is trying to merge into a second episode, the second episode's direct and valid lists incorporate the ETG from the first episode's list. Once the data management computing entity 65 determines that the first and second episode can merge based on dates and ETGs, the data management computing entity 65 extends the dates forward and back, based on either episode. The valid and direct lists of both original episodes are appended together.

After a merge, the data management computing entity 65 checks each new diagnosis eligibility set of the episode for shifting, looking to see if an ETG can be promoted from the valid list to the direct list. When a claim record merges into an existing open episode, the data management computing entity 65 checks each of the claim's associations to an ETG within the merging record. It checks to see if any of those associations would cause the existing ETG to shift.

While merging is two episodes coming together, shifting changes the nature of an ETG. Shifting can occur based on the diagnosis and procedure codes or a merging episode. After a shift, the data management computing entity 65 checks merging again. This is check may be performed periodically until no further shifts are necessitated.

For every diagnosis code on the claim record, the data management computing entity 65 first searches for a match of the relevant diagnosis eligibility set to existing episodes. For the diagnosis eligibility sets for all specific and non-specific codes, the data management computing entity 65 starts the lists of all of the matches along with the ranking of matches with procedure/revenue codes. For example, if a record has 4 diagnosis codes, the data management computing entity 65 will process the diagnosis eligibility sets for all of the specific and non-specific diagnosis codes first. Once these group, the data management computing entity 65 checks to see if the other eligibility sets for diagnosis codes on the record can group to this same episode. If they do, the data management computing entity 65 does not do anything else with these diagnosis eligibility sets.

The sign and symptom diagnosis codes that do not group to the same episode are flagged to a 'Regroup Records' list for later regrouping. The record is flagged to show that it has already grouped and the record's dollars (costs) have already been assigned. The remainder of the record is held until the software assigns sign & symptom records later.

When starting a new episode, the data management computing entity 65 repeats the process described above. The data management computing entity 65 looks at the primary ETGs for the diagnosis eligibility sets associated with all specific and non-specific diagnosis codes and ranks those ETGs based on the procedure code.

At this point, the data management computing entity 65 has either joined a claim line to an episode, started a new episode, or is holding the claim on the Regroup Records list. If a new episode is started from a non-specific code, it will start a "virtual episode". The data management computing entity 65 is configured to temporarily store virtual episodes (e.g., in a cache) to determine if any later-generated episodes are generated that the virtual episode can merge with. If later-generated episodes are created that are eligible for merging with the virtual episode, the data management computing entity 65 merges these episodes as indicated. The data management computing entity 65 merges these virtual episodes based on the record, not based on the episode information.

Many times a claim record will be eligible to group to more than one existing episode. For each episode that a claim record is eligible to join, the data management computing entity 65 first chooses the highest ranked ETG from the direct ETG list. If there is not a direct ETG available, it will choose the highest ranked ETG from the valid ETG list.

If there is more than one match, there a generic matching process may be implemented to identify a final match for merging. It is the same process that is used for every type of record to match to a list of ETGs. The matching process may run several times for the same claim record. The data management computing entity 65 may then select the episode with the highest match based on priority rules.

4. Episode Population

After the data management computing entity 65 has completed the anchor record grouping, the process of grouping ancillary records begins as indicated at Block 405 of FIG. 4. Ancillary record grouping comprises a process of grouping records with a specific record type and encompasses processes for assigning the record to a confinement and assigning the record to an episode.

The data management computing entity 65 assigns an ancillary record to a confinement when the ancillary record is within the same timeframe as the confinement. When there are multiple confinements that a record could be assigned to, the data management computing entity 65 checks the confinements in reverse chronological order and assigns the record to the first confinement that matches the ancillary record's specific and non-specific diagnosis codes. If none, the data management computing entity 65 checks the confinements again for matches with the record's sign and symptom diagnosis codes. If the ancillary record cannot match on any of these criteria, it is assigned to the first confinement that encompasses its dates (the data management computing entity 65 is still checking the confinements in reverse chronological order).

Before grouping an ancillary record normally, the data management computing entity 65 first checks to see if the record is assigned to a confinement. If the record's provider ID also matches the provider ID of the confinement, then the data management computing entity 65 assigns the record to the confinement's episode if the record is at all valid for that episode.

To assign an ancillary record to an episode, the data management computing entity 65 identifies episodes for assignment of an ancillary record by the ancillary record's diagnosis codes and procedure/revenue codes. The data management computing entity 65 first evaluates diagnosis codes classified as specific to determine if the ancillary record can join to an episode. It then evaluates diagnosis codes classified as sign and symptoms to determine if it can join to an episode. The ancillary record must occur within the ETG's clean period in order to be eligible to group to an existing episode. An ancillary record can shift an episode's ETG assignment, but it cannot extend an episode's length.

An ancillary record that cannot join an open episode is then evaluated to determine if it can be assigned to a preventive ETG. If an ancillary record cannot be assigned to a preventive ETG, it is then evaluated to determine if it can be assigned to a valid ETG for which the diagnosis code is Primary. If so, it uses that ETG, but it has an episode type of 9 to indicate that it is an orphan ancillary. If an ancillary record cannot be assigned to a valid ETG, it is assigned as an orphan record.

After anchor record grouping and ancillary record grouping have completed, the data management computing entity 65 is configured to group drug records to episodes. Drug record grouping comprises a process for grouping pharmacy claim records with a National Drug Code (NDC) and medical claim records with an assigned Drug Class Code (DCC).

A valid drug record contains a valid DCC code for eligibility to join to an episode. A drug record cannot shift an episode's ETG assignment or extend an episode's length; it can only join an existing episode.

For a drug to be eligible to join an episode, it must occur within the episode's drug clean periods. Each ETG has its own drug clean periods-a pre-clean period that is used prior to an episode's dates and a clean period that is used after an episode's dates. For chronic episodes, such as diabetes, the post-clean period is ignored. This allows drugs that are sometimes used for maintenance purposes to join to an existing episode and not be assigned as Ungroupable. Acute episodes, such as Otitis media (ear infection), have short drug clean periods due to their episodic nature (such as 30 or 90 days). The drugs are prescribed to alleviate the condition and when health has been restored, drugs are no longer necessary.

A drug record that cannot join an open episode is then evaluated to determine if it can be assigned to a prescription ETG. Prescription ETGs for drug records are ongoing pharmaceutical treatment without provider intervention. If a drug record cannot be assigned to a prescription ETG, it is then assigned as an orphan drug record.

Drug record grouping occurs at the DCC level. Each DCC is associated with an appropriate ETG based on a ranking system. As the rank value increases the strength of association is weaker. This allows for drugs with various uses to be evaluated as to which open episode it can best join to. For example, the drug Lexapro is an antidepressant and is mainly used to treat anxiety. It can also be used to treat neuropathic pain. It has a low rank value for the mental health ETGs and a high rank value for diabetes. If there are two open episodes, a mental health episode and a diabetes episode, the Lexapro drug record-which occurs on a date where it could join to either episode-would group to the mental health episode because the strength of association is stronger. If only a diabetes episode is open, the Lexapro drug record would group to that episode.

After grouping ancillary records and drug records to existing episodes, the data management computing entity 65 may be configured to define chronic episodes and subdivide those chronic episodes into yearly episodes (or episodes defined by other time periods). The data management computing entity 65 reviews chronic episodes individually. The process occurs at the end of a grouping process, prior to episode finalization.

After parsing a chronic episode, the data management computing entity 65 reviews each annual episode (or the entirety of the episode if the data management computing entity 65 is configured to accept unlimited length episodes). The data management computing entity 65 then recreates the episode's direct list using the anchor records by checking to determine if any of the anchor records belong to the same chronic group. The data management computing entity 65 then identifies those episodes belonging to a shared chronic group (e.g., identified via unique identifiers temporarily stored in association with episodes; those episodes having the same unique identifier are indicated as being a part of the same group). For those anchor records indicated as being associated with a shared group, the data management computing entity 65 executed specified logic to assign a winning anchor record (having a corresponding ETG that is attributable to the chronic episode).

Only episodes with an ETG flagged as chronic are processed through the foregoing logic. A chronic episode goes through the episode building process as usual (referred to herein as processes for generation of the underlying episode). Generation of chronic episodes may proceed without reference to the eligibility rules and one entire episode is created for the chronic condition. Chronic episodes are then parsed into multiple, annual episodes based on the selection made in the configuration. Based on that selection, the data management computing entity 65 divides the one entire episode into annual episodes using the dates from the user's selection. The data management computing entity 65 uses the user-selected date and looks forward or back 365 days, collects all anchor records within that timeframe and assigns them to a new episode. The patient's eligibility is then used, and the dates within the episode are further modified based on the patient's beginning and ending eligibility dates.

As the data management computing entity 65 creates the underlying episode, it remembers the ETG shifting assignments. For example, an episode may start as an ETG for Coronary Artery Disease and then shift to an ETG for Congestive Heart Failure as it is building. When it parses out the episode, it may assign the first year to the CAD ETG and the second year to the CHF ETG.

In addition to the episode start and end date, two additional date fields are populated on the Summary output for chronic episodes that indicate the first anchor date and the last anchor date within the episode. For non-chronic conditions, these dates are blank.

The result of this process is annual episodes for chronic ETGs.

c. Episode Finalization

After the core grouping processes have completed, the data management computing entity 65 begins execution of the episode finalization processes. The episode finalization processes provide additional information to be appended to the episodes so that they are ready for output. In certain embodiments, the episode finalization process involves one or more of the following: assignment of an episode type to the episode; assignment of the full ETG number to the episode; creation of the additional output files for the episode identifying complications, comorbidities, treatment indicators, and shifted ETGs; assignment of a responsible provider to the episode; determination of the episode's outlier status, and assignment of a severity score and severity level to the episode.

1. Episode Type

During episode finalization, the data management computing entity 65 may be configured to assign an episode type, indicative of the completeness of an episode as shown at Block 406 of FIG. 4. Each episode is assessed for its status as a full year episode, and if the episode has a clean start and/or a clean finish. The episode's start and end dates are compared against either the clean period days or the opening/closing days. From this information, the episode type can be determined.

User Episode Type values are also determined if custom clean period data are provided as input into the data management computing entity 65. The same process is followed as for the Episode Type processing.

The Incomplete Reason field identifies the reason the episode was flagged as incomplete. All complete episodes will have the Incomplete Reason field blank/NULL, whereas incomplete episodes will have the value 0 (due to service dates) or 1 (due to eligibility dates).

2. Treatment Indicators

Moreover, the data management computing entity 65 may evaluate each episode to determine if the episode contains any treatment indicators as indicated at Block 407 of FIG. 4. Similar processes may be utilized for determining whether any sub-episodes contain any indicators of treatment indicators.

The determination of the presence of treatment indicators is performed by first evaluating procedure codes, revenue codes, and/or DCCs for non-facility claims and all procedure codes for facility claims against lookup tables to determine if there is a match. Those lookup tables associate particular codes (as indicated above) with corresponding treatment indicators having corresponding treatment indicator codes. Upon the identification of a match within a respective lookup table, the episode records are tagged with the treatment indicator codes. An output indicative of the episode identifier and the treatment indicator may be generated for consumption by additional processes.

3. Condition Status

Complications associated with an episode are reflected within an episode condition status output, which contains the episode number and a condition status code determined to be applicable to the episode.

Complications may be based on diagnosis codes and can cross episodes. For example, an anchor record for a diagnosis code of CAD and a secondary diagnosis of diabetic coma which was grouped to a CAD episode (real episode) can be considered a complication of a diabetes episode (phantom episode).

The data management computing entity 65 is configured to categorize complications into groups; complications of a similar clinical nature are assigned to the same Condition Status group. A Condition Status group contains a priority that is used to determine what Condition Status code takes precedence and how many to include in the output. A Condition Status group with multiple unique priority values indicates that one Condition Status code takes precedence over the others. A Condition Status group with multiple identical priority values indicates that the complications are all considered equal. A Condition Status group with multiple identical priority values that are flagged as competing indicates that the complications are all considered equal but only one of the Condition Status codes will take priority over the others.

Each anchor record is evaluated to determine if it contains any diagnosis codes classified as a complication. The diagnosis codes are evaluated against a set of lookup tables for a match. If there is a match, that record is tagged with the corresponding Condition Status code. Each episode is evaluated to determine if it can be assigned a Condition Status code. Such an evaluation may encompass a process by which the anchor records tagged with a Condition Status code are matched against a lookup table for a Target ETG (the ETG to which the Condition Status code is eligible to be associated), and the episode's ETG is matched against the same lookup table for a match on Target ETG.

When an episode has an ETG that the Condition Status code is eligible to be matched with, the Condition Status code(s) is assigned to that episode.

Once the data management computing entity 65 has tagged all of the episodes with Condition Status code(s), the data management computing entity 65 determines how many of those codes to include in the output. When there are multiple Condition Status codes within an episode, logic is necessary to determine what Condition Status codes to output.

All Condition Status codes are output when they have multiple distinct Condition Status group values or when they have duplicate Condition Status group values for which the priority values are duplicates and the Compete flag is blank.

Only one Condition Status code is output when Condition Status codes have duplicate Condition Status group values: the Condition Status code with the most number of clusters (or cluster cost, if a tie) is output when the Compete flag indicates a competing value; or the Condition Status code with the lowest priority value is output when the Compete flag is blank and the priority values are different.

4. Comorbidities

Comorbidities associated with an episode are an available output for users. This output contains the Episode Number and the Comorbidity Code.

Comorbidity is defined as the presence of more than one disease or health condition in an individual at a given time. Comorbidities may be based on diagnosis codes. Comorbidities can cross episodes.

Each anchor record for a patient is evaluated to determine if it is classified as comorbidity. This is accomplished by matching the diagnosis codes against a set of lookup tables. If there is a match, information from that anchor record is added to the Patient Comorbidity Information. The data management computing entity 65 keeps track of all of a patient's comorbidities and adds a newly-found comorbidity to it. These comorbidities have a time window for when they are considered active.

Once the data management computing entity 65 has identified and updated the patient comorbidity information, the data management computing entity 65 uses that information to determine what episodes can be assigned with a comorbidity code. All of a patient's episodes are evaluated; if any comorbidity from the patient comorbidity information has dates that overlap with an episode's dates, and if that episode's ETG assignment is mapped to the comorbidity code, then the episode is tagged with the comorbidity code.

Comorbidities are categorized into groups. This allows the capability and flexibility to output all comorbidities, or just one comorbidity, for an episode. Comorbidities of a similar clinical nature are assigned to the same group. A comorbid group contains a priority that is used to determine what comorbid code takes precedence and how many to include in the output. A comorbid group with multiple unique priority values indicates that one comorbid code takes precedence over the others. A comorbid group with multiple identical priority values indicates that the comorbidities are all considered equal. A comorbid group with multiple identical priority values that are flagged as competing indicates that the comorbidities are all considered equal but only one of the comorbid codes will take priority over the others.

Once the data management computing entity 65 has assigned comorbidity codes to a patient's episodes, it then determines how many of those comorbid codes to include in the output. When there are multiple comorbid codes within an episode, logic is necessary to determine what comorbid codes to output.

All comorbid codes are output when an episode has multiple distinct comorbid group values or when an episode has duplicate comorbid group values for which the priority values are duplicates and the Compete flag is blank Only one comorbid code is output when an episode has duplicate comorbid group values: the comorbid code with the most number of clusters (or cluster cost, if a tie) is output when the Compete flag is C; or the comorbid code with the lowest priority value is output when the Compete flag is blank and the priority values are different.

5. Track ETGs

During grouping, the data management computing entity 65 keeps track of the list of ETGs that an episode goes through during its life. The Direct ETG List is all ETGs that have been clearly identified as active for the episode, while the Valid ETG List is all ETGs that might be active within the episode. As more claims group to an episode or as episodes merge together, this Direct ETG list grows as some of the Valid ETGs are promoted to the Direct ETGs. For more information on this process, refer to the Anchor Record Grouping functional specification.

A list of episodes and all of the ETGs they shifted from will now be an available output file for users. This new output, called Episode ETG, contains the Episode Number and the ETG Base Class Number.

6. Assigning Responsible Provider to an Episode

The data management computing entity 65 assigns a Responsible Provider to an episode as indicated at Block 408 of FIG. 4 by summarizing each provider's management and surgery records within the episode. The Provider ID with the highest allowed amounts is assigned as the Responsible Provider. Upon assigning the responsible provider to an episode, the data management computing entity 65 updates a data object generated for the episode to reflect the responsible provider.

7. Assigning ETG Numbers to Episodes

An ETG number for an episode is generated and assigned as indicated at Block 409 of FIG. 4 based at least in part on a retrieved number corresponding with a relevant ETG base class identified as relevant to the episode. For example, an extended unique identifier may be generated for the specific episode, encompassing an ETG base class identifier with an episode specific identifier appended thereto. During grouping, the ETG base class has been identified. After processing an episode through the complication, comorbidity, and treatment indicators logic, the data management computing entity 65 assigns the episode with its full ETG number.

For example, the unique identifier may comprise a plurality of single-digit values each provided as an indicator of determined characteristics of the specific episode. For example, a first single digit indicator may be a complication code indicator. Upon determining that a complication code assigned to the episode satisfies a criteria (e.g., the complication code of an episode has a specified value), the unique identifier may be assigned a determined value (e.g., a "1"). Upon determining that the complication code does not satisfy the criteria, the unique identifier may be assigned a different determined value (e.g., a "0"). It should be understood that various criteria may be implemented to assign various corresponding unique values to the full ETG number.

In certain embodiments, a second single digit indicator may be a comorbidity indicator, and the data management computing entity 65 may be configured to assign values to the comorbidity indicator based at least in part on comorbidity indicator criteria and the contents of the episode.

A third single digit indicator may be a treatment code indicator providing an indication of certain treatment code data within the episode. For example, based at least in part on the presence of various treatment code indications, the data management computing entity 65 may utilize a lookup code to determine a relevant single-digit indicator for assignment to the ETG code based on the combination of treatment indicators present within the episode.

It should be understood that other indicators may be generated and/or appended to the ETG code for a particular episode. The resulting ETG code for a particular episode provides an indication of a particular condition and/or procedure represented by the episode, together with indications of various modifications of the condition and/or procedure, such as the presence of complications, comorbidities, treatment indicators, and/or the like. As just one example, a full ETG number of "163000010" may be assigned to an episode, with the leading 6 digits (163000) being the ETG base class corresponding with Diabetes. The 7th digit (0) indicates no complications are present, the 8th digit (1) indicates that a comorbidity is present, and the 9th digit (0) indicates that no treatment indicators are present. Thus, the entire 9-digit code may be translated to refer to a Diabetes episode without complications, with comorbidities, and without treatment indicators.

8. Severity Adjustment

The data management computing entity 65 is configured to generate a severity score and/or a severity level for each episode, for example, by extracting weights associated with a patient's demographics, the episode's condition statuses, the episode's comorbidities, and/or the like. Those weights may be assigned by the data management computing entity 65 relative to data stored within a patient profile, within an episode, and/or the like. These weights may be summarized to produce the severity score, which may be utilized to lookup a severity level (e.g., by comparing the severity score against thresholded severity score levels each corresponding with particular severity levels).

The data management computing entity 65 initially identifies whether the episode's ETG is severity adjusted. The data management computing entity 65 identifies ETGs that are severity adjusted based on data table entries identifying severity levels for specific episodes. The presence of an ETG in such a data table indicates that an episode with that ETG is subject to severity adjustment logic. An episode with an ETG not present in this table is not subject to severity adjustment logic and immediately is assigned a severity score of 1.000 and severity level of 1.

The data management computing entity 65 may be configured for implementing additional criteria for applying severity adjustments. For example, the severity adjustments may only be applicable for episodes relating to patients satisfying certain criteria (e.g., age, plan type, and/or the like). Those episodes not satisfying the applicable criteria may be assigned a Severity Score of 1.000 and a Severity Level of 1 and a Severity Error=2 by default.

The patient's age, gender (currently assigned to the episode), LOB, and the episode's ETG may be used to derive the demographic weight to add to the episode. If the patient's age or gender are invalid values, the data management computing entity 65 assigns an error to the episode (Severity Error Status=1) and that episode is no longer processed through severity adjustment logic. An invalid age is defined as the value 999 and an invalid gender is a value not M and not F.

Condition status codes are assigned to an episode during the condition status logic processing. Those codes are then assessed to determine if they contribute to an episode's severity. All condition status codes assigned to an episode are evaluated against the eligibility tables, which may comprise data indicative of a severity priority hierarchy to be implemented in the event of conflicting priority values.

Comorbidity codes are assigned to an episode during the comorbidity logic processing. Those codes are then assessed to determine if they contribute to an episode's severity. This logic is analogous to that provided for condition status codes.

All weights added to the episode are then summarized to derive the final score for the episode. If the final severity score results in a number less than the value 0.1000, the data management computing entity 65 resets the severity score to the value 0.1000. There is the potential for a severity score to be a negative number, as some of the weights can be a negative value.

After the severity score is computed, the data management computing entity 65 assigns the severity level to the episode based on a lookup table entry, as discussed herein.

9. Medically Questionable Flag

Processing medically questionable flags involves analyzing data stored within episode-specific data files to determine if the episode is incongruent with the member's gender (for example, males with 602400 pregnancy) or age (for example, pregnancy episodes in children). Conceptually, the medically questionable flag is designed to flag those episodes where the outcome defies medical probability suggesting a strong likelihood of either a grouping anomaly, data input error or highly atypical clinical scenario.

For example, an episode is determined to be gender incongruent when the base ETG includes a gender limitation and the member's gender from the summary file does not match the genderCongruent value for that episode's base ETG. An episode is determined to be age incongruent if there is a lower and upper age limitation for the base ETG and the member's age at the start of the episode from the summary file is lower than the ageLowerLimit or higher than the ageUpperLimit values for that episode's base ETG.

10. Sub-Episodes

As discussed herein, sub-episodes are defined as medically meaningful episodes of care relating to services (and/or items, such as medication, devices, and/or the like) provided for a clinical event that is fully contained within a time period associated with an episode (referred to herein as a "parent episode" to distinguish between episodes being a largest level of organization and a sub-episode encompassed within the parent episode). Sub-episodes are generated at least in part by transforming single-layer, flat-episodes into multi-layer hierarchical data objects generated for reflecting a hierarchical relationship between various episodes and included sub-episodes. Such a hierarchical relationship enables sub-episodes and corresponding data objects or portions of episode-specific data objects to be reflective of a variety of characteristics of the sub-episode that may be distinct from analogous characteristics of an including parent-episode, while maintaining a structured hierarchical relationship that may itself be reflective of complexities associated with treatment of conditions relevant to the parent-episode and the sub-episode.

FIG. 5 provides a general overview flowchart of sub-episode generation and processing steps, with FIGS. 6-21 providing additional detail regarding each step indicated in FIG. 5. Generation of sub-episodes for inclusion within episodes proceeds after initial processes for generation of episodes. Because data within episode-specific data objects may change while the data management computing entity 65 proceeds through the series of steps associated with generation of an episode, the episode-specific data objects are stored within temporary storage areas upon completion of interim processing steps for generation of complete and finalized episodes of care, thereby enabling the initiation of processing steps performed by the data management computing entity 65 that are based on the presence of previously generated episode-specific data objects for execution. As indicated in FIG. 5, the data management computing entity 65 proceeds to process one episode at a time, to examine each ETG episode summary record of an episode-specific data object to determine if the ETG on the record or any ETGs on the direct list for that episode are eligible for a sub-episode, as indicated at Block 501.

When determining whether a particular episode is eligible for sub-episode treatment, the data management computing entity 65 utilizes a reference table listing those ETGs with eligibility for a sub-episode. Analysis of episodes for eligibility for supporting one or more sub-episodes may be limited to episodes of a designated episode type (e.g., surgery or medical) and/or being associated with a particular provider type. Accordingly, the process of certain embodiments continues for those ETG anchor records for the episode which have a record type of management or surgery in combination with a provider type of clinician. Episodes that do not include anchor records satisfying initial criteria for generation of sub-episodes may be finalized for storage in a permanent, non-transitory memory storage area without further processing. As discussed in greater detail herein, sub-episode eligibility may be determined based at least in part on diagnostic-code eligibility (e.g., only anchor records having one of a specified listing of diagnostic codes may be eligible for sub-episodes), provider type eligibility (e.g., only anchor records associated with a provider having one of a defined listing of provider types may be eligible for sub-episodes), and/or the like. Accordingly, it should be understood that sub-episode eligibility may be based on any of a variety of eligibility characteristics of an anchor record.

Figure 6:
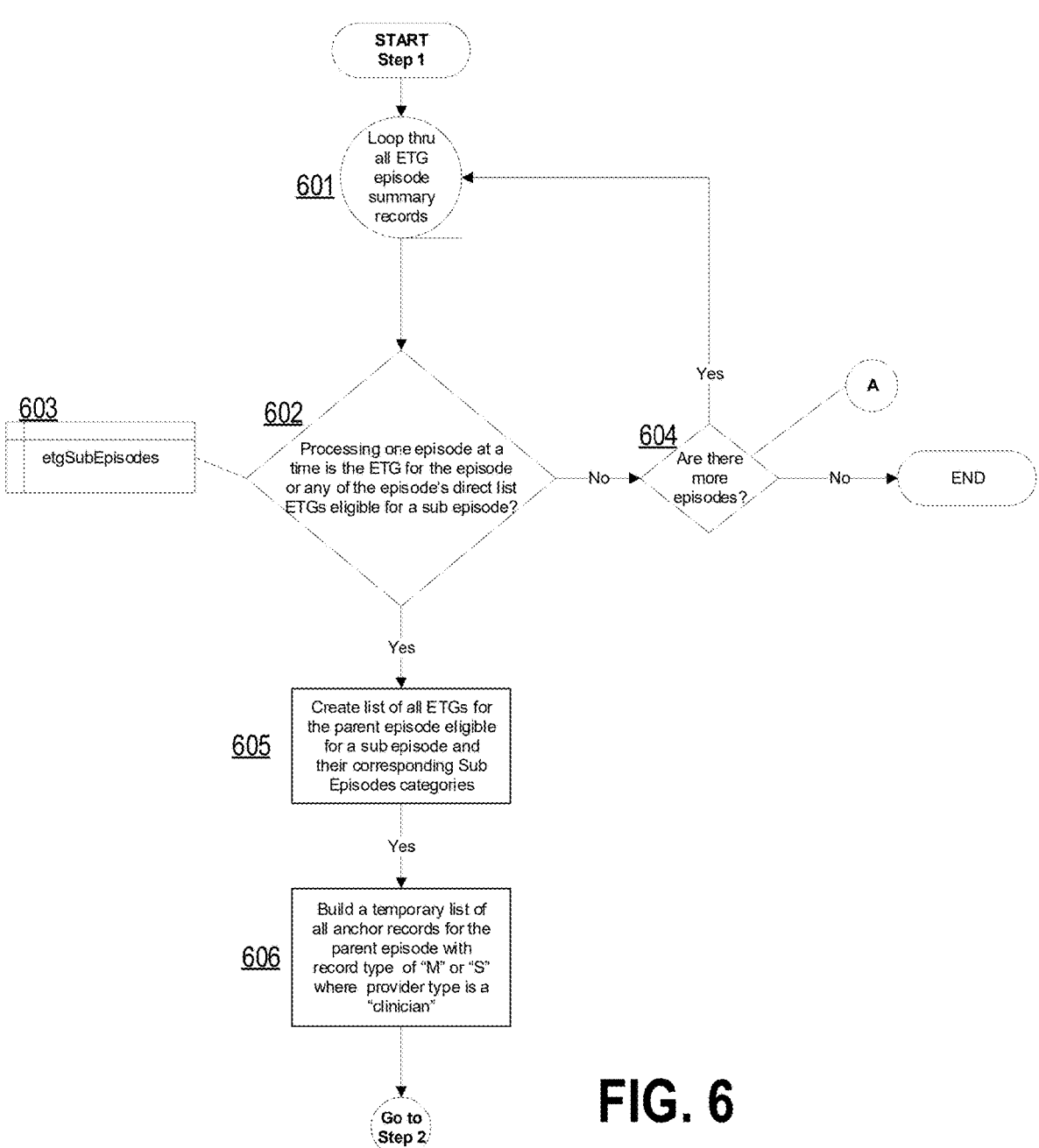
FIGS. 6-21 are additional flowcharts providing detailed illustrations of steps associated with generation of sub-episodes in accordance with certain embodiments.

FIG. 6 provides additional detail regarding the process for determining whether an episode is eligible for sub-episode treatment. As illustrated at Blocks 601-602, the data management computing entity 65 of certain embodiments is configured to loop through generated episode summary data records of episode-specific data objects, such that the data management computing entity 65 examines each episode individually for sub-episode eligibility and generation. In building sub-episodes, each of the plurality of diagnosis codes on the anchor record will be examined to determine if that diagnosis code can initiate a sub-episode (e.g., based at least in part on sub-episode eligibility data tables, as represented by Block 603). In certain embodiments, a sub-episode eligibility data table may comprise a plurality of data entries defining various characteristics and/or eligibility data for certain ETGs, as well as ETG identifiers that may be utilized to retrieve relevant data from the sub-episode eligibility data tables. In certain embodiments, the data management computing entity 65 may utilize a plurality of data tables, such that each data table is reflective of a single ETG. In other embodiments, the data management computing entity 65 may utilize one or more data tables each comprising data relating to a plurality of ETGs, thereby establishing a relation between an ETG and sub-episode eligibility criteria. Moreover, the sub-episode eligibility data table may additionally comprise data indicating whether a particular ETG is classified as "chronic" (which may impact how the sub-episode is truncated relative to the length of a parent episode), a priority value that similarly may be utilized for truncation of the sub-episode relative to other sub-episodes, grouping indicators establishing similarities/relatedness to other ETGs, and/or the like.

As reflected at Block 604, processing ends for records that do not have a diagnosis code to initiate a sub-episode and the process continues by determining whether other episode records are to be examined for sub-episode eligibility. There may be more than one sub-episode for the episode based on multiple diagnosis codes on the same claim being eligible for multiple sub-episodes.

In addition to diagnosis code eligibility, the data management computing entity 65 may be configured to implement additional criteria for establishing sub-episode eligibility, such as procedure code and/or provider specialty type requirements for an episode to establish eligibility to start a sub-episode (and/or other characteristics may be utilized to establish sub-episode eligibility). The data management computing entity 65 may be configured to reference a plurality of input reference tables (e.g., two input files) to identify a provider specialty type. These tables are Provider Key and Provider Specialty, which collectively establish a specialty type of a provider related to a particular episode.

As indicated at Block 605, for those episodes deemed eligible for supporting one or more sub-episodes, the data management computing entity 65 generates a listing in temporary memory comprising a listing of ETGs of the parent episode that are eligible for supporting one or more sub-episodes, along with sub-episode ETGs that may be supported by those parent-episode ETGs. The data management computing entity 65 utilizes this generated temporary listing as an episode-specific set of criteria for establishing sub-episodes that may be applied to the claim records associated with the parent episode to establish sub-episode anchor records as discussed in greater detail herein. Specifically, the data management computing entity 65 utilizes this generated episode-specific set of criteria when analyzing each anchor record of the parent episode, and accordingly the data management computing entity 65 generates a temporary listing of parent-episode anchor records as indicated at Block 606, such that further analysis may be performed on the contents of those anchor records while remaining records (anchor records or otherwise) may be removed from further analysis.

Figure 7:
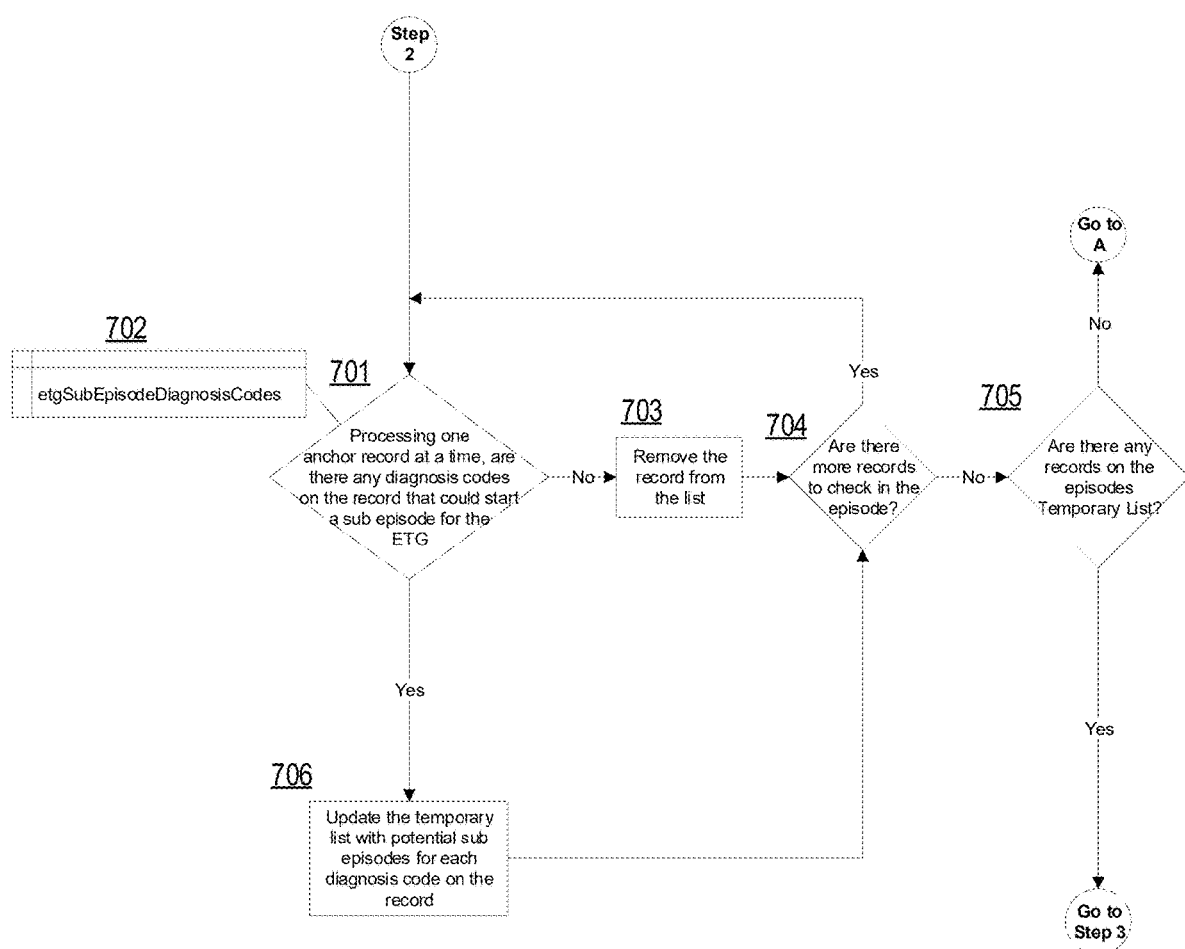

Referencing the overall flowchart of FIG. 5, the data management computing entity 65 compiles a listing of possible sub-episodes generated from qualified anchor records, based on diagnosis code(s) within those anchor records, as shown at Block 503 and reflected in detail in FIG. 7.

As shown in FIG. 7, the data management computing entity 65 reviews each anchor record of an episode individually to determine whether any diagnosis codes are eligible for supporting a sub-episode, with reference to episode-specific criteria stored temporarily (e.g., indicated by the etgSubEpisodeDiagnosisCodes data table of FIG. 7, which may establish relationships between diagnosis codes and sub-episode eligibility criteria), as indicated at Block 701-702. If the anchor record does not support any sub-episodes, the anchor record is removed from the generated temporary listing of anchor records of an episode, and the data management computing entity 65 determines if there are additional anchor records for analysis, and if there are additional episodes for analysis (after completion of analysis for a given episode), as indicated at Blocks 703-705, such that each anchor record of each episode of a claims record store are analyzed individually. For each anchor record determined to comprise diagnosis codes eligible to support sub-episodes, the temporary data table of anchor records associated with an episode is updated to reflect a listing of potential sub-episodes that may be supported by the anchor record, as indicated at Block 706.

Figure 8:
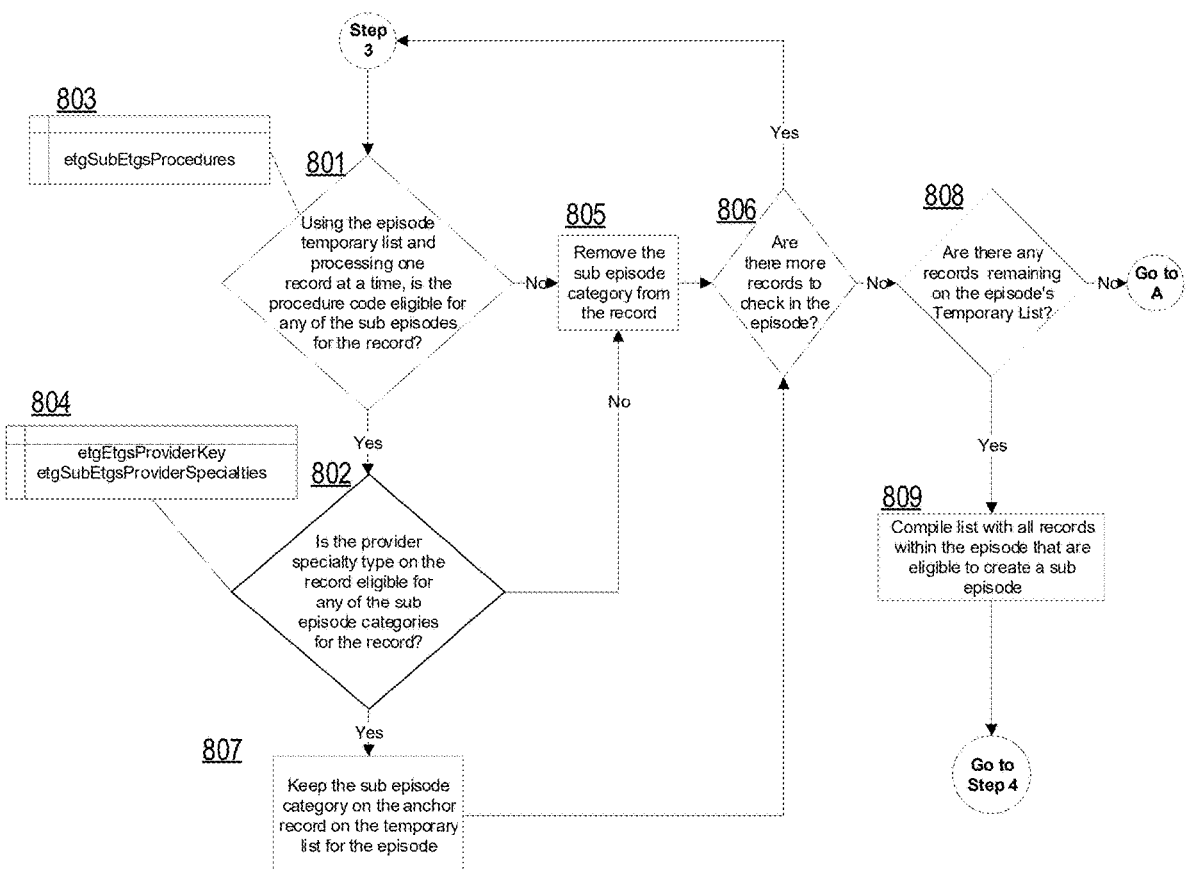

In certain embodiments, the data management computing entity 65 implements additional criteria for determining sub-episode eligibility, as reflected at Block 504 of FIG. 5 and as discussed in detail in reference to FIG. 8. In the illustrated embodiment, the additional criteria may be based at least in part procedures reflected by a particular episode and/or provider specialty associated with the episode.

As discussed herein, each episode is analyzed individually, and within an episode, each data record (associated with anchor records) is analyzed individually to determine eligibility for sub-episode support, as reflected at Block 801-804. As specifically reflected in Block 801, the data management computing entity 65 is configured to determine whether the procedures reflected within the record are eligible for supporting a sub-episode, with reference to a listing of procedures deemed eligible for supporting a sub-episode (utilized by the data management computing entity 65 as a procedure-based sub-episode eligibility criteria, which may be implemented as a data table such as the ctgSubEtgsProcedures data table reflected at Block 803). Moreover, as indicated at Block 802, the data management computing entity 65 is configured to determine whether a provider specialty associated with the anchor record is eligible for supporting a sub-episode (specifically, whether a provider indicated as a responsible provider for the claim record is associated with a specialty that is eligible for supporting a sub-episode), for example, by referencing data tables that indicates provider specialty eligibility for supporting sub-episodes (such as the etgEtgsProviderKey and etgEtgsProviderSpecialties data tables reflected by Block 804 and as discussed above, which include data relating a provider's unique identifier with a provider specialty, and relating the provider's specialty with applicable sub-episode eligibility criteria). If either of the analyses reflected by Blocks 801-802 determine that the particular record is ineligible for supporting a sub-episode, the data management computing entity 65 removes the record from the temporary listing of records associated with the episode, and determines if there are additional claim records for analysis for the episode, as reflected at Block 806. Those records indicated as satisfying all criteria for supporting a sub-episode are maintained within the temporarily listing of records associated with the episode (as reflected at Block 807), and the process repeats until all records have been analyzed. After all records have been analyzed, the data management computing entity 65 determines whether any records remain within the temporary listing of records associated with an episode (as shown in Block 808), and compiles a complete listing of records within an episode that are eligible to support a sub-episode, as shown in Block 809. The listing of records within an episode that are eligible for initiating a sub-episode may be provided as a temporary reflection of a hierarchical data structure of the episode, although the finalized sub-episodes that create the finalized hierarchical structure of the episode-specific data object may be subject to changes due to time-period related limitations and/or other limitations as discussed herein.

Figure 9:
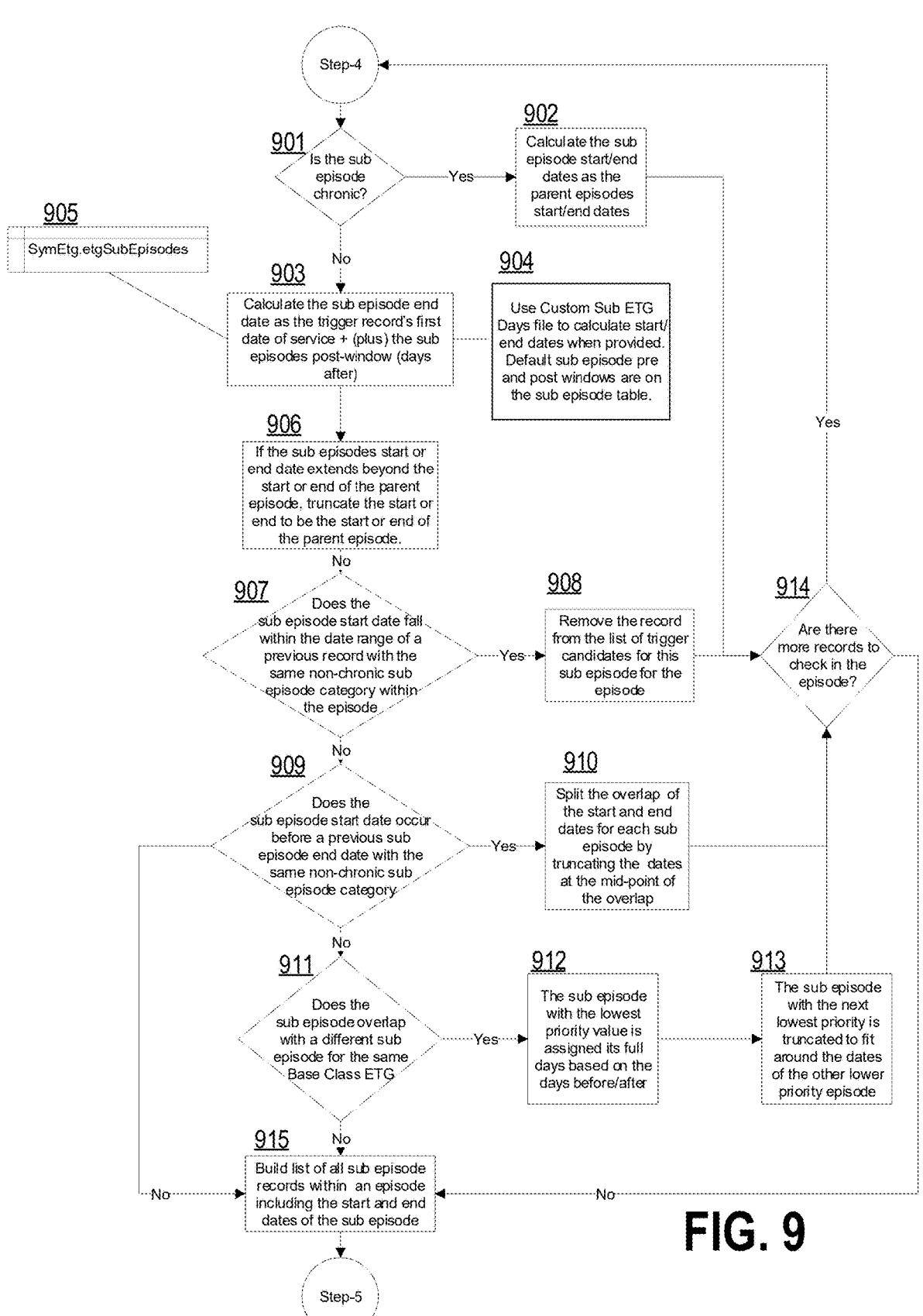

As reflected in Block 505 of FIG. 5, and more specifically within the process of FIG. 9, sub-episode date ranges defining start and end dates are calculated based on the start date of the anchor (trigger) record that initiated the Sub Episode in combination with the pre and post windows defined for that Sub Episode category. These date ranges may be utilized for establishing relationships between multiple sub-episodes within a single parent-episode, such that sub-episodes are not overlapping except in limited circumstances as defined by rules that may be implemented by the data management computing entity 65. Accordingly, generation of a hierarchical data structure within a data object associated with an episode comprises generating a two-level data structure within the data object, such that a top level comprises data generally applicable to the episode, and a second level comprises data applicable to each individual sub-episode, and may be organized such that the sub-episodes are non-overlapping. The sub-episode date range for a particular sub-episode may be determined based at least in part on characteristics of the sub-episode, such as a determination of whether the sub-episode is a chronic sub-episode, as determined in accordance with Block 901. If the sub-episode is determined to be chronic, the sub-episode date range is set to match the date range of the parent episode. Else, the data management computing entity 65 determines the sub-episode date range by determining the sub-episode's start date and end date, for example, with reference to the sub-episode's first date of service and a post-window (which may be identified from one or more data tables, such as the SymEtg.etgSubEpisodes data table of Block 905, which provides data indicative of initial time periods to be appended to a beginning of one or more claim records for establishing a start date of a claim record and associated episode or sub-episode as well as data indicative of post time periods to be appended to an end of one or more claim records to establish an end date of the claim record and associated episode or sub-episode), as indicated at Blocks 903 and 904. However, the data management computing entity 65 is additionally configured to compare the determined and temporarily stored sub-episode date range relative to the parent episode date range, and to truncate the sub-episode date range such that the sub-episode date range does not extend beyond the start date and/or end date of the parent episode, as shown at Block 906.

As reflected in the steps of Blocks 907-910, the data management computing entity 65 is configured to truncate the sub-episode date range to continue to satisfy rules regarding sub-episode attribution to episodes. For example, the data management computing entity 65 may be configured to maintain adherence to rules specifying that (1) sub-episodes cannot extend beyond start and end dates of parent episodes, and (2) sub-episodes cannot overlap in time within an episode. As specifically shown in Blocks 907-908, dates from each claim record associated with a sub-episode category are used to identify an earliest date associated with a sub-episode and to establish (at least temporarily) a sub-episode start date based on an earliest claim record associated with the sub-episode. Those records that do not establish an earliest date associated with the sub-episode are removed from a listing of candidate records for establishing a start date or end date of the sub-episode. Moreover, as indicated in Blocks 909-910, temporarily established date ranges for individual sub-episodes associated with a parent episode are compared, and those date ranges determined to overlap for differing sub-episodes are truncated to eliminate the overlapping date ranges between consecutive sub-episodes. As just one example, the overlapping time period between sub-episodes may be divided equally between adjacent sub-episodes by truncating each date range at a mid-point of the overlapping time period. Other strategies may be utilized for dividing the overlapping time period between adjacent sub-episodes. For example, for sub-episodes determined to have differing priority values (e.g., based on priority values assigned to particular ETGs being associated with different sub-episodes as established within an ETG data table, the data management computing entity 65 is configured to compare priority values associated with each sub-episode, and to assign overlapping time periods between the sub-episodes to the sub-episode having a winning priority ranking (e.g., a higher priority rank may be utilized in certain embodiments, or a lower priority number (corresponding to a greater indication of priority) as may be indicated in the embodiments of FIG. 9. Blocks 911-912 illustrate the process for awarding overlapping sub-episode time periods to a specific time period based on priority. As indicated in Block 913, the losing sub-episode is truncated so as not to overlap the time period and an appropriate start time and ending time is assigned to the sub-episode so as not to overlap other sub-episodes within the same parent episode.

After determining date ranges to be assigned to each of the plurality of sub-episodes, the data management computing entity 65 loops through the sub-episode date-range determination process as reflected at Block 914 of each record, and the data management computing entity 65 builds a list of sub-episode records associated with a parent episode, together with data indicating corresponding date ranges for each of the sub-episodes, as reflected in Block 915.

Figure 10:
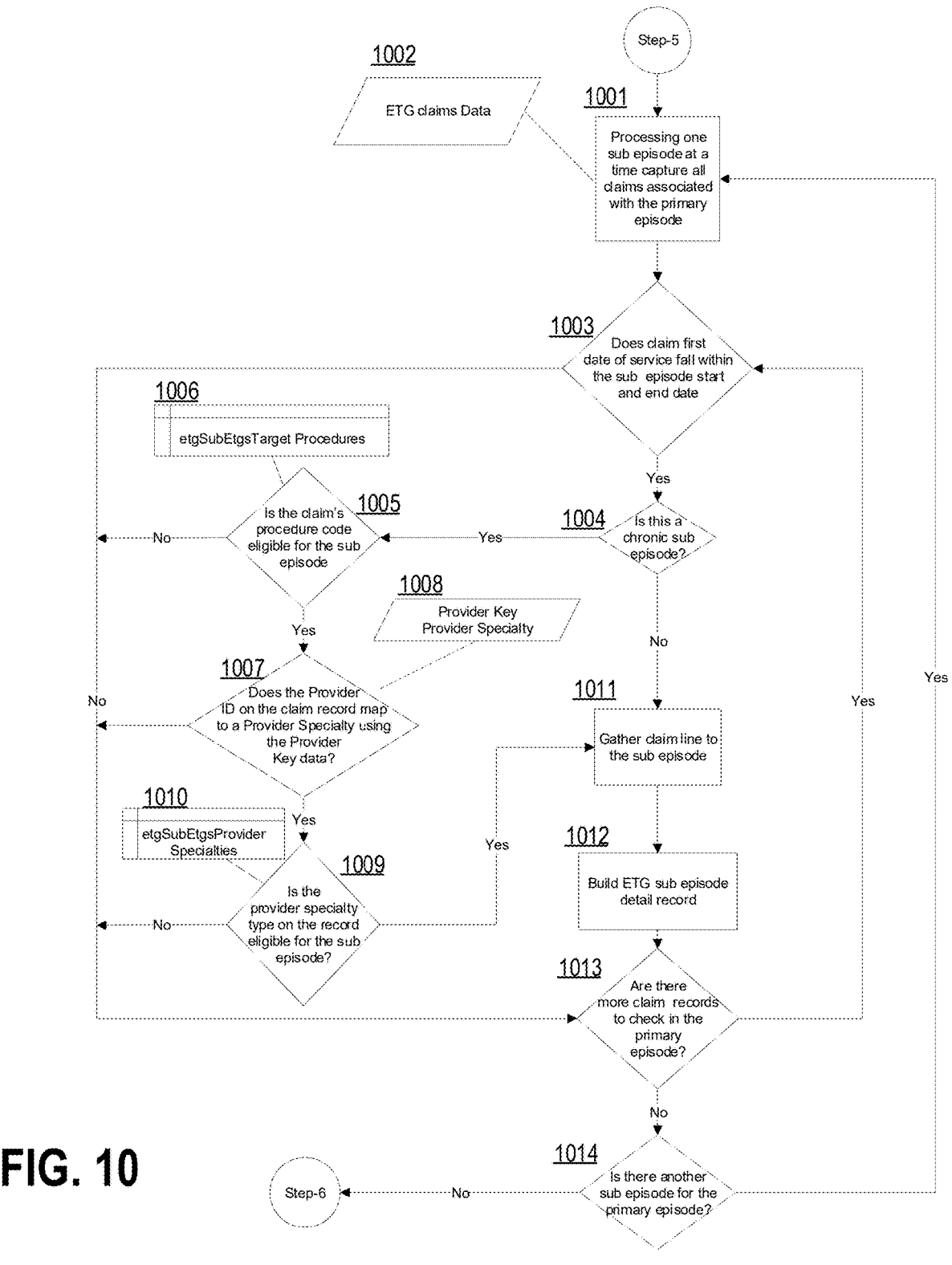
Figure 11:
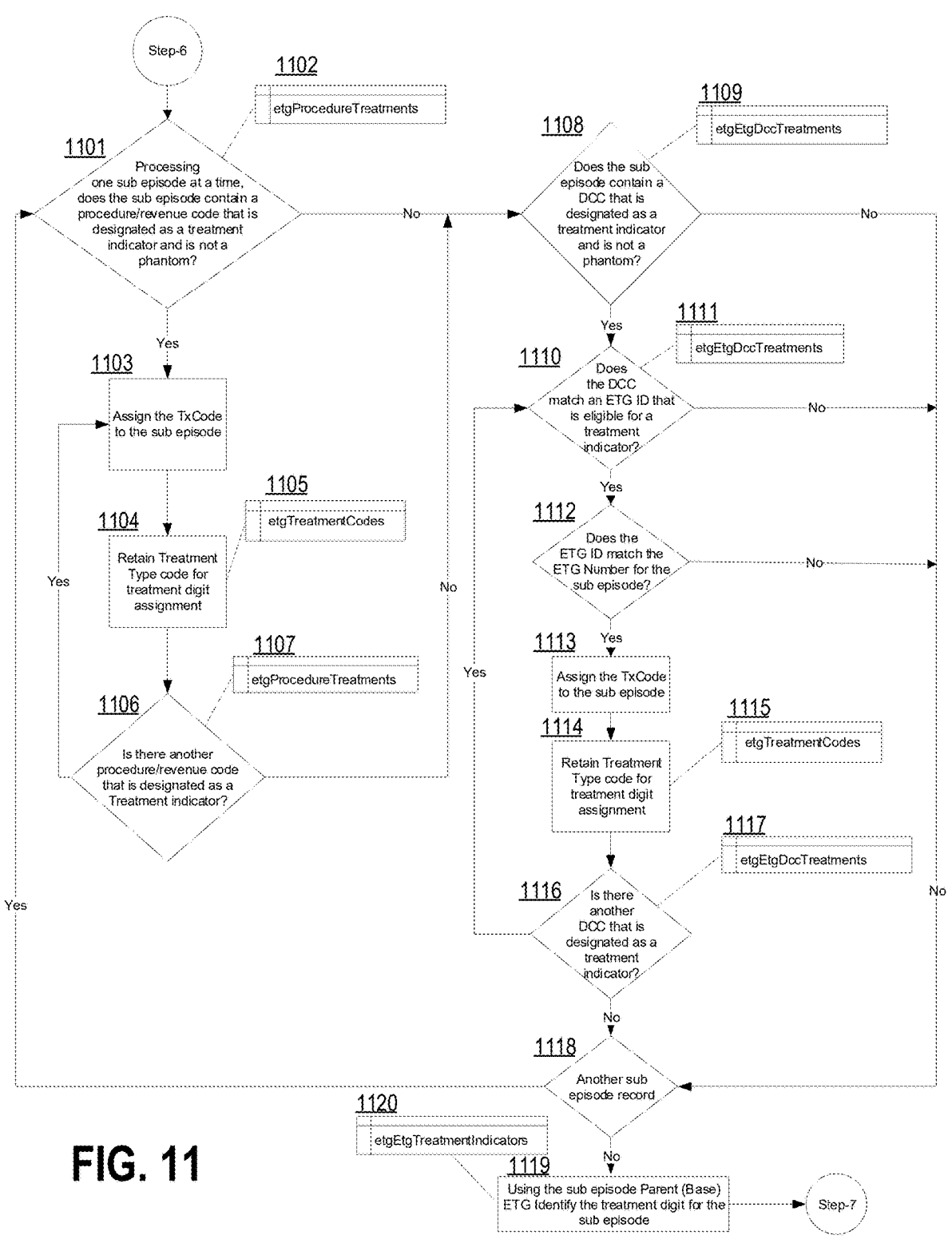

As reflected at Block 506 of FIG. 5, and the process illustrated in FIG. 10, the data management computing entity 65 populates the sub-episodes with additional claims (e.g., ancillary claims, drug claims, and/or the like). As indicated at Blocks 1001-1002, sub-episodes are analyzed individually for addition of various claims data to populate the sub-episode, referencing stored claims data. For each claim record associated with a particular parent episode, the data management computing entity 65 determines whether the claim record falls within the date range established for the particular sub-episode being reviewed, as indicated at Block 1003. The data management computing entity 65 loops through all claim records for each sub-episode, skipping those claim records that do not fall within the time frame associated with the sub-episode. Further analysis of the data management computing entity 65 may be dependent on the type of sub-episode being analyzed. For example, chronic episodes (identified as indicated at Block 1004), may subject individual claim records to additional analysis, such as a determination of whether the claim record's identified procedure code is eligible for sub-episode treatment, as indicated at Block 1005 (with reference to one or more data tables identifying those procedures that are eligible for sub-episode treatment, such as an etgSubEtgsTarget Procedures data table as indicated at Block 1006, which may comprise data indicating characteristics of particular procedure codes, including characteristics indicating whether a particular procedure code is eligible for generating one or more sub-episodes and/or priority data for a particular procedure that may be utilized to establish relative priorities of various procedures reflected within an episode or sub-episode). Similarly, a claim record may be subject to a determination of whether the responsible provider for a claim record is associated with a provider type that is eligible for sub-episode treatment, as indicated at Blocks 1007 and 1009 (with reference to one or more data tables indicating a provider's specialty, and indicating whether the provider's specialty is eligible for sub-episode treatment, as indicated at Blocks 1008 and 1010, such data tables may be the same or analogous as those discussed in reference to Block 804, above). Those claim records determined to be ineligible for sub-episode treatment based on an included procedure code and/or an included responsible provider's specialty are skipped as the data management computing entity 65 loops through all claim records.

For those claim records satisfying applicable criteria of a chronic sub-episode, as well as those claim records falling within an applicable date range of a sub-episode not indicated as a chronic sub-episode, the data management computing entity 65 associates the claim record with the sub-episode, as indicated at Block 1011, and the data management computing entity 65 generates an ETG sub-episode detail record to be associated with the episode-specific data object, as indicated at Block 1012, before looping to additional claim records, as indicated at Block 1013, and then looping to additional sub episodes, as indicated at Block 1014.

The data management computing entity 65 then completes a plurality of sub-episode finalization steps, beginning with Block 507 of the illustrated embodiment of FIG. 5. As shown in Block 507 specifically, the data management computing entity 65 identifies and assigns treatment indicators to sub-episodes in accordance with the methodology as discussed in reference to FIG. 11. Each sub-episode is considered individually for assignment of treatment indicators, as reflected at Block 1101. Assignment of treatment indicators may comprise an analysis of a plurality of different characteristics of each sub-episode. For example, as indicated at Block 1101, the data management computing entity 65 may determine whether the sub-episode contains a procedure code that satisfies various treatment-indicator related criteria, such as determining whether the procedure code is itself indicative of a treatment indicator and is not a phantom episode. Such determinations may be performed in accordance with data stored within a relevant data table, as indicated at Block 1102 (e.g., an etgProcedureTreatments data table providing data indicative of characteristics of particular procedures (reflected within claim records and/or sub-episodes) for establishing treatment codes relevant to procedures). For those sub-episodes determined to satisfy the initial criteria reflected in Block 1101, the data management computing entity 65 assigns the relevant treatment code to the sub-episode as indicated at Block 1103, and determines applicable treatment type codes with reference to a corresponding data table (such as an etgTreatmentCodes data table providing data indicative of characteristics of particular claim records and/or sub-episodes for matching particular treatment codes to claim records), as indicated at Blocks 1104-1105, before looping back to other procedure codes stored in association with the sub-episode to determine whether additional codes are present for additional analysis, as indicated at Block 1106 (with reference to the data table of Block 1107, such as the etgProcedureTreatments data table discussed in reference to Block 1102).

For those sub-episodes determined not to satisfy the criteria of Block 1101 (or upon review of procedure codes that do not satisfy the criteria of Block 1101), the data management computing entity 65 is configured to determine whether the sub-episode contains a DCC designated as a treatment indicator (and that is not a phantom), as shown at Block 1108, with reference to a relevant data table (such as an etgEtgDccTreatments data table as reflected at Block 1109, which may comprise data indicating whether particular DCC codes are eligible for certain treatment indicators). For those DCCs identified by the data management computing entity 65 as satisfying the requirements of Block 1108, the data management computing entity 65 determines whether those DCCs match appropriate an appropriate ETG identifier that is indicated within a data table that the ETG identifier is eligible for a treatment indicator (as indicated at Block 1110 with reference to the data table of Block 1111, such as the etgEtgDccTreatments data table discussed in reference to Block 1109). For those DCCs indicated as associated with an ETG identifier that is eligible for a treatment indicator, the data management computing entity 65 determines whether the ETG identifier matches the ETG number for the sub-episode, and if so, assigns the relevant treatment indicator to the sub-episode, as indicated at Blocks 1112-1113. The data management computing entity 65 then determines applicable treatment type codes with reference to a corresponding data table, as indicated at Blocks 1114-1115 (e.g., with reference to the etgTreatmentCodes data table discussed in reference to Block 1105) before looping back to other DCC codes stored in association with the sub-episode to determine whether additional codes are present for additional analysis, as indicated at Blocks 1116-1117 (e.g., with reference to the etcEtgDccTreatments data table discussed in reference to Block 1109).

For those sub-episodes that do not include DCC codes for analysis (or after completing the analysis of the final DCC code associated with a sub-episode, the data management computing entity 65 determines whether other sub-episodes are present for additional analysis, as indicated at Block 1118 before finalizing the treatment indicators for a sub-episode, as reflected within a listing of treatment indicator digits associated with the parent episode, as reflected at Block 1119, with reference to a data table as shown at Block 1120, such as an etgEtgTreatmentIndicators data table correlating particular characteristics with treatment indicator digits to be associated with particular sub-episodes.

Figure 12:
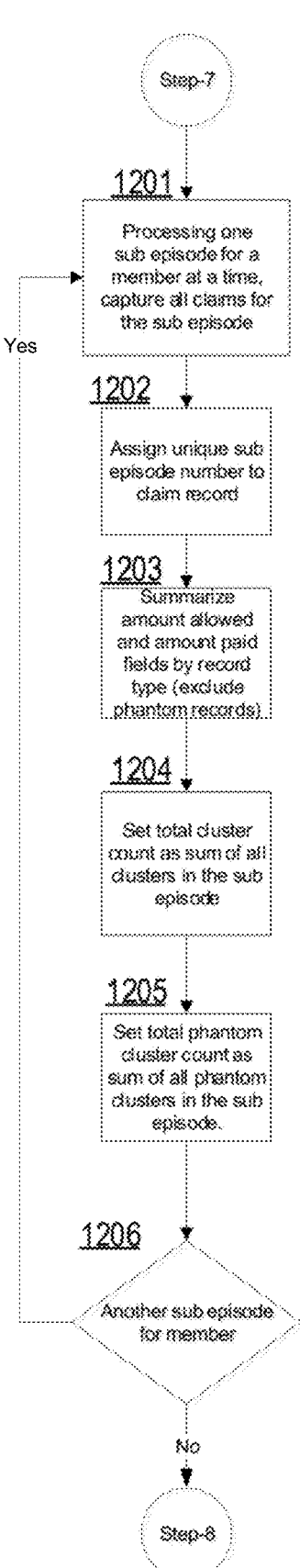

The data management computing entity 65 continues finalization processes for the sub-episodes as reflected at Block 508 of FIG. 5, by generating a summary of the sub-episode (in accordance with the specific process steps of FIG. 12). The data management computing entity 65 is configured to execute the steps of FIG. 12 for a single sub-episode before repeating the process of FIG. 12 for other sub-episodes. Accordingly, as shown in Block 1201, the data management computing entity 65 captures all claim records associated with a particular sub-episode for further analysis and generation of a summary.

As reflected within Block 1202, the data management computing entity 65 is configured to assign a unique sub-episode identifier to each sub-episode (e.g., which may comprise a unique parent-episode identifier together with an indicator of relevance to a sub-episode), and to assign the unique sub-episode identifier to each claim record retrieved and associated with the sub-episode. The claim records may be updated to include the unique sub-episode identifier, or the data management computing entity 65 may be configured to update an episode data record (e.g., a summary data record) comprising a listing of claim records associated with the episode to include the unique sub-episode identifier in combination with each claim record.

Generating the summary of a particular episode comprises generating summaries of specific characteristics of the episode, such as generating a summary of a total allowed amount and amount paid by record type for each sub-episode, as shown at Block 1203. Characteristics of a particular sub-episode may additionally be summarized by summarizing the total number of clusters (or individual claim records) associated with a particular sub-episode, as indicated at Block 1204, and for generating a total phantom cluster count for the sub-episode, as indicated at Block 1205. The processes for summarizing individual sub-episodes of an episode are repeated for each sub-episode within the episode, as indicated at Block 1206.

Figure 13:
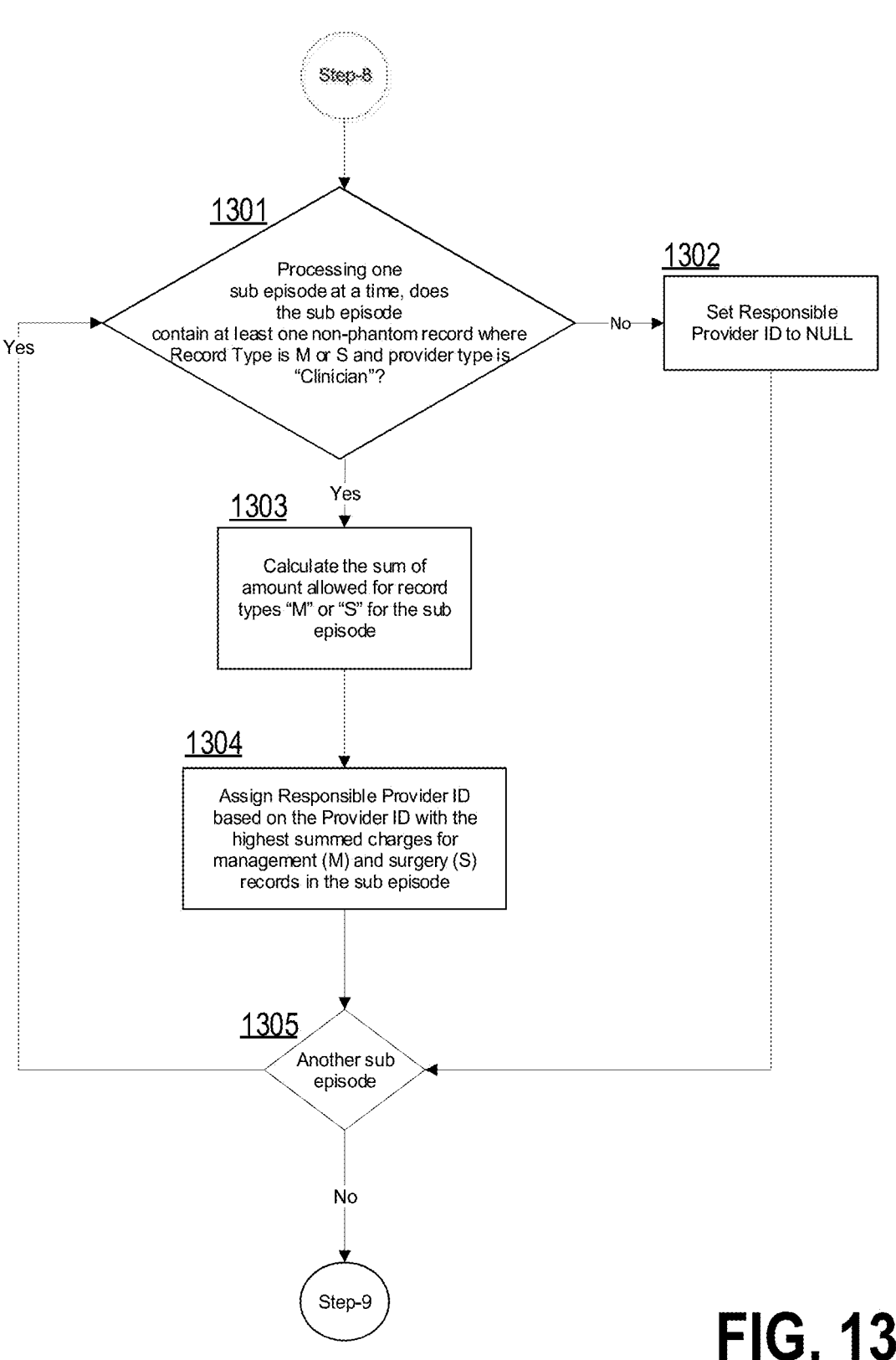

With reference again to FIG. 5, the data management computing entity 65 assigns a responsible provider to each sub-episode to enable further analysis thereof, as indicated at Block 509. FIG. 13 provides additional detail regarding processes for assigning a responsible provider to a particular sub-episode. As discussed throughout this disclosure, the data management computing entity 65 is configured to process each sub-episode individually to assign a responsible provider, and as indicated at Block 1301, the data management computing entity 65 determines whether the sub-episode includes at least one claim record satisfying applicable criteria, such as determining whether the sub-episode includes at least one claim record having one of a specified listing of record types and satisfying provider type requirements. If the data management computing entity 65 determines that the sub-episode does not include any episodes satisfying such criteria, the provider identifier is set to NULL, as indicated at Block 1302, and the process is repeated for additional sub-episodes.

However, upon the data management computing entity 65 identifying at least one claim record satisfying the applicable criteria for assignment of a responsible provider, the data management computing entity 65 calculates the sum of allowed amounts for record types satisfying the applicable criteria for the sub-episode, and temporarily stores the calculated total for further analysis, as indicated at Block 1303. The data management computing entity 65 then assigns the responsible provider identifier to the sub-episode as being the provider having the highest summed charges for those claim records satisfying the applicable criteria (e.g., management or surgery records). Upon assigning a responsible provider (or assigning a NULL responsible provider as discussed above), the process is repeated for other sub-episodes, as indicated at Block 1305.

Figure 14:
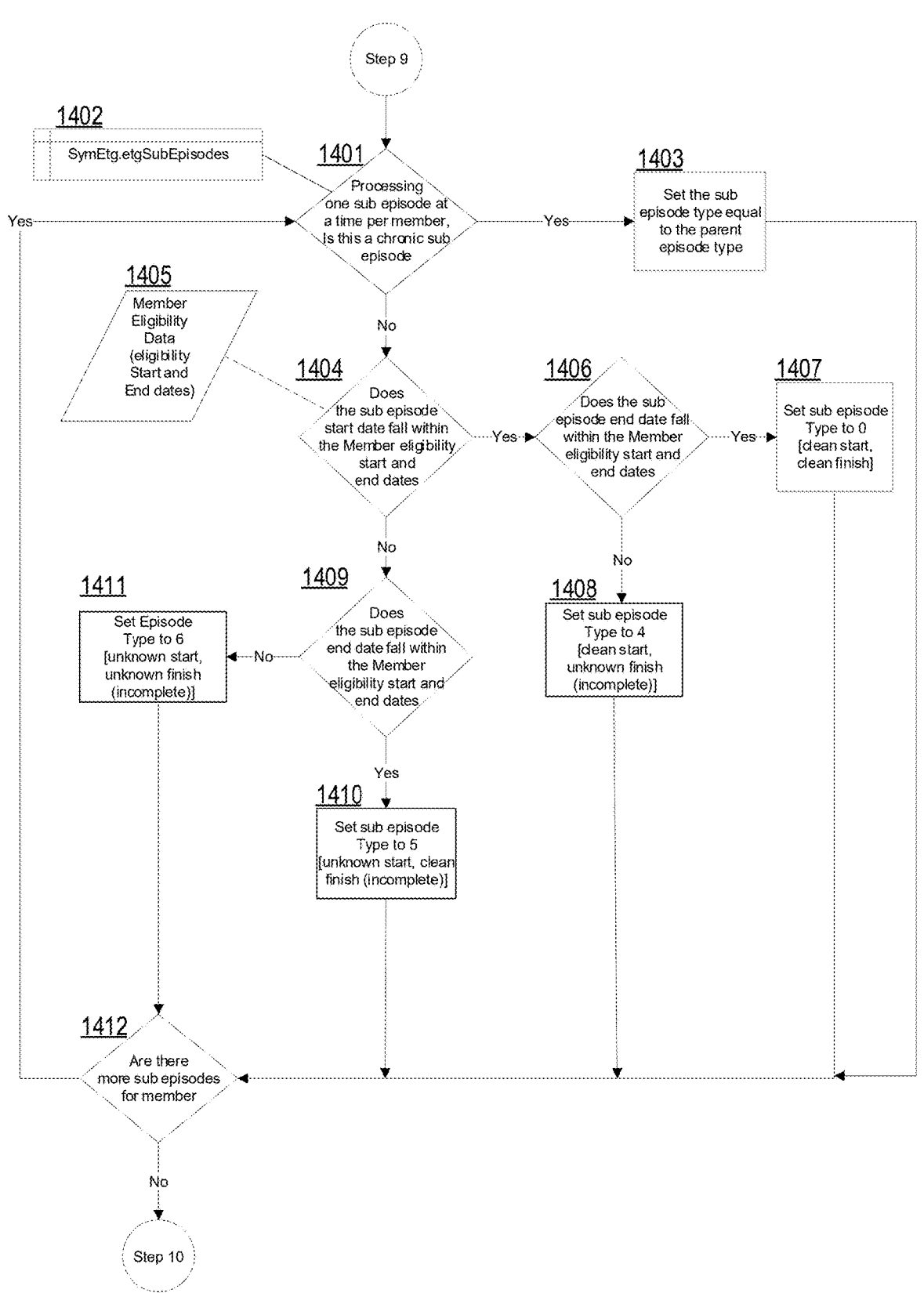

The data management computing entity 65 is additionally configured to assign an episode type to each sub-episode, as indicated at Block 510 of FIG. 5, and as discussed in greater detail in reference to FIG. 14. As illustrated at Block 1401, the data management computing entity 65 reviews each sub-episode individually for assigning sub-episode types and begins by determining whether the sub-episode is a chronic sub-episode. Such determinations may be made with reference to relevant data tables as reflected in Block 1402 (such as a SymEtg.etgSubEpisodes data table providing reference data indicating characteristics of particular ETGs, including data indicating whether a particular ETG is classified as a chronic ETG). For those sub-episodes determined to be chronic episodes, the sub-episode is assigned the same episode type as the parent episode as indicated at Block 1403.

For those sub-episodes that are determined not to be chronic episodes, the data management computing entity 65 is configured to complete additional analyses of each sub-episode to determine an appropriate episode type to be assigned to the sub-episode. As indicated beginning with Block 1404, the data management computing entity 65 initially determines whether the sub-episode start date falls within the member eligibility dates, with reference to member eligibility date stored for specific patients within a data table, as indicated at Block 1405, such as member eligibility data tables as discussed herein.

For those sub-episodes determined to fall within member eligibility date ranges (specifically, for episodes beginning within an eligibility date range as determined in reference to Block 1404 and an end date falling within member eligibility dates as determined in reference to Block 1406), the data management computing entity 65 sets the sub-episode type to indicate a clean-start and clean finish (having a corresponding identifier, such as "0" as indicated at Block 1407).

For those episodes that are determined to have a start date falling within a member eligibility date range, but having an end date that does not fall within a member eligibility date range, the sub-episode type may be established to be "clean start, unknown finish/incomplete (having a corresponding identifier, such as "4" as indicated at Block 1408).

For those episodes that are determined to have a start date that does not fall within a member eligibility range, but having an end date that does fall within a member eligibility range (as determined in reference to Block 1409), the sub-episode type may be established to be "unknown start, clean finish/incomplete" (having a corresponding identifier, such as "5" as indicated at Block 1410). For those episodes that are determined to have both start dates and end dates that are outside of a member eligibility range, the sub-episode type may be established as "unknown start, unknown finish/incomplete" (having a corresponding identifier, such as "6" as shown at Block 1411). After establishing an episode type for a particular sub-episode, the data management computing entity 65 determines whether additional sub-episodes require assignment of episode types, as indicated at Block 1412.

Figure 15:
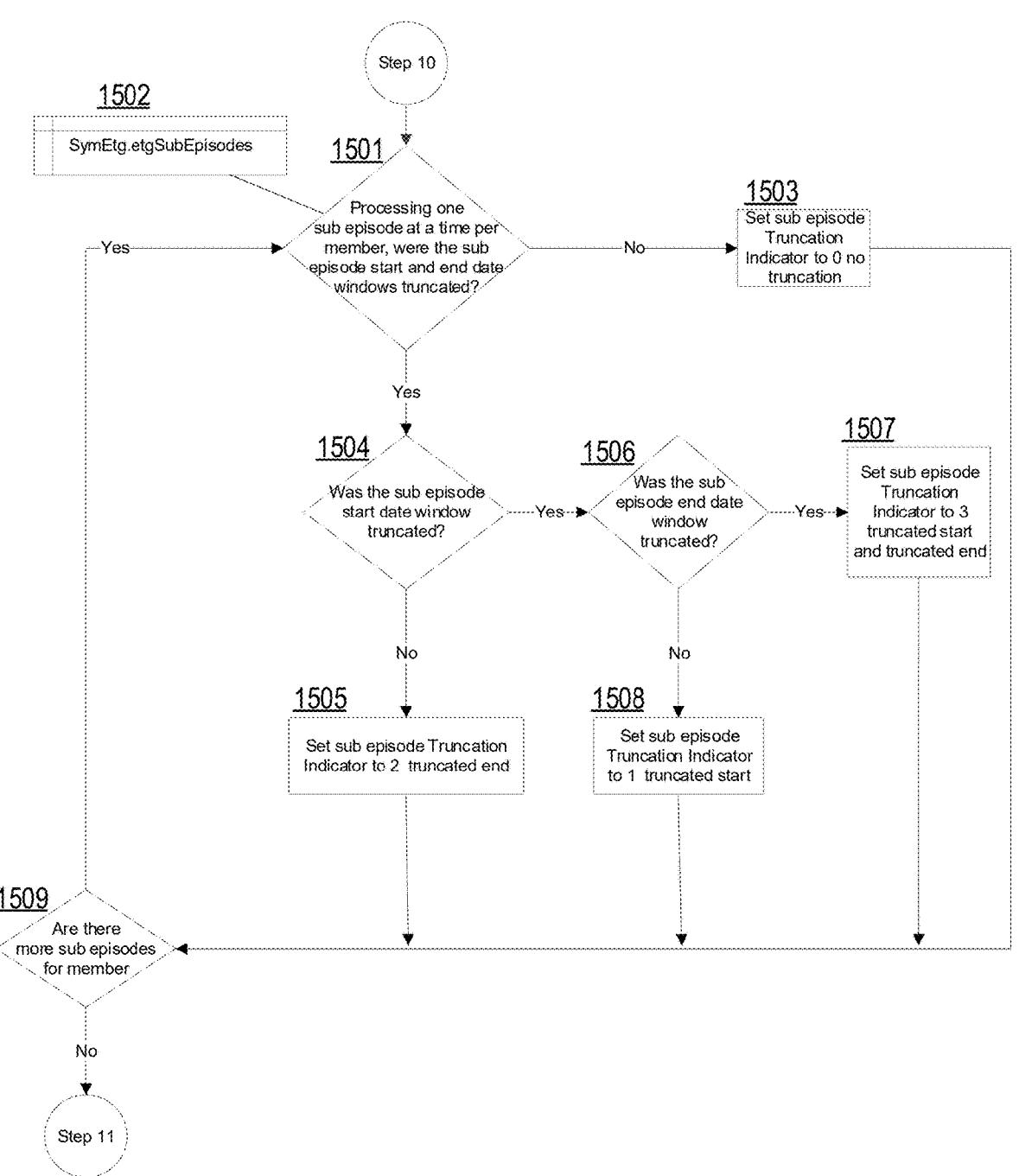

With reference to Block 511 of FIG. 5, the data management computing entity 65 assigns truncation indicators to each sub-episode in accordance with the methodology discussed in reference to FIG. 15. As indicated at Block 1501, each sub-episode is reviewed individually for assigning truncation indicators, and the data management computing entity 65 determines whether the sub-episode start date and/or end date was truncated. Such review proceeds with reference to an appropriate data table, as shown in Block 1502 (e.g., the SymEtg.etgSubEpisodes data table discussed in reference to Block 1402, above). For those sub-episodes that have not been truncated, the data management computing entity 65 sets a truncation indicator to "no truncation" (having a corresponding indicator of "0" as indicated in Block 1503).

For those episodes that have been determined to have been truncated, the data management computing entity 65 determines whether the start date was truncated, as indicated at Block 1504. Upon determining that the start date was not truncated (but the sub-episode was subject to truncation, as determined at Block 1501), the data management computing entity 65 sets the sub-episode truncation indicator to "truncated end" (having a corresponding indicator of "2" as shown at Block 1505). However, if the episode start date was determined to be truncated, the data management computing entity 65 additionally determines if the end date was additionally truncated, as indicated at Block 1506. Upon determining that both the start date and end date was truncated, the data management computing entity 65 is configured to set the truncation indicator to "truncated start and truncated end" with a corresponding indicator of "3" as shown in Block 1507. For those sub-episodes determined to have a truncated start but not a truncated end, the sub-episode truncation indicator is set to "truncated start" (with a corresponding indicator of "1" as shown in Block 1508). The data management computing entity 65 then determines whether any additional sub-episodes require truncation indicators as shown at Block 1509, and the process is repeated for any remaining sub-episodes.

Figure 16:
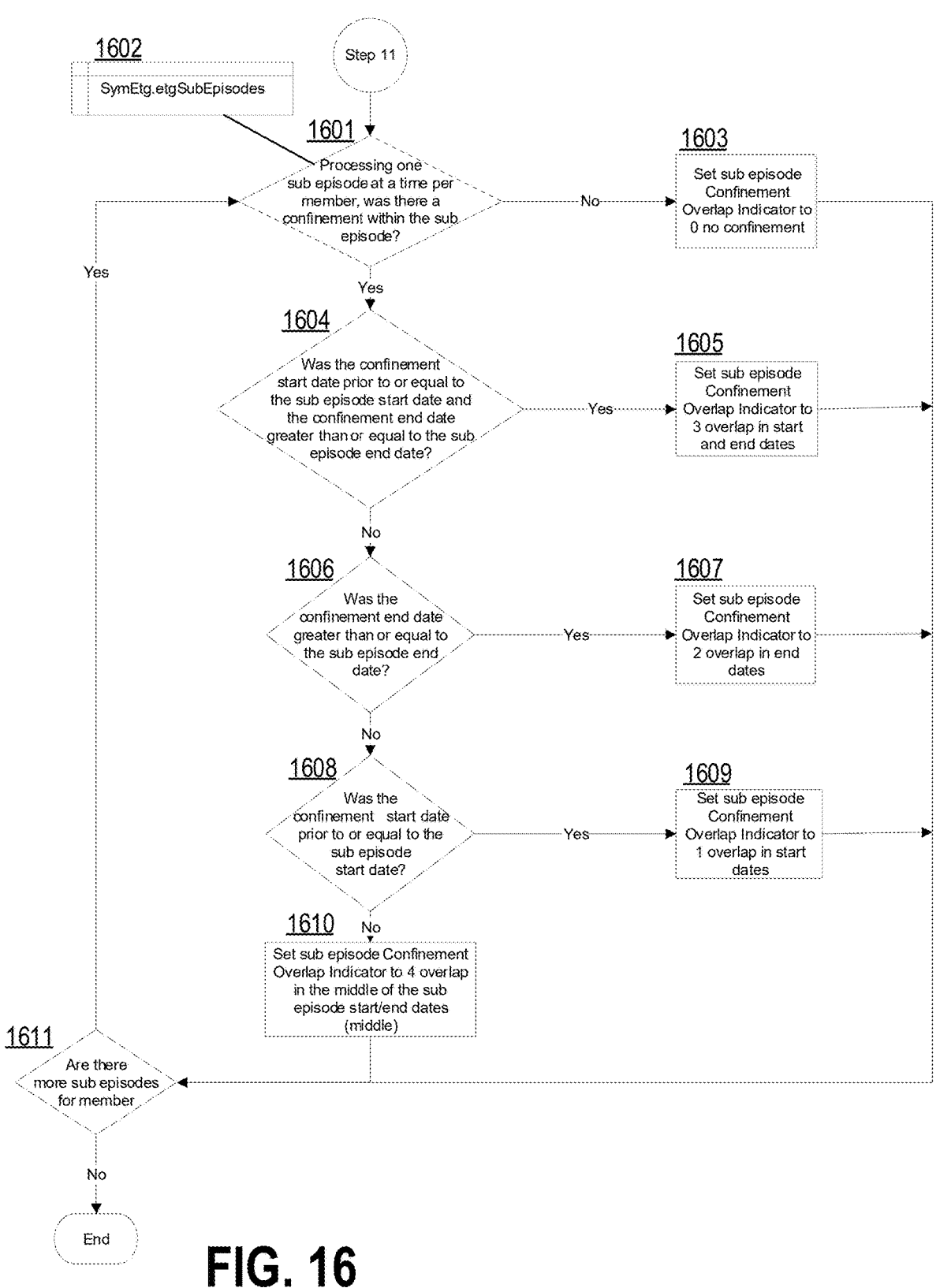
Figure 17:
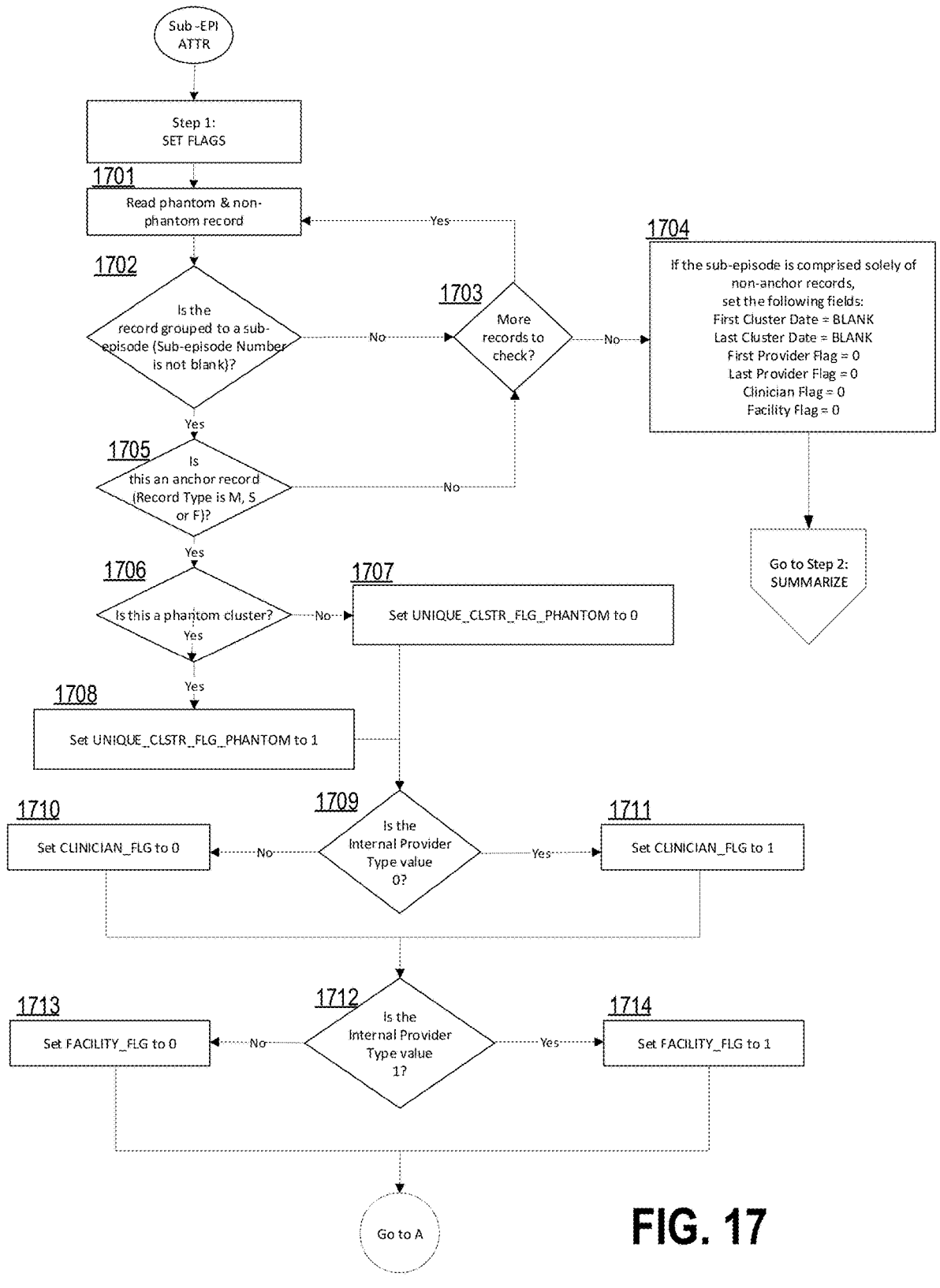

Additional sub-episode finalization comprises assigning confinement indicators to sub-episodes, as shown at Block 512 of FIG. 5 and as discussed in greater detail in reference to FIG. 16. As shown at Block 1601, the data management computing entity 65 is configured to analyze each sub-episode individually for assignment of confinement indicators, and the data management computing entity 65 initially determines whether there was a confinement within a particular sub-episode. The data management computing entity 65 references a data table as indicated at Block 1602 (e.g., the SymEtg.etgSubEpisodes data table discussed in reference to Block 1402, above) in determining whether a confinement is present within a sub-episode. Upon determining that a confinement is not present within a sub-episode, the data management computing entity 65 sets a sub-episode confinement overlap indicator to indicate "no confinement" (with a corresponding indicator of "0" as shown in Block 1603). Upon determining that a confinement is present within a sub-episode, the data management computing entity 65 determines whether the start date of the confinement and/or end date of the confinement matches the sub-episode start date and/or end date (respectively), as indicated at Block 1604. Upon determining that the confinement extends to or beyond both the start and end dates of the sub-episode, the data management computing entity 65 sets the sub-episode confinement indicator to indicate an overlap in start and end dates (with a corresponding indicator of "3" as shown in Block 1605).

Upon determining that the confinement does not overlap both the start and end dates of the sub-episode, the data management computing entity 65 determines whether each end individually overlaps an end of the sub-episode. As indicated at Block 1606, the data management computing entity 65 determines whether the end date of the confinement extends to or beyond the end date of the sub-episode, and upon determining that the confinement extends beyond an end date of the sub-episode, the data management computing entity 65 sets a sub-episode confinement indicator to indicate an overlap in end dates (with a corresponding indicator of "2" as shown at Block 1607).

Upon determining that the confinement does not overlap an end date of the sub-episode, the data management computing entity 65 determines whether the confinement overlaps a start date of the sub-episode, as indicated at Block 1608. Upon determining that the confinement does not overlap an end date of the sub-episode, but does overlap the start date of the sub-episode, the data management computing entity 65 sets the sub-episode confinement overlap indicator to indicate an overlap in start dates (with a corresponding indicator of "1" as shown at Block 1609).

Upon determining that the confinement does not overlap a start date of the sub-episode and does not overlap an end date of the sub-episode, but the sub-episode is determined to include a confinement, the data management computing entity 65 is configured to set a confinement overlap indicator to indicate an overlap in a middle of the sub-episode (with a corresponding indicator of "4" as shown in Block 1610). After setting a confinement indicator in accordance with the characteristics of sub-episode, the data management computing entity 65 determines whether additional sub-episodes are to be analyzed for assignment of a confinement indicator, as indicated at Block 1611.

d. Sub-Episode Attribution Output Generation

After claim records have processed via the data management computing entity 65, the data management computing entity 65 collects all claim records that were grouped to a sub-episode to produce the sub-episode attribution output. Counts, costs, percentage, flags and dates are computed for every Cluster Provider ID associated with a sub-episode. Counts may be computed for office visits (distinguishing between E&M visits just in a non-acute setting and E&M visits in both non-acute and acute settings), for management and surgery services, and for clusters. Costs are computed for management and surgery services, for clusters, and for management, surgery and room & board services. Percentage of Total Allowed is computed for every Cluster Provider ID associated with a Sub Episode. Flags are computed to indicate if the Cluster Provider ID is the first provider and/or last provider within the Sub Episode, and to indicate if the Cluster Provider ID is a clinician or a facility. Lastly, the first cluster date and last cluster date associated with the Cluster Provider ID are also assigned, which show the date span of that provider's involvement within the Sub Episode.

All claim records that contributed to a real or phantom sub-episode may be analyzed, including phantom records. If a phantom sub-episode is created, that phantom sub-episode may be subject to attribution analysis. A phantom sub-episode comprises phantom anchor records; those phantom anchor records being a copy of the real claim record that were primarily grouped into another episode or sub-episode.

Due to phantom anchor records being duplicate claim records, they are included in only some of the counts and in none of the costs or percentage calculation. Phantom anchor records are used in determining the first provider flag, last provider flag, first cluster date, last cluster date, clinician flag, facility flag, count of office visits (total E&M visits and non-acute E&M visits) and a count of clusters including phantom clusters. All other data elements computed do not use phantom anchors as that would result in double-counting costs and counts.

As discussed herein with reference to FIGS. 17-20, claims are attributed and summarized so as to enable payment to an appropriate provider and to enable generation of reports and appropriate outputs, as necessitated by various embodiments. Attributions may be provided in accordance with various flags associated with the sub-episodes, as assigned in accordance with the methodology summarized in FIGS. 17-20. As indicated in Block 1701, both phantom and non-phantom claim records may be reviewed in accordance with certain embodiments. As discussed herein, phantom records are duplicate records that are associated with particular episode or sub-episode and are reflected within additional episodes to provide a complete view of treatments provided in accordance with multiple episodes (or sub-episodes).

As shown at Block 1702, the data management computing entity 65 determines whether the claim record being analyzed is linked with a sub-episode (and/or episode), and for those claim records that are not associated with an episode and/or sub-episode, the data management computing entity 65 determines whether additional claim records remain to be analyzed as indicated at Block 1703 (to repeat the process initiated at Block 1701), and assigns flags to sub-episodes upon determining that the sub-episode comprises only non-anchor records. Those flags may indicate the presence of no clusters, provider flags, clinician flags, or facility flags, as indicated at Block 1704.

However, for those claim records indicated as linked with a sub-episode, the data management computing entity 65 determines whether the claim record is an anchor record as indicated at Block 1705, and for those non-anchor records, the data management computing entity 65 repeats the process by determining whether additional claim records are awaiting analysis and attribution. For anchor records, the data management computing entity 65 determines whether the record defines a phantom cluster as indicated at Block 1706. Phantom clusters are assigned a flag indicating a unique phantom cluster, and non-phantom clusters are assigned an opposite flag (of a binary set of flag options) indicating the cluster is a non-phantom cluster, as indicated at Blocks 1707-1708.

As indicated at Block 1709-1711, the data management computing entity 65 determines whether the internal provider type of a claim record is a clinician record type and assigns a corresponding flag, and the data management computing entity 65 performs a similar analysis to determine whether the internal provider type of the claim record is a facility record type and assigns a corresponding flag, as indicated at Blocks 1712-1714.

Figure 18:
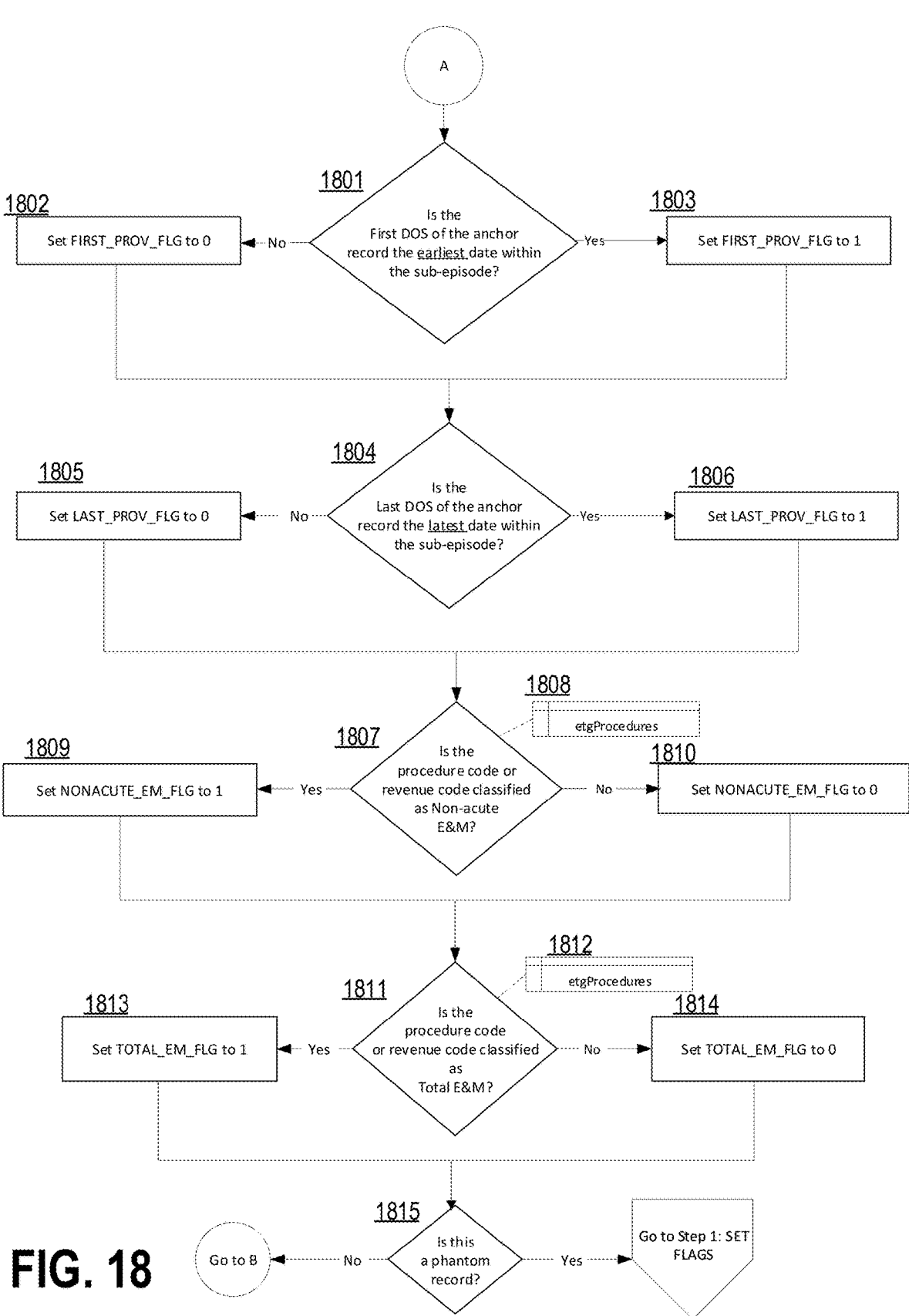
Figure 19:
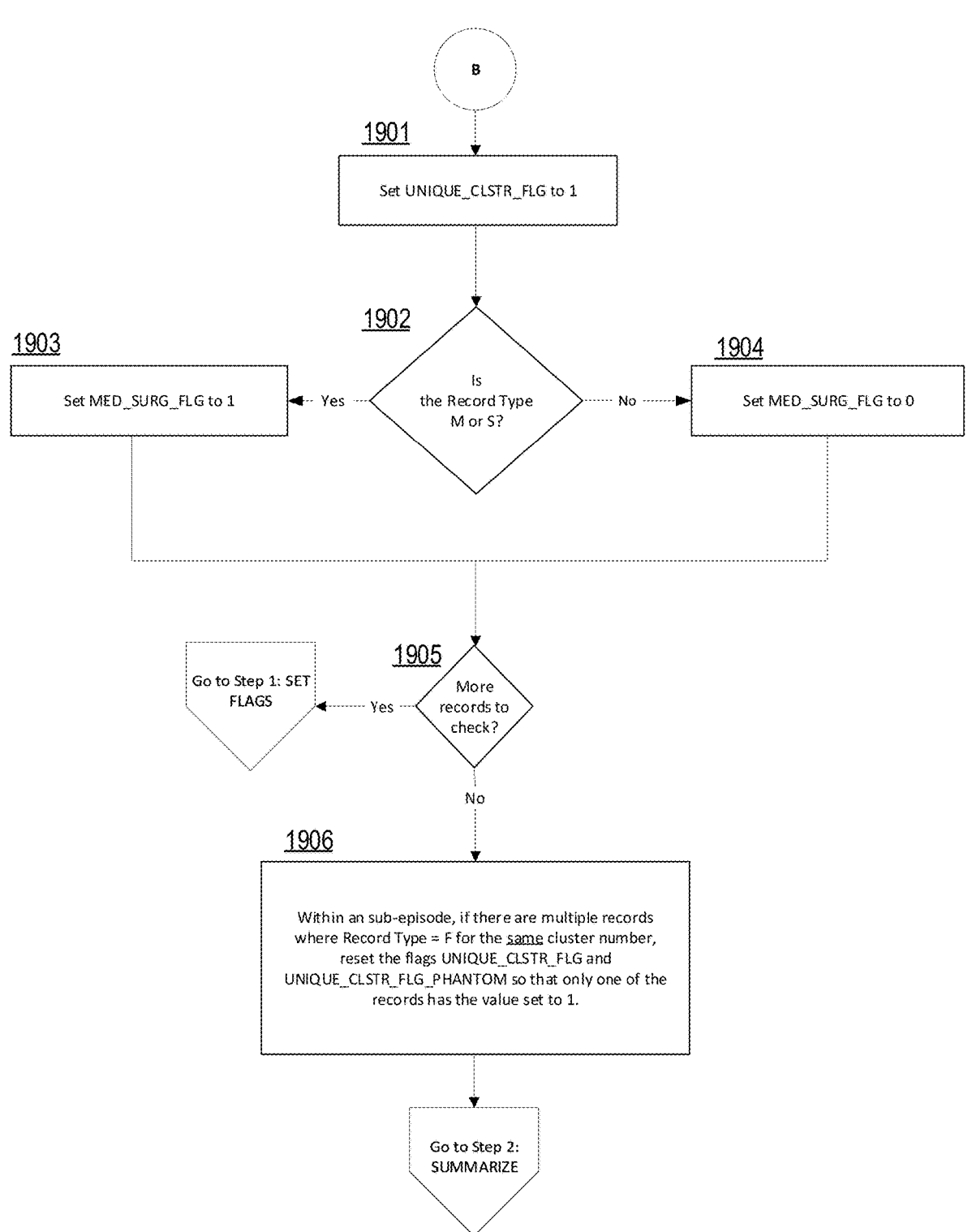

The data management computing entity 65 continues to provide appropriate flags to the claim record as indicated in FIG. 18. As indicated at Block 1801, the data management computing entity 65 is configured to identify a first date of service of an anchor record to determine whether the first date of service is the earliest date of the sub-episode. An appropriate flag (e.g., indicating that the first date of service of the anchor record is or is not the earliest date of the sub-episode) is set as indicated at Blocks 1802-1803.

As indicated at Block 1804, the data management computing entity 65 determines whether the last date of service of the anchor record is the last date within the sub-episode, and the data management computing entity 65 sets a corresponding flag as indicated in Blocks 1805-1806.

As indicated at Block 1807, the data management computing entity 65 then determines whether the procedure/revenue code(s) of a sub-episode is indicated as "non-acute E&M" or another defined characteristic (with reference to a data table defining characteristics of specific procedure codes and/or revenue codes as shown in Block 1808, such as an etgProcedures data table defining such data). A corresponding flag is set for the sub-episode as indicated at Blocks 1809-1810.

As reflected within Block 1811, the data management computing entity 65 determines whether the procedure/revenue code is classified as Total E&M (with reference to a data table defining characteristics of specific procedure codes and/or revenue codes as shown in Block 1812, such as the etgProcedures data table discussed in reference to Block 1808). A corresponding flag is set for the sub-episode as indicated at Blocks 1813-1814.

The methodology for generating flags continues with subprocesses selected as relevant based upon a determination of whether the analyzed record is a phantom record, as reflected in Block 1815. Phantom records are then analyzed under the methodology discussed above in reference to FIG. 17, and non-phantom records are analyzed to set appropriate flags in accordance with the methodology of FIG. 19.

Figure 20:
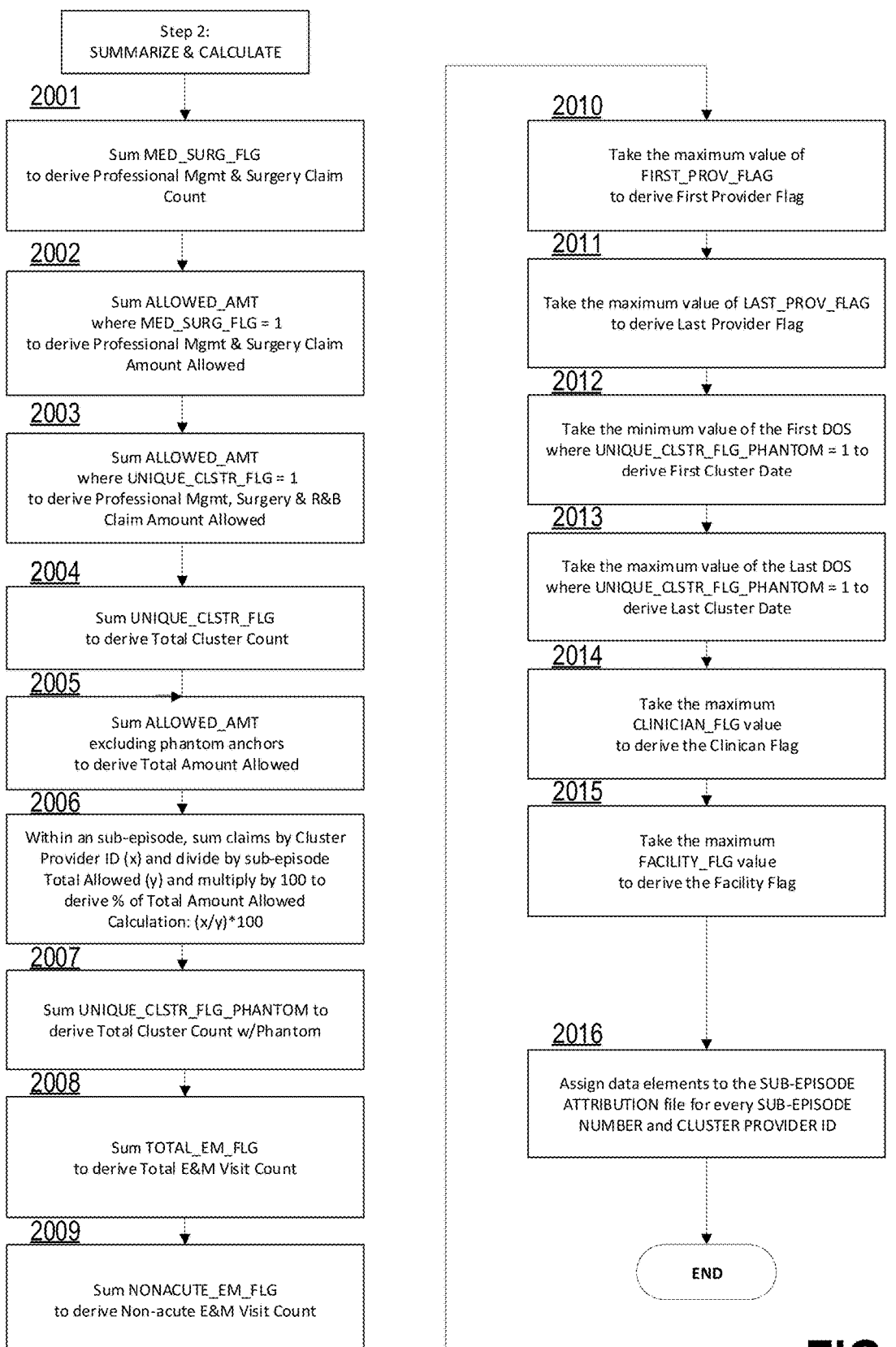

The process for setting flags relevant for non-phantom records begins by setting a unique cluster flag as indicated at Block 1901. The data management computing entity 65 then determines whether the claim record type is a medical or surgery record type, as indicated at Block 1902, and the data management computing entity 65 sets a corresponding flag as indicated at Blocks 1903-1904. The data management computing entity 65 then determines whether additional claim records are awaiting analysis as indicated at Block 1905 (looping back to the process discussed in reference to FIG. 17 for additional records) before determining whether, within a single sub-episode, there are multiple records of a facility record type for the same cluster number. Upon determining that there are multiple records within a single sub-episode of a facility record type for the same cluster, the unique cluster number flag for a plurality of these records is reset such that only one of the records has a flag value set to 1. The data management computing entity 65 then proceeds to the summary processes as indicated in FIG. 20.

As shown at Block 2001, the summary process begins by summing records relating to management and/or surgery records by summing those records having a flag indicating the claim record is a professional management or surgery claim. The generated total count of claims satisfying count criteria (e.g., having a management and surgery record claim flag) may be stored within a sub-episode summary record.

As indicated at Block 2002, the summary process continues by summing the allowed amounts (in currency) of management and surgery claim records for a particular sub-episode. The generated total summed amount may be stored within a sub-episode summary record.

As shown in Block 2003, the summary process continues by summing an allowed amount associated with those claim records having a unique cluster flag to determine an allowed amount associated with room and board costs of a sub-episode. The generated allowed amount may then be stored within a sub-episode summary record.

As shown in Block 2004, the total number of unique cluster flags may be determined to derive the total cluster count for a sub-episode. The generated total may be stored within a sub-episode summary record.

The total allowed amount associated with a sub-episode may be determined as indicated at Block 2005 by summing the total allowed amount of claim records associated with a sub-episode (that are not designed as phantom claim records). Because phantom records are duplicates of other already existing records, those phantom claim records are excluded from determinations of cost associated with a sub-episode to avoid double-counting costs of those records.

The amount of claim allowed amounts attributable to a particular provider is determined (e.g., in total and/or as a percentage of a total allowed amount for a sub-episode) as indicated at Block 2006. This process may be repeated for a plurality of providers (e.g., until all costs have been attributed to at least one provider such that all providers associated with a particular sub-episode are reflected within a percentage listing of costs attributed to each provider). Amounts attributed to each provider may be stored within the sub-episode summary record.

As indicated at Block 2007, a total cluster count, including phantom clusters, may be determined and stored within the sub-episode summary record. With reference to Block 2008, a total E&M visit count may be determined and stored within the sub-episode summary record. A nonacute E&M visit count may be determined as indicated at Block 2009, and the resulting count may be stored within the sub-episode summary record.

First provider flags and Last provider flags (as established in reference to Blocks 1801-1803 of FIG. 18) may be generated for the sub-episode as reflected within Blocks 2010-2011 by identifying the provider having an associated maximum first provider flag and maximum last provider flag, respectively. These first provider flags and last provider flags may be assigned to providers responsible for an earliest anchor record within a sub-episode and a latest anchor record within a sub-episode, respectively. An indicator of the first provider and the last provider may be stored within the sub-episode summary record.

First and last cluster dates may be determined for the sub-episode, as indicated at Blocks 2012-2013, and indications of the first and last clusters may be stored within the sub-episode summary record.

A clinician flag as discussed in reference to Blocks 1709-1711 may be developed for the sub-episode and assigned to the sub-episode summary record as indicated at Block 2014. Similarly, a facility flag as discussed in reference to Blocks 1712-1714 may be developed for the sub-episode and assigned to the sub-episode summary record as indicated at Block 2015.

Moreover, as discussed in reference to analysis of parent episodes, above, sub-episodes may be attributed to particular providers based at least in part on various characteristics of the sub-episode. For example, all providers associated with at least one claim record of a sub-episode may be reviewed to determine whether the sub-episode is to be attributed to the provider. The provider ultimately deemed responsible for the sub-episode (to which the sub-episode is attributed) may be identified as having a first provider flag, a last provider flag, a provider having a highest percentage of costs associated with the sub-episode, and/or the like.

Block 2016 indicates that the sub-episode data record may be updated to include data relevant to the sub-episode and determined in accordance with the summary process discussed herein. The summary data record may be stored in an appropriate data storage area to facilitate generation of output as discussed herein. Moreover, generation of the summary data record for all sub-episodes identified for a particular episode may finalize the process for generating a complete episode, and therefore the temporarily stored episode data object may be finalized and stored for later access. The temporarily stored episode data object may be updated to reflect the hierarchical structure including the data objects generated for each sub-episode (e.g., the sub-episode summary data records). The sub-episode data objects may be stored in association with the episode data objects, for example by utilizing a unique identifier within each data object to link the sub-episode data object with the episode data object. In other embodiments, the sub-episode data object may be stored within the episode-data object, for example, by updating particular data elements within the episode data object to reflect the presence of a sub-episode data object (e.g., by placing metadata tags on particular data elements of the episode data object indicating that such data elements are associated with a sub-episode).

Figure 21:
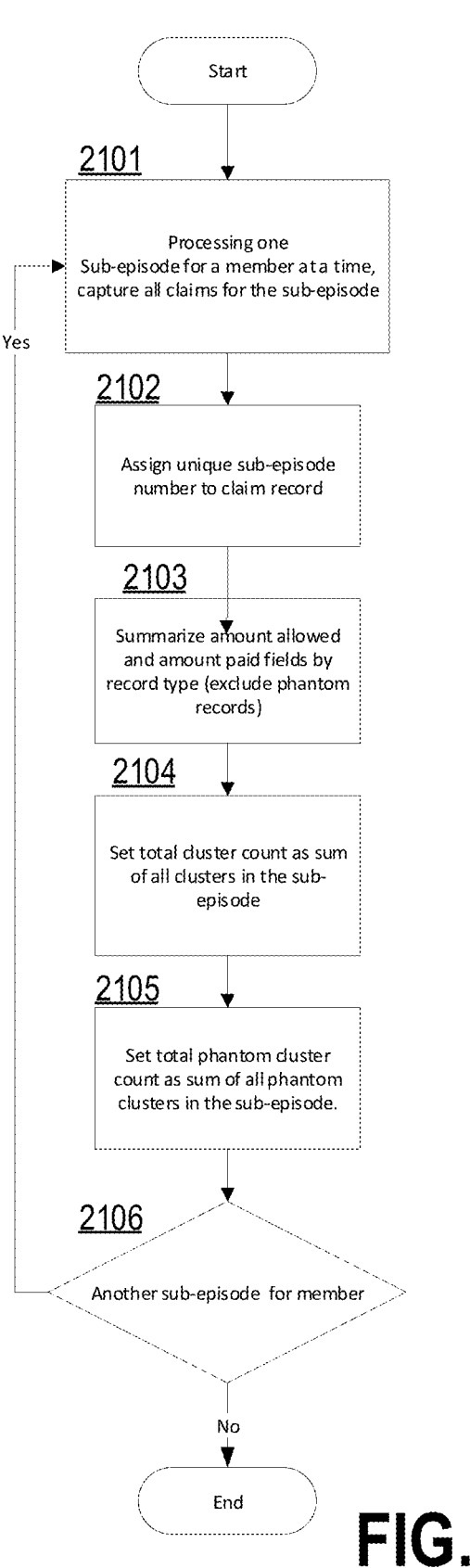

FIG. 21 provides additional data regarding generation of output relating to a sub-episode data record. As indicated at Bock 2101 records are generated and processed individually for each sub-episode, and the data management computing entity 65 collects all claim records associated with a particular sub-episode.

As shown at Block 2102, the data management computing entity 65 assigns a unique sub-episode number to each claim record to associate those claim records with the sub-episode, and the individual claim records may be updated to reflect the sub-episode association.

Moreover, as indicated at Block 2103, the data management computing entity 65 is configured to summarize allowed amount and amount paid fields of claim record to provide a total allowed amount and a total amount paid for a sub-episode. Such data may be updated to be reflected within a sub-episode summary record.

The data management computing entity 65 may then generate a total cluster count associated with the sub-episode as indicated at Block 2104. Similarly, the data management computing entity 65 may determine a total phantom cluster count for each sub-episode as indicated at Block 2105, before looping through the process to generate summary records for additional sub-episodes as indicated at Block 2106.

e. Output Generation

After the core data management computing entity 65 has established and finalized episodes (inclusive of sub-episodes, if applicable), the data management computing entity 65 generates one or more output files that may provide input to a variety of downstream processes, such as the generation of dashboards to be displayed to users, the initiation of various payments to providers, the generation of aggregated reports to be provided to government-based payors, and/or the like. The data management computing entity 65 of certain embodiments is configured to generate reports in a variety of formats as required by a user, such as generation of patient-specific data outputs providing data indicative of one or more episodes associated with a patient according to certain embodiments, periodic aggregate data outputs providing data indicative of one or more episodes satisfying aggregation criteria (e.g., associated with a particular provider, associated with a particular payer, associated with a plurality of patients having defined aggregation criteria, such as falling within a defined age range, having a defined gender, and/or the like) and falling within a defined reporting period, and/or the like. In certain embodiments, periodic reporting or reporting outputs generated in association with a defined time period may impact the manner in which the data management computing entity 65 assign date ranges to particular episodes, or those reporting-related time periods are utilized to select episodes for inclusion within the generated reports and associated generated reporting data objects. For example, those reporting data objects may comprise data representative of episodes that fall entirely within the date range of the reporting period. Moreover, chronic episodes may be included within the generated reporting data objects with start and end dates corresponding with the reporting period. Acute episodes that cross a start date or end date of a reporting period may be included within the generated reporting data object. In certain embodiments, only a subset of acute episodes that cross a start date or end date of the reporting period may be included within the reporting data object, such as episodes having at least one record falling within the reporting period, or episodes having at least one anchor record falling within the reporting period.

V. CONCLUSION

Many modifications and other embodiments will come to mind to one skilled in the art to which this disclosure pertains having the benefit of the teachings presented in the foregoing descriptions and the associated drawings. There-fore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A computer-based system comprising one or more processors and memory, the computer-based system config-ured to:
  store, by the one or more processors and in the memory, a plurality of individual claim records, wherein each individual claim record of the plurality of individual claim records has a non-hierarchical data structure;
  generate, by the one or more processors, a plurality of single-level episode data objects, each of the plurality of single-level episode data objects relating to an episode-specific subset of individual claim records of the plurality of individual claim records, wherein each single-level episode data object of the plurality of single-level episode data objects identifies a first parent episode record of the episode-specific subset of indi-vidual claim records, and wherein the first parent episode record identifies one or more characteristics of a corresponding single-level episode data object;
  retrieve, by the one or more processors and based at least in part on data stored within the plurality of single-level episode data objects, a reference table stored in the memory, wherein the reference table comprises a plu-rality of data entries identifying one or more charac-teristics of single-level episode data objects that are eligible for supporting one or more sub-episodes;
  identify, by the one or more processors and from the plurality of single-level episode data objects and based at least in part on the reference table, an eligible subset of the plurality of single-level episode data objects eligible for supporting the one or more sub-episodes;
  retrieve, by the one or more processors and from the memory, one or more sub-episode eligibility criteria comprising sub-episode eligibility criteria reference data tables;
  for a first single-level episode data object of the eligible subset, sequentially generate, by the one or more pro-cessors, one or more entries of a sub-episode eligibility listing in the memory based at least in part on charac-teristics identified for the first single-level episode data object, wherein each of the one or more entries has a corresponding individual claim record associated with the first single-level episode data object;
  identify, by the one or more processors and from the one or more entries, one or more sub-episode records satisfying the one or more sub-episode eligibility cri-teria;
  generate, by the one or more processors, one or more first sub-episode data objects that identify at least one of the one or more sub-episode records;
  update, by the one or more processors, the one or more first sub-episode data objects based at least in part on the one or more characteristics of the first single-level episode data object;
  transform, by the one or more processors, the first single-level episode data object into a multi-level hierarchical data object having metadata tags providing a hierarchi-cal data structure comprising one or more sub-episode identifiers corresponding with the one or more first sub-episode data objects; and
  store, by the one or more processors and into the memory, the multi-level hierarchical data object.

2. The computer-based system of claim 1, wherein the computer-based system is further configured to:
  identify, by the one or more processors and from the one or more entries, one or more sub-episode anchor records satisfying the one or more sub-episode eligi-bility criteria;
  identify, by the one or more processors and from the plurality of individual claim records, one or more sub-episode ancillary records associated with the one or more sub-episode anchor records;
  generate, by the one or more processors, one or more second sub-episode data objects that each identifies one of the one or more sub-episode anchor records and the one or more sub-episode ancillary records; and
  cause, by the one or more processors and based at least in part on the multi-level hierarchical data object, display of a multi-level view of at least one of the one or more sub-episode anchor records or the one or more sub-episode ancillary records identified by the one or more second sub-episode data objects;
  wherein each single-level episode data object of the plurality of single-level episode data objects identifies (a) a parent episode date range indicating an episode start date and an episode end date, (b) a first parent episode anchor record of a plurality of parent episode anchor records that corresponds to the episode-specific subset of individual claim records, wherein each parent episode anchor record of the plurality of parent episode anchor records identifies an episode type of the corre-sponding single-level episode data object.

3. The computer-based system of claim 2, wherein (a) the first parent episode anchor record is associated with the first single-level episode data object and comprises data identi-fying a plurality of diagnosis codes associated with the first parent episode anchor record, (b) the sub-episode eligibility criteria reference data tables comprise a listing of diagnosis codes eligible for supporting the one or more sub-episodes, and (c) generating the sub-episode eligibility listing com-prises identifying one or more diagnosis codes existing in both the first parent episode anchor record and the one or more sub-episode eligibility criteria.

4. The computer-based system of claim 2, wherein (a) the first parent episode anchor record identifies a procedure code associated with the first parent episode anchor record, (b) the sub-episode eligibility criteria reference data tables com-prise a listing of procedure codes eligible for supporting the one or more sub-episodes, and (c) generating the sub-episode eligibility listing comprises identifying one or more procedure codes existing in both the first parent episode anchor record and the one or more sub-episode eligibility criteria.

5. The computer-based system of claim 2, wherein the first single-level episode data object identifies a responsible provider for the first single-level episode data object, wherein the sub-episode eligibility criteria reference data tables comprise a listing of provider specialties eligible for supporting the one or more sub-episodes, and wherein the computer-based system is further configured to:
  determine a provider specialty associated with the respon-sible provider from one or more provider specialty tables; and
  determine whether the provider specialty of the respon-sible provider supports the one or more sub-episodes.

6. The computer-based system of claim 2, wherein identifying the one or more sub-episode ancillary records further comprises:

identifying a plurality of ancillary records not identified within the episode-specific subset of individual claim records associated with the one or more sub-episode anchor records; and truncating a first sub-episode date range of a sub-episode data object based at least in part on the parent episode date range and based at least in part on a second sub-episode date range of a second sub-episode associated with the first single-level episode data object such that the first sub-episode date range does not overlap the second sub-episode date range of the second sub-episode.

7. The computer-based system of claim 2, wherein identifying the one or more sub-episode anchor records comprises identifying a first sub-episode anchor record and a second sub-episode anchor record; and wherein the computer-based system is further configured to:

generate a sub-episode priority based at least in part on priority scores associated with each of the first sub-episode anchor record and the second sub-episode anchor record;

generate (a) a first sub-episode date range associated with the first sub-episode anchor record and (b) a second sub-episode date range associated with the second sub-episode anchor record; and truncate one of the first sub-episode date range or the second sub-episode date range based at least in part on the sub-episode priority such that the first sub-episode date range does not overlap the second sub-episode date range.

8. A computer-implemented method comprising:

storing, by one or more processors and in memory, a plurality of individual claim records, wherein each individual claim record of the plurality of individual claim records has a non-hierarchical data structure;

generating, by the one or more processors, a plurality of single-level episode data objects, each of the plurality of single-level episode data objects relating to an episode-specific subset of individual claim records of the plurality of individual claim records, wherein each single-level episode data object of the plurality of single-level episode data objects identifies a first parent episode record of the episode-specific subset of individual claim records, and wherein the first parent episode record identifies one or more characteristics of a corresponding single-level episode data object;

retrieving, by the one or more processors and based at least in part on data stored within the plurality of single-level episode data objects, a reference table stored in the memory, wherein the reference table comprises a plurality of data entries identifying one or more characteristics of single-level episode data objects that are eligible for supporting one or more sub-episodes;

identifying, by the one or more processors and from the plurality of single-level episode data objects and based at least in part on the reference table, an eligible subset of the plurality of single-level episode data objects eligible for supporting the one or more sub-episodes;

retrieving, by the one or more processors and from the memory, one or more sub-episode eligibility criteria comprising sub-episode eligibility criteria reference data tables;

for a first single-level episode data object of the eligible subset, sequentially generating, by the one or more processors, one or more entries of a sub-episode eligibility listing in the memory based at least in part on characteristics identified for the first single-level episode data object, wherein each of the one or more entries has a corresponding individual claim record associated with the first single-level episode data object;

identifying, by the one or more processors and from the one or more entries, one or more sub-episode records satisfying the one or more sub-episode eligibility criteria;

generating, by the one or more processors, one or more first sub-episode data objects that identify at least one of the one or more sub-episode records;

updating, by the one or more processors, the one or more first sub-episode data objects based at least in part on the one or more characteristics of the first single-level episode data object;

transforming, by the one or more processors, the first single-level episode data object into a multi-level hierarchical data object having metadata tags providing a hierarchical data structure comprising one or more sub-episode identifiers corresponding with the one or more first sub-episode data objects; and storing, by the one or more processors and into the memory, the multi-level hierarchical data object.

9. The computer-implemented method of claim 8, wherein the computer-implemented method further comprises:

identifying, by the one or more processors and from the one or more entries, one or more sub-episode anchor records satisfying the one or more sub-episode eligibility criteria;

identifying, by the one or more processors and from the plurality of individual claim records, one or more sub-episode ancillary records associated with the one or more sub-episode anchor records;

generating, by the one or more processors, one or more second sub-episode data objects that each identifies one of the one or more sub-episode anchor records and the one or more sub-episode ancillary records; and causing, by the one or more processors and based at least in part on the multi-level hierarchical data object, display of a multi-level view of at least one of the one or more sub-episode anchor records or the one or more sub-episode ancillary records identified by the one or more second sub-episode data objects;

wherein each single-level episode data object of the plurality of single-level episode data objects identifies (a) a parent episode date range indicating an episode start date and an episode end date, (b) a first parent episode anchor record of a plurality of parent episode anchor records that corresponds to the episode-specific subset of individual claim records, wherein each parent episode anchor record of the plurality of parent episode anchor records identifies an episode type of the corresponding single-level episode data object.

10. The computer-implemented method of claim 9, wherein (a) the first parent episode anchor record is associated with the first single-level episode data object and comprises data identifying a plurality of diagnosis codes associated with the first parent episode anchor record, (b) the sub-episode eligibility criteria reference data tables comprise a listing of diagnosis codes eligible for supporting the one or more sub-episodes, and (c) generating the subepisode eligibility listing comprises identifying one or more diagnosis codes existing in both the first parent episode anchor record and the one or more sub-episode eligibility criteria.

11. The computer-implemented method of claim 10, wherein the first single-level episode data object identifies a responsible provider for the first single-level episode data object, wherein the sub-episode eligibility criteria reference data tables comprise a listing of provider specialties eligible for supporting the one or more sub-episodes, and wherein the computer-implemented method further comprises:

determining a provider specialty associated with the responsible provider from one or more provider specialty tables; and determining whether the provider specialty of the responsible provider supports the one or more sub-episodes.

12. The computer-implemented method of claim 9, wherein identifying the one or more sub-episode ancillary records further comprises:

identifying a first plurality of ancillary records within the episode-specific subset of individual claim records associated with the one or more sub-episode anchor records;

identifying a second plurality of ancillary records not identified within the episode-specific subset of individual claim records associated with the one or more sub-episode anchor records;

determining a first sub-episode date range based at least in part on the first plurality of ancillary records associated with the one or more sub-episodes; and truncating the first sub-episode date range based at least in part on the parent episode date range and based at least in part on a second sub-episode date range of a second sub-episode associated with the first single-level episode data object such that the first sub-episode date range does not overlap the second sub-episode date range of the second sub-episode.

13. The computer-implemented method of claim 9, wherein identifying the one or more sub-episode anchor records comprises identifying a first sub-episode anchor record and a second sub-episode anchor record; and wherein the computer-implemented method further comprises:

generating a sub-episode priority based at least in part on priority scores associated with each of the first sub-episode anchor record and the second sub-episode anchor record;

generating (a) a first sub-episode date range associated with the first sub-episode anchor record and (b) a second sub-episode date range associated with the second sub-episode anchor record; and truncating one of the first sub-episode date range or the second sub-episode date range based at least in part on the sub-episode priority such that the first sub-episode date range does not overlap the second sub-episode date range.

14. The computer-implemented method of claim 8, wherein generating a single-level episode data object of the plurality of single-level episode data objects comprises storing the corresponding single-level episode data object within temporary storage.

15. A computer program product comprising one or more non-transitory computer-readable storage media having computer-readable program code portions stored therein, that when executed by one or more processors, cause the one or more processors to:

store, in memory, a plurality of individual claim records, wherein each individual claim record of the plurality of individual claim records has a non-hierarchical data structure;

generate a plurality of single-level episode data objects, each of the plurality of single-level episode data objects relating to an episode-specific subset of individual claim records of the plurality of individual claim records, wherein each single-level episode data object of the plurality of single-level episode data objects identifies a first parent episode record of the episode-specific subset of individual claim records, and wherein the first parent episode record identifies one or more characteristics of a corresponding single-level episode data object;

retrieve, based at least in part on data stored within the plurality of single-level episode data objects, a reference table stored in the memory, wherein the reference table comprises a plurality of data entries identifying one or more characteristics of single-level episode data objects that are eligible for supporting one or more sub-episodes;

identify, from the plurality of single-level episode data objects and based at least in part on the reference table, an eligible subset of the plurality of single-level episode data objects eligible for supporting the one or more sub-episodes;

retrieve, from the memory, one or more sub-episode eligibility criteria comprising sub-episode eligibility criteria reference data tables;

for a first single-level episode data object of the eligible subset, sequentially generate one or more entries of a sub-episode eligibility listing in the memory based at least in part on characteristics identified for the first single-level episode data object, wherein each of the one or more entries has a corresponding individual claim record associated with the first single-level episode data object;

identify, from the one or more entries, one or more sub-episode records satisfying the one or more sub-episode eligibility criteria;

generate one or more first sub-episode data objects that identify at least one of the one or more sub-episode records;

update the one or more first sub-episode data objects based at least in part on the one or more characteristics of the first single-level episode data object;

transform the first single-level episode data object into a multi-level hierarchical data object having metadata tags providing a hierarchical data structure comprising one or more sub-episode identifiers corresponding with the one or more first sub-episode data objects; and store, into the memory, the multi-level hierarchical data object.

16. The computer program product of claim 15, further comprising executable portions configured to:

identify, from the one or more entries, one or more sub-episode anchor records satisfying the one or more sub-episode eligibility criteria;

identify, from the plurality of individual claim records, one or more sub-episode ancillary records associated with the one or more sub-episode anchor records;

generate one or more second sub-episode data objects that each identifies one of the one or more sub-episode anchor records and the one or more sub-episode ancillary records; and cause, based at least in part on the multi-level hierarchical data object, display of a multi-level view of at least one of the one or more sub-episode anchor records or the one or more sub-episode ancillary records identified by the one or more second sub-episode data objects; and wherein each single-level episode data object of the plurality of single-level episode data objects identifies (a) a parent episode date range indicating an episode start date and an episode end date, (b) a first parent episode anchor record of a plurality of parent episode anchor records that corresponds to the episode-specific subset of individual claim records, wherein each parent episode anchor record of the plurality of parent episode anchor records identifies an episode type of the corresponding single-level episode data object.

17. The computer program product of claim 16, wherein (a) the first parent episode anchor record is associated with the first single-level episode data object and comprises data identifying a plurality of diagnosis codes associated with the first parent episode anchor record, (b) the sub-episode eligibility criteria reference data tables comprise a listing of diagnosis codes eligible for supporting the one or more sub-episodes, and (c) generating the sub-episode eligibility listing comprises identifying one or more diagnosis codes existing in both the first parent episode anchor record and the one or more sub-episode eligibility criteria.

18. The computer program product of claim 17, wherein (a) the first parent episode anchor record identifies a procedure code associated with the first parent episode anchor record, (b) the sub-episode eligibility criteria reference data tables comprise a listing of procedure codes eligible for supporting the one or more sub-episodes, and (c) generating the sub-episode eligibility listing comprises identifying one or more procedure codes existing in both the first parent episode anchor record and the one or more sub-episode eligibility criteria.

19. The computer program product of claim 17, wherein the first single-level episode data object identifies a responsible provider for the first single-level episode data object, wherein the sub-episode eligibility criteria reference data tables comprise a listing of provider specialties eligible for supporting the one or more sub-episodes, and further comprising executable portions configured to:

determine a provider specialty associated with the responsible provider from one or more provider specialty tables; and determine whether the provider specialty of the responsible provider supports the one or more sub-episodes.

20. The computer program product of claim 16, wherein identifying the one or more sub-episode ancillary records further comprises:

identifying a plurality of ancillary records not identified within the episode-specific subset of individual claim records associated with the one or more sub-episode anchor records; and truncating a first sub-episode date range of a sub-episode data object based at least in part on the parent episode date range and based at least in part on a second sub-episode date range of a second sub-episode associated with the first single-level episode data object such that the first sub-episode date range does not overlap the second sub-episode date range of the second sub-episode.

\* \* \* \* \*